(12) United States Patent
Lubbers et al.

(10) Patent No.: US 7,708,759 B2
(45) Date of Patent: *May 4, 2010

(54) APPARATUS AND METHODS FOR SECURING TENDONS OR LIGAMENTS TO BONE

(75) Inventors: Lawrence M. Lubbers, Columbus, OH (US); Kenneth E. Hughes, Pataskala, OH (US); Carl R. Coleman, Powell, OH (US); Warren P. Williamson, IV, Loveland, OH (US); Craig B. Berky, Milford, OH (US); Thomas J. Ward, Columbus, OH (US)

(73) Assignee: Tendon Technology, Ltd., Pataskala, OH (US)

( * ) Notice: Subject to any disclaimer, the term of this patent is extended or adjusted under 35 U.S.C. 154(b) by 1574 days.

This patent is subject to a terminal disclaimer.

(21) Appl. No.: 10/620,932

(22) Filed: Jul. 16, 2003

(65) Prior Publication Data

US 2004/0024420 A1    Feb. 5, 2004

Related U.S. Application Data

(60) Division of application No. 09/969,947, filed on Oct. 3, 2001, now Pat. No. 6,984,241, which is a continuation-in-part of application No. PCT/US99/24098, filed on Oct. 18, 1999, which is a continuation-in-part of application No. 08/928,866, filed on Sep. 12, 1997, now Pat. No. 6,083,244.

(60) Provisional application No. 60/026,101, filed on Sep. 13, 1996, provisional application No. 60/043,086, filed on Apr. 8, 1997.

(51) Int. Cl.
    *A61B 17/04* (2006.01)
(52) U.S. Cl. ....................................... 606/232

(58) Field of Classification Search .................. 606/232
See application file for complete search history.

(56) References Cited

U.S. PATENT DOCUMENTS 2,075,508  A    3/1937   Davidson (Continued)

FOREIGN PATENT DOCUMENTS

DE    1810800    6/1970

(Continued)

OTHER PUBLICATIONS

L. Gordon et al., *Flexor Tendon Repair Using a Stainless Steel Internal Anchor*, Article, The Journal of Hand Surgery, vol. 23B N. 1, Feb. 1998.

(Continued)

*Primary Examiner*—Todd E Manahan
*Assistant Examiner*—Michael G Mendoza
(74) *Attorney, Agent, or Firm*—Wood, Herron & Evans, L.L.P.

(57) ABSTRACT

Apparatus and methods for repairing damaged tendons or ligaments. Various repair apparatus include an elongate tensile member and a pair of anchor structures connected for movement along the tensile member on either side of a repair site, such as a tear or laceration. The anchor structures may take many forms, and may include barbed, helical, and crimp-type anchors. In the preferred embodiments, at least one anchor structure is movable along the elongate tensile member to assist with adjusting a tendon segment to an appropriate repair position and the anchor structure or structures are then lockable onto the elongate tensile member to assist with affixing the tendon at the repair position. Tendon-to-bone repair apparatus and methods are also disclosed employing similar concepts. Tendon retrieval devices include helical members for rotating into a tendon end and subsequently moving the tendon to an appropriate operating position.

8 Claims, 29 Drawing Sheets

U.S. PATENT DOCUMENTS

| | | | |
|---|---|---|---|
| 2,421,193 A | 5/1947 | Gardner | 128/335 |
| 2,472,009 A | 5/1949 | Gardner | 128/335 |
| 2,489,870 A | 11/1949 | Dzus | 606/73 |
| 2,760,488 A | 8/1956 | Pierce | |
| 3,123,077 A | 3/1964 | Alcamo | 606/228 |
| 3,489,143 A | 1/1970 | Halloran | |
| 3,664,345 A | 5/1972 | Dabbs | |
| 3,716,058 A | 2/1973 | Tanner, Jr. | 128/337 |
| 3,753,438 A | 8/1973 | Wood et al. | |
| 4,430,998 A | 2/1984 | Harvey et al. | 128/335 |
| 4,535,772 A | 8/1985 | Sheehan | |
| 4,537,185 A | 8/1985 | Stednitz | |
| 4,549,545 A | 10/1985 | Levy | 606/223 |
| 4,585,458 A | 4/1986 | Kurland | 623/13.17 |
| 4,590,928 A | 5/1986 | Hunt et al. | |
| 4,592,346 A | 6/1986 | Jurgutis | 128/92 |
| 4,637,380 A | 1/1987 | Orejola | 128/334 |
| 4,643,178 A | 2/1987 | Nastari et al. | |
| 4,723,548 A | 2/1988 | Lalonde | 128/335 |
| 4,741,330 A * | 5/1988 | Hayhurst | 606/144 |
| 4,750,492 A | 6/1988 | Jacobs | 606/230 |
| 4,796,612 A | 1/1989 | Reese | |
| 4,832,026 A | 5/1989 | Jones | |
| 4,834,752 A | 5/1989 | Van Kampen | |
| 4,870,957 A | 10/1989 | Goble et al. | 128/92 |
| 4,873,976 A | 10/1989 | Schreiber | 128/334 |
| 4,901,721 A | 2/1990 | Hakki | 606/103 |
| 4,927,421 A | 5/1990 | Goble et al. | |
| 4,946,462 A | 8/1990 | Watanabe | |
| 4,950,270 A | 8/1990 | Bowman et al. | |
| 4,955,910 A | 9/1990 | Bolesky | 623/13.13 |
| 4,978,347 A | 12/1990 | Ilizarov | |
| 4,979,956 A | 12/1990 | Silvestrini | 623/13 |
| 4,988,351 A | 1/1991 | Paulos et al. | 606/72 |
| 5,006,023 A | 4/1991 | Kaplan | 411/17 |
| 5,013,316 A | 5/1991 | Goble et al. | |
| 5,041,129 A | 8/1991 | Hayhurst et al. | 606/232 |
| 5,053,047 A | 10/1991 | Yoon | 606/223 |
| 5,061,283 A | 10/1991 | Silvestrini | 623/13 |
| 5,084,050 A | 1/1992 | Draenert | |
| 5,123,914 A * | 6/1992 | Cope | 606/232 |
| 5,152,765 A | 10/1992 | Ross et al. | |
| 5,156,616 A | 10/1992 | Meadows et al. | |
| 5,236,431 A | 8/1993 | Gogolewski et al. | |
| 5,254,127 A | 10/1993 | Wholey et al. | |
| 5,258,015 A | 11/1993 | Li et al. | |
| 5,263,973 A | 11/1993 | Cook | |
| 5,269,290 A | 12/1993 | Barrett et al. | 128/4 |
| 5,269,809 A | 12/1993 | Hayhurst et al. | |
| 5,306,290 A | 4/1994 | Martins et al. | |
| 5,309,927 A | 5/1994 | Welch | 128/898 |
| 5,342,376 A | 8/1994 | Ruff | |
| 5,354,305 A | 10/1994 | Lewis et al. | 606/152 |
| 5,380,334 A | 1/1995 | Torrie et al. | 606/104 |
| 5,383,897 A | 1/1995 | Wholey | 606/213 |
| 5,395,374 A | 3/1995 | Miller et al. | |
| 5,411,523 A | 5/1995 | Goble | 606/232 |
| 5,417,699 A | 5/1995 | Klein et al. | 606/139 |
| 5,425,747 A | 6/1995 | Brotz | 606/228 |
| 5,426,843 A | 6/1995 | Bartky | 29/516 |
| 5,433,607 A | 7/1995 | Schmid et al. | 433/173 |
| 5,464,424 A | 11/1995 | O'Donnell, Jr. | 606/228 |
| 5,472,452 A | 12/1995 | Trott | 606/232 |
| 5,480,403 A | 1/1996 | Lee et al. | |
| 5,486,197 A | 1/1996 | Le et al. | |
| 5,500,000 A | 3/1996 | Feagin et al. | |
| 5,505,735 A | 4/1996 | Li | 606/72 |
| 5,507,775 A | 4/1996 | Ger et al. | 606/216 |
| 5,520,691 A | 5/1996 | Branch | |
| 5,520,700 A | 5/1996 | Beyar et al. | 606/139 |
| 5,527,342 A | 6/1996 | Pietrzak et al. | 606/232 |
| 5,531,232 A | 7/1996 | Hill | 128/898 |
| 5,531,761 A | 7/1996 | Yoon | 606/223 |
| 5,531,790 A | 7/1996 | Frechet et al. | 623/15 |
| 5,536,270 A | 7/1996 | Songer et al. | |
| 5,556,428 A | 9/1996 | Shah | 623/13 |
| 5,562,689 A | 10/1996 | Green et al. | 606/151 |
| 5,571,139 A | 11/1996 | Jenkins, Jr. | |
| 5,582,616 A | 12/1996 | Bolduc et al. | 606/143 |
| 5,584,859 A | 12/1996 | Brotz | 606/228 |
| 5,593,425 A | 1/1997 | Bonutti et al. | 606/232 |
| 5,601,557 A | 2/1997 | Hayhurst | 606/72 |
| 5,626,613 A | 5/1997 | Schmieding | |
| 5,643,289 A | 7/1997 | Sauer et al. | 606/139 |
| 5,643,320 A | 7/1997 | Lower et al. | 606/232 |
| 5,662,714 A | 9/1997 | Charvin et al. | 623/15 |
| 5,669,917 A | 9/1997 | Sauer et al. | 606/139 |
| 5,681,352 A | 10/1997 | Clancy, III et al. | 606/232 |
| 5,683,417 A | 11/1997 | Cooper | |
| 5,690,632 A | 11/1997 | Schwartz et al. | 606/73 |
| 5,693,046 A | 12/1997 | Songer et al. | |
| 5,702,397 A | 12/1997 | Goble et al. | |
| 5,707,394 A | 1/1998 | Miller et al. | 606/232 |
| 5,707,395 A | 1/1998 | Li | 606/232 |
| 5,720,765 A | 2/1998 | Thal | |
| 5,723,008 A | 3/1998 | Gordon | 623/13 |
| 5,723,009 A | 3/1998 | Frechet et al. | 623/15 |
| 5,728,135 A | 3/1998 | Bregen et al. | 606/228 |
| 5,728,136 A | 3/1998 | Thal | 606/232 |
| 5,741,260 A | 4/1998 | Songer et al. | |
| 5,755,065 A | 5/1998 | Sorkin | 52/223.13 |
| 5,772,668 A | 6/1998 | Summers et al. | |
| 5,782,844 A | 7/1998 | Yoon et al. | 606/139 |
| 5,797,913 A | 8/1998 | Dambreville et al. | 606/72 |
| 5,800,544 A | 9/1998 | Demopulos et al. | 623/13 |
| 5,810,851 A | 9/1998 | Yoon | 606/148 |
| 5,824,008 A | 10/1998 | Bolduc et al. | 606/43 |
| 5,891,168 A | 4/1999 | Thal | 606/232 |
| 5,897,591 A | 4/1999 | Kobayashi | 623/13.11 |
| 5,916,224 A | 6/1999 | Esplin | 606/151 |
| RE36,289 E | 8/1999 | Le et al. | 606/232 |
| 5,951,590 A | 9/1999 | Goldfarb | 606/232 |
| 5,954,747 A | 9/1999 | Clark | 606/216 |
| 5,957,953 A | 9/1999 | DiPoto et al. | |
| 5,964,772 A | 10/1999 | Bolduc et al. | 606/142 |
| 5,972,001 A | 10/1999 | Yoon | 606/139 |
| 5,980,557 A | 11/1999 | Iserin et al. | 606/220 |
| 6,074,409 A | 6/2000 | Goldfarb | 606/232 |
| 6,083,244 A | 7/2000 | Lubbers et al. | 606/232 |
| 6,102,947 A | 8/2000 | Gordon | 623/13.11 |
| 6,106,556 A | 8/2000 | Demopulos et al. | 623/13.16 |
| 6,129,762 A | 10/2000 | Li | 623/13.11 |
| 6,132,442 A | 10/2000 | Ferragamo et al. | 606/151 |
| 6,149,669 A | 11/2000 | Li | 606/232 |
| 6,168,596 B1 | 1/2001 | Wellisz et al. | 606/69 |
| 6,190,401 B1 | 2/2001 | Green et al. | |
| 6,241,747 B1 | 6/2001 | Ruff | |
| 6,296,656 B1 | 10/2001 | Bolduc et al. | 606/213 |
| 6,306,159 B1 | 10/2001 | Schwartz et al. | 606/232 |
| 6,319,257 B1 | 11/2001 | Carignan et al. | |
| 6,368,326 B1 | 4/2002 | Dakin et al. | |
| 6,395,010 B1 | 5/2002 | Wotton, III | |
| 6,485,503 B2 | 11/2002 | Jacobs et al. | 606/215 |
| 6,666,877 B2 * | 12/2003 | Morgan et al. | 606/232 |
| 2001/0044637 A1 | 11/2001 | Jacobs et al. | |

FOREIGN PATENT DOCUMENTS

| | | |
|---|---|---|
| DE | 3227984 A1 | 2/1984 |
| DE | 19840881 | 3/2000 |

| | | |
|---|---|---|
| EP | 0092334 | 10/1983 |
| EP | 0478949 A1 | 4/1992 |
| EP | 0535802 | 4/1993 |
| GB | 2164562 | 3/1986 |
| WO | WO 97-07744 | 3/1997 |
| WO | WO 00/49983 | 8/2000 |

OTHER PUBLICATIONS

L. Gordon et al., *Flexor Tendon Repair Using a Stainless Steel External Splint*, Article, Journal of Hand Surgery, vol. 24B, No. 6, Dec. 1999.

Dietmar H. Wittmann, *Prosthesis for Abdominal Surgery*, U.S. Patent Publication No. 2002/O029063A1, Published on Mar. 7, 2002.

Daniel Jacobs, *Multi-Point Tension Distribution System Device and Method of Tissue Approximation Using that Device to Improve Wound Healing*, U.S. Patent Publication No. 2002/O173807A1, Published on Nov. 21, 2002.

U.S. Patent and Trademark Office, Office Action in U.S. Appl. No. 10/816,725, Sep. 30, 2008.

US 6,447,535, 09/2002, Jacobs et al. (withdrawn)

* cited by examiner

MULTIFILAMENT IN PLACE

FIXATION TAB (2 PLACES)

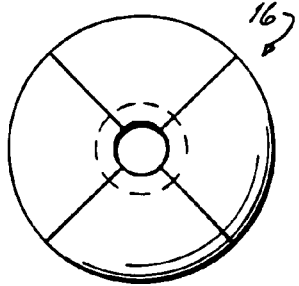
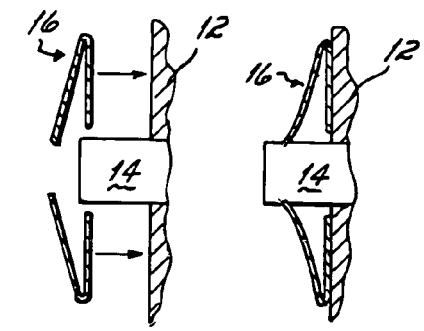
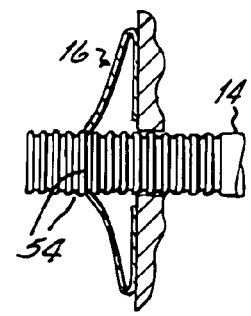
FIG. 7  FIG. 8  FIG. 9  FIG. 10
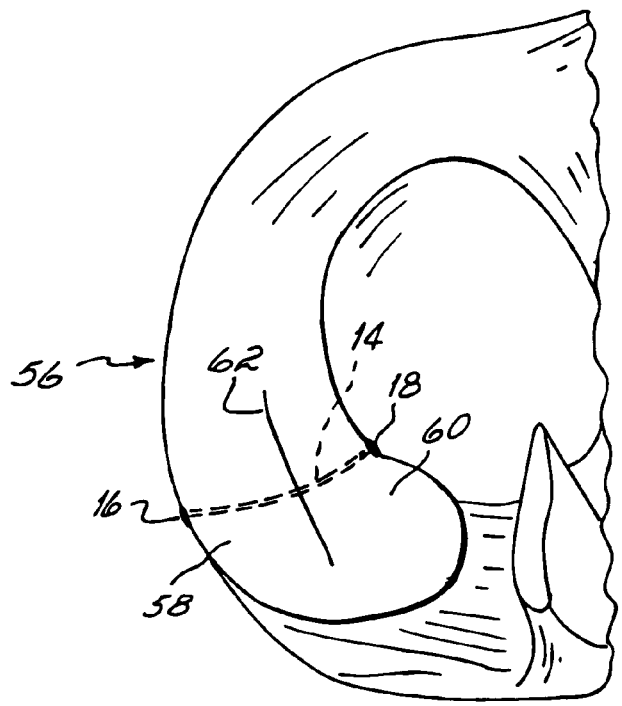
FIG. 11
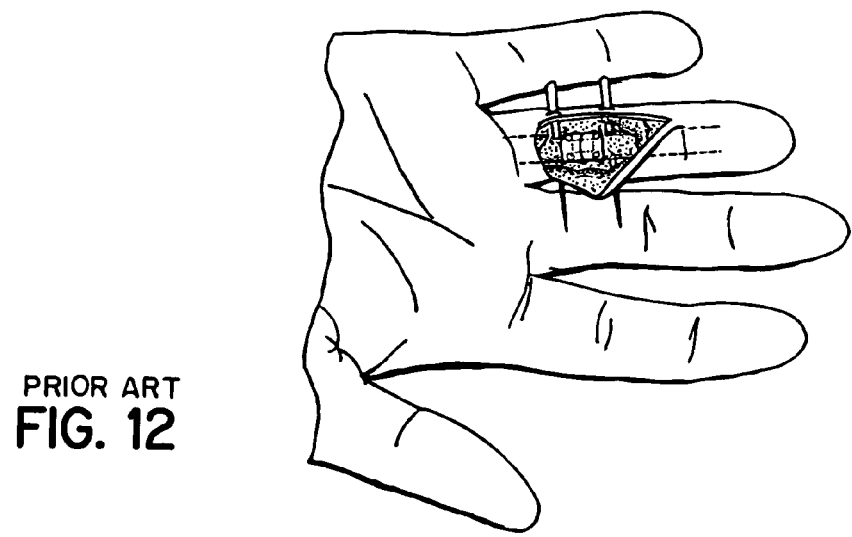
PRIOR ART
FIG. 12

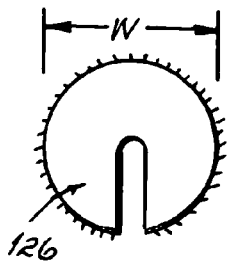 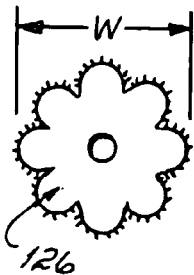 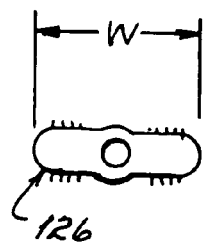 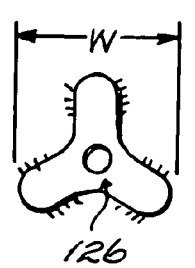
FIG. 15A  FIG. 15B  FIG. 15C  FIG. 15D
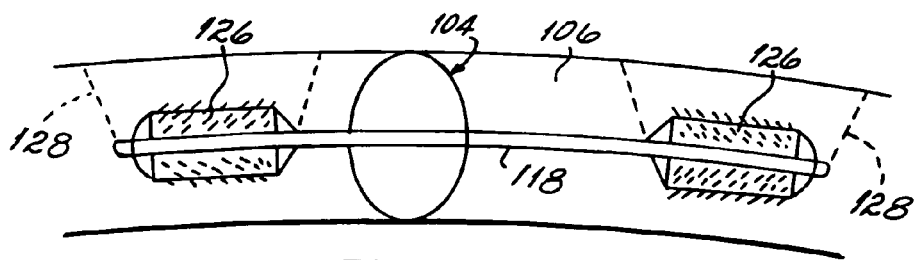
FIG. 16
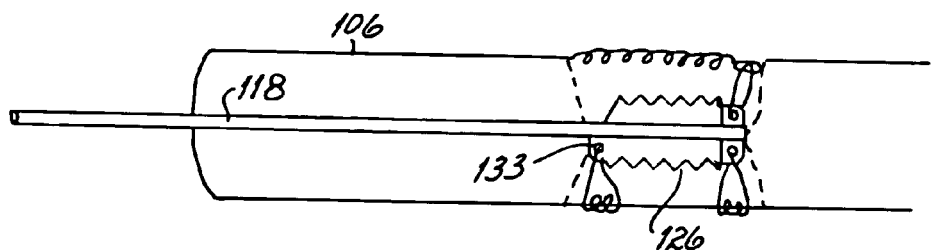
FIG. 16A
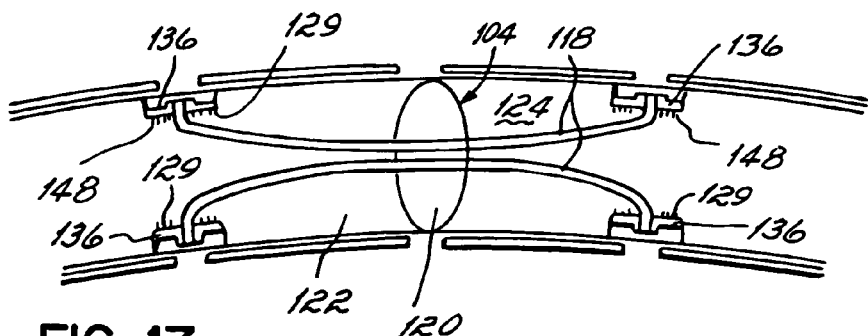
FIG. 17
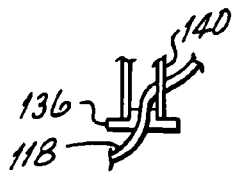
FIG. 17A
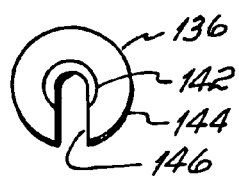
FIG. 17B

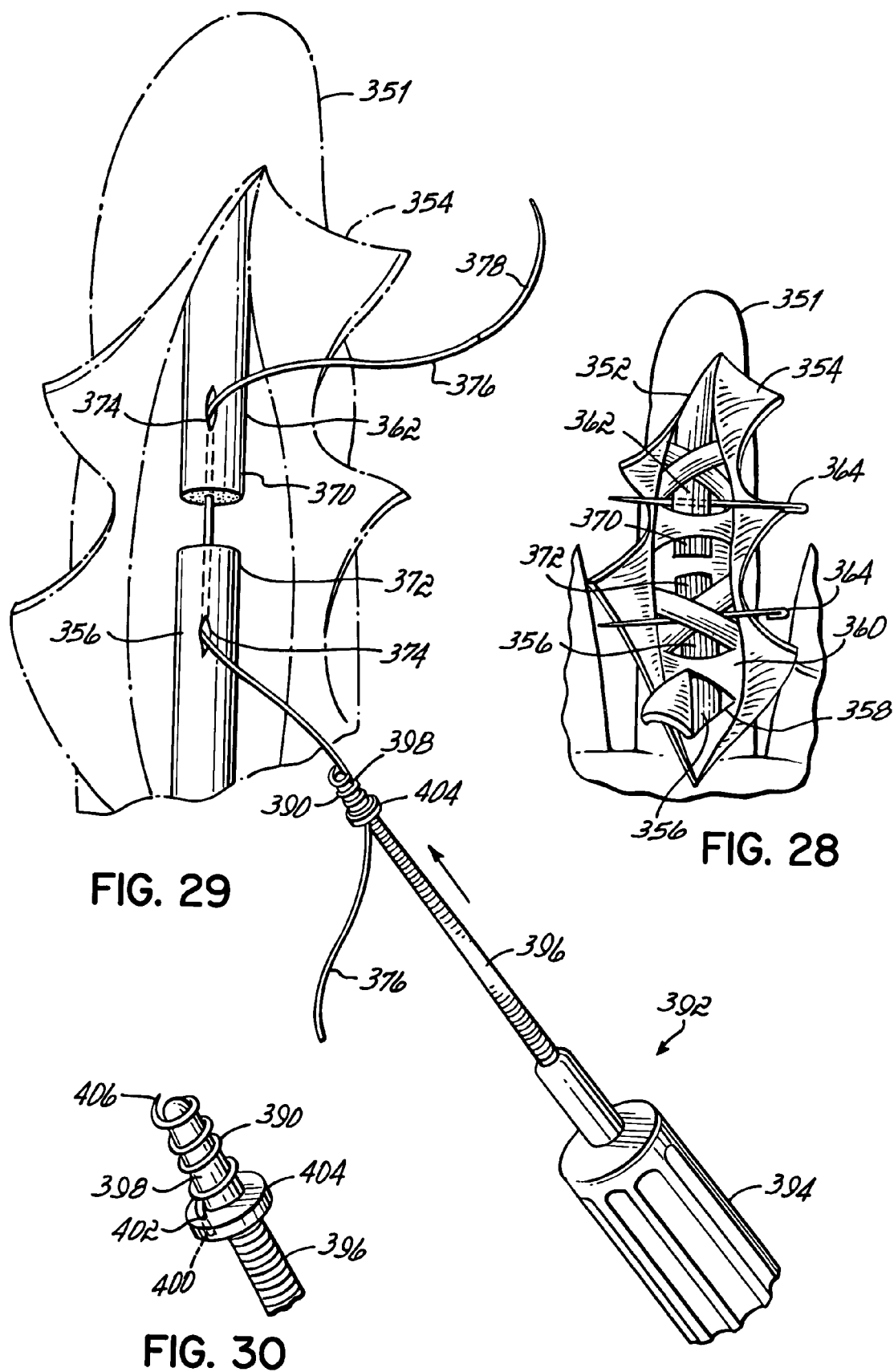

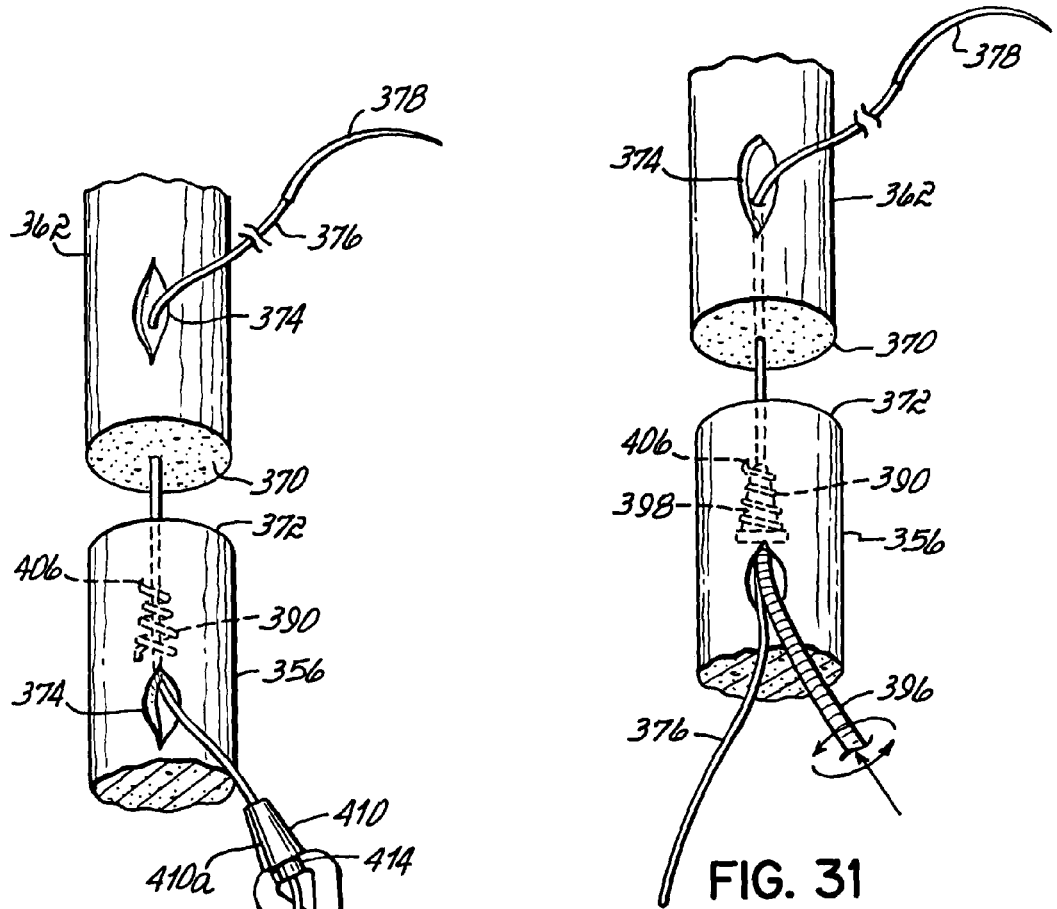
FIG. 31
FIG. 32
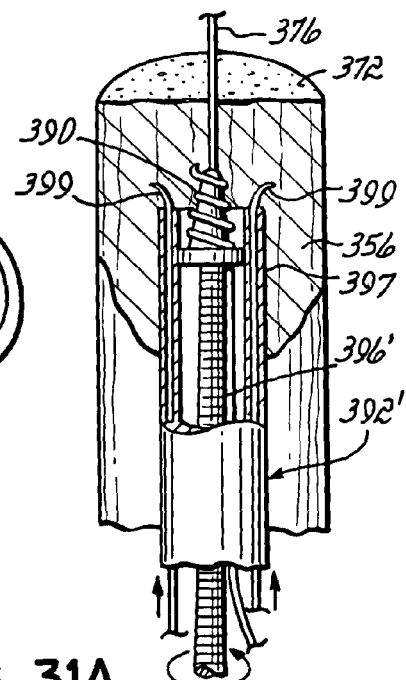
FIG. 31A

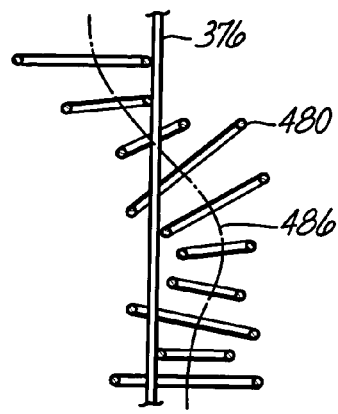 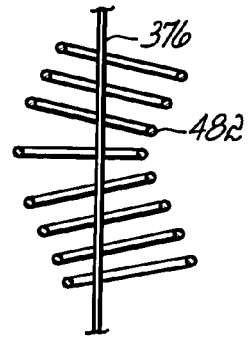 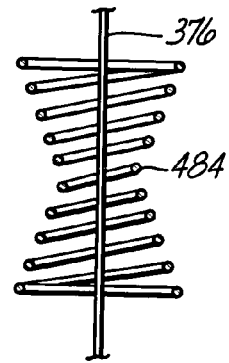
FIG.40　　FIG.41　　FIG.42
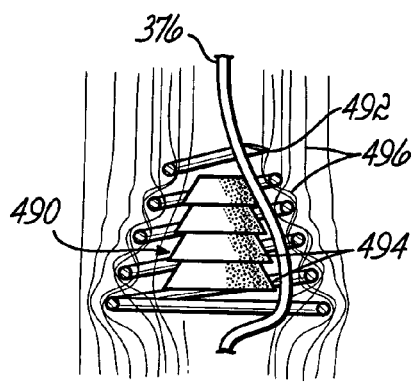 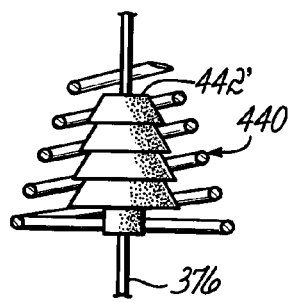 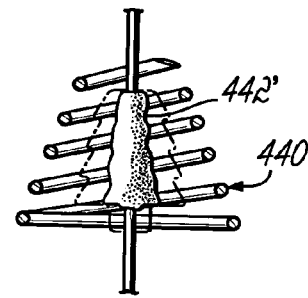
FIG.43　　FIG.44A　　FIG.44B
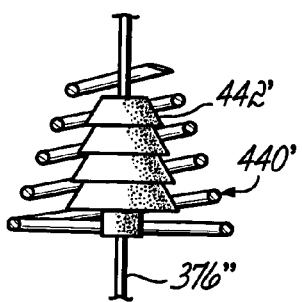 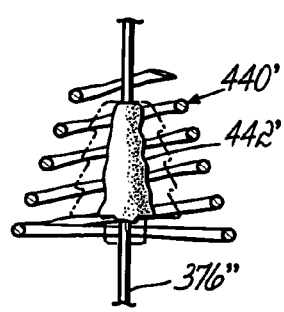 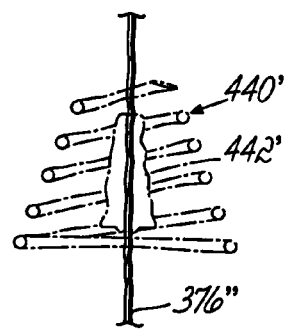
FIG. 45A　　FIG. 45B　　FIG. 45C

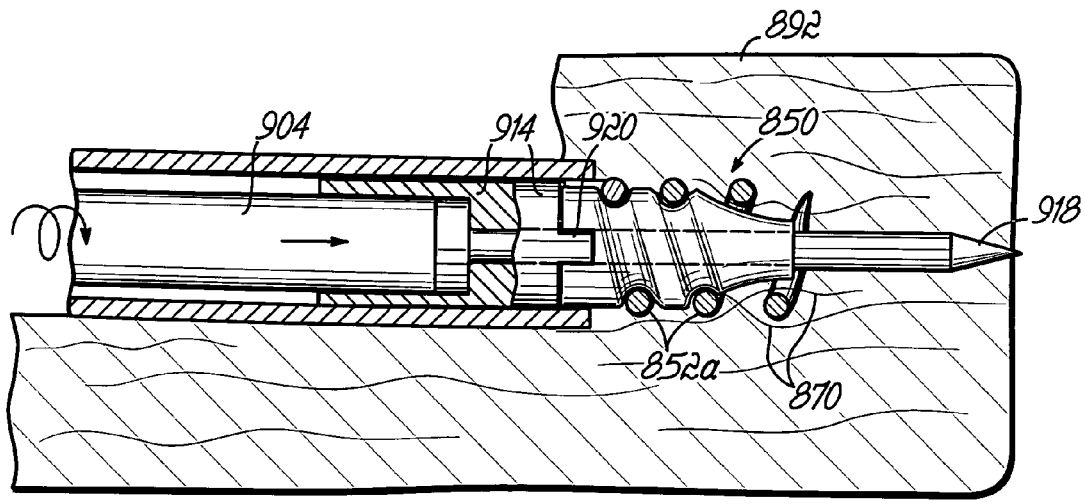
FIG. 79
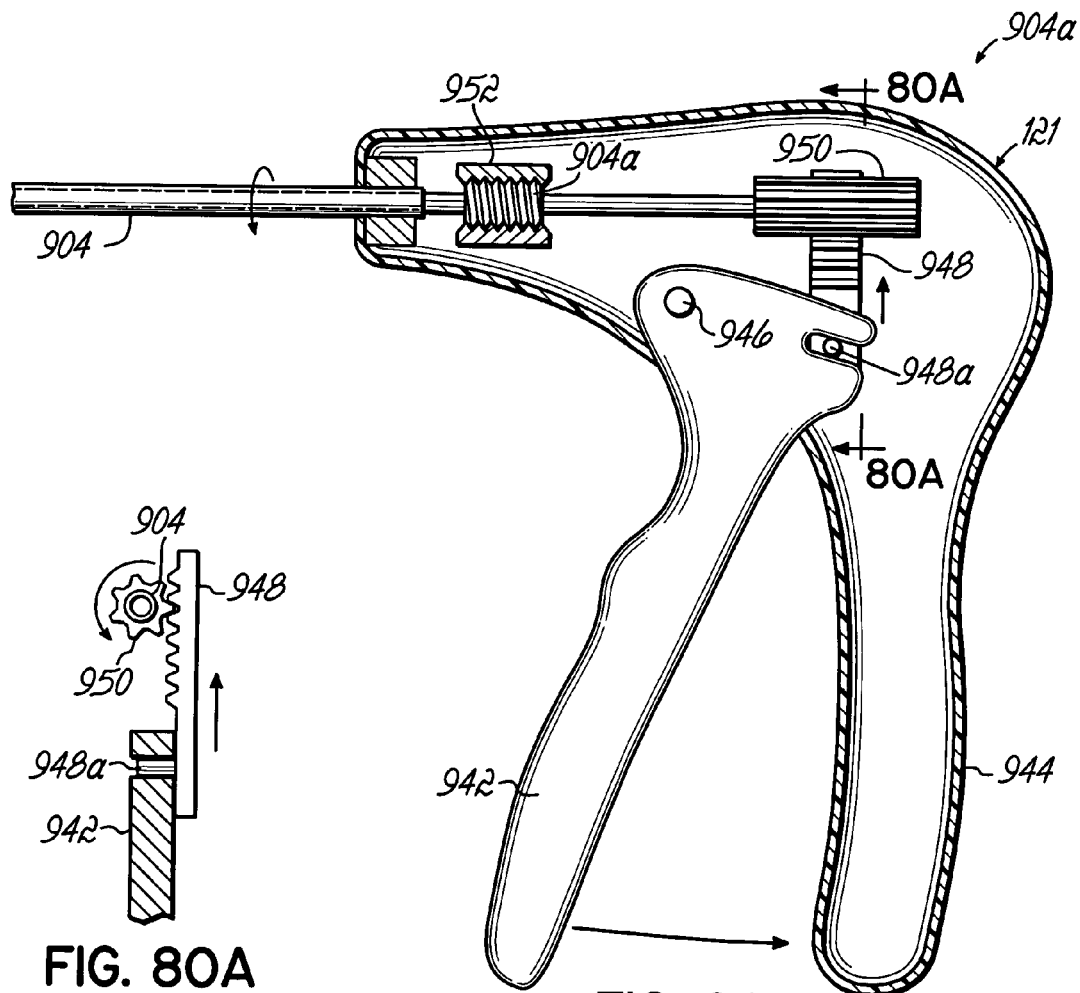
FIG. 80A
FIG. 80

APPARATUS AND METHODS FOR SECURING TENDONS OR LIGAMENTS TO BONE

The present application is a divisional of application Ser. No. 09/969,947, filed on Oct. 3, 2001 now U.S. Pat. No. 6,984,241, which is a continuation-in-part of PCT Serial No. PCT/US99/24098 filed on Oct. 18, 1999, which is a continuation-in-part of U.S. Ser. No. 08/928,866, filed on Sep. 12, 1997, now U.S. Pat. No. 6,083,244, which is based on provisional patent application Ser. No. 60/026,101, filed Sep. 13, 1996, now abandoned, and provisional patent application Ser. No. 60/043,086, filed on Apr. 8, 1997, now abandoned. The disclosures of each of these prior related applications are hereby fully incorporated by reference herein.

FIELD OF THE INVENTION

The present invention generally relates to tendon or ligament repair apparatus and methods. More specifically, the invention relates to the repair of severed or otherwise damaged tendons or ligaments and the attachment of tendons or ligaments to bone. As used herein, the terms "tendon" and "ligament" are used in a generally interchangeable manner.

BACKGROUND OF THE INVENTION

The repair of tendons or ligaments is a challenging and complication prone area of surgery. As one example, the dilemma in flexor tendon repair surgery in the hand is to adequately connect a severed tendon without compromising the functionality of the hand due to surgical intervention and repair techniques. Over the past 40 years, there have been only improvements in the basic suture techniques to repair tendons. In order to make any substantial improvement in the art of repairing a severed tendon one must first understand the composition and structure of tendons and ligaments.

Tendons can sustain high tensile forces resulting from muscle contraction, yet are flexible enough to bend around bony surfaces and deflect beneath retinacula to change the final direction of muscle pull. Tendons attach muscle to bone and transmit tensile loads from muscle to bone thereby producing joint movement. Ligaments attach bone to bone and can flex to allow natural movement of the bones that they attach, but are strong and inextensible so as to offer suitable resistance to applied forces. Ligaments augment the mechanical stability of the joints. The biomechanical behavior of tendons and ligaments is viscoelastic or rate dependent, that is, their strength and stiffness increase with an increased loading rate. Bundles of collagen fibers embedded in a connecting matrix, known as ground substance, provide the load carrying elements of natural tendons and ligaments. The arrangement of the collagen fibers is nearly parallel in tendons, equipping them to withstand high unidirectional loads. The less parallel arrangement of the collagen fibers in ligaments allows these structures to sustain predominant tensile stresses in one direction and smaller stresses in other directions. The ground substance in both tendons and ligaments acts generally as a cementing matrix holding the collagen fibers together. The ground substance retains large amounts of water essential to the non-compressive hydraulic function of the moving tissue. Also included in the tendon composition are elastic fibers, tenocytes, small blood vessels and nerves. In general, the cellular material (fibroblasts) occupies about 20% to 38% depending on references, of the total tissue volume, while the ground substance matrix accounts for the remaining 62% to 80%. About 70% of the ground substance matrix consists of water absorbed in an open polysaccharide matrix.

Two types of tendons exist in the hand for connecting phalanx (finger) bones to the appropriate muscles. Flexor tendons, which are connected to the volar or palm side of the fingers, lend the ability to curl the fingers towards the palm. Extensor tendons, which are connected to the dorsal or backside of the fingers, return the curled fingers back into a straight position. Sheaths and retinacula restrain most tendons in the hand to some extent and keep them close to the skeletal plane so that they maintain a relatively constant moment arm rather than bowstringing across the joints. The pulley system of the flexor tendon sheath in the finger is the most highly developed of these restraints. The flexor tendon sheath pulley system permits the flexor tendons to maintain a relatively constant moment arm and helps minimize stress risers between tendon and sheath. This system serves three important functions. First, it allows smooth tendon gliding or lubrication; second, the retinacular reinforcing pulleys maintain the flexor tendons close to the surface of the finger bones, preventing bowstringing; and third, it provides an enclosed synovial fluid environment for tendon nutrition and lubrication. As the finger moves, each tendon slides a certain distance, which defines the "excursion of the tendon". Excursion takes place simultaneously in the flexor and extensor tendons during joint motion. The tendons of the agonist, or contracting muscle, displace in one direction. The tendons of the antagonist or resisting muscles displace in the opposite direction to accommodate the motion.

Today, the most common methods of repairing torn, severed or otherwise damaged tendons involve approximating the severed ends of the tendons and suturing one side of the tendon to the other thereby returning the tendon to its natural position. A popular suture technique is the so-called Kessler technique and slight modifications thereof. Some of the other techniques include the Becker, Savage, lateral trap, double loop locking suture, four-strand interlock and variations of the Halsted technique. Other methods place prosthetic material either within or around the tendon. Polyester strips and sleeves along with polyester mesh have been used to reinforce the suture/tendon interface to provide a stronger repair.

After flexor tendon repair, resistance to tendon gliding increases at the repair site. Repair techniques that use an increased number of suture strands, or increased amounts of suture material or prosthetic material promote greater glide resistance. In particular, adhesions form due to the tendon's natural response to healing, i.e., the ingrowth of cells and vessels from surrounding connective tissue. Current literature suggests adhesions may constitute an inflammatory process at the site of repair and an extension of the intrinsic tendon healing process to the surrounding tissue.

An ideal repair would exhibit high strength, flexibility, and a joining of the tendon ends without any foreign material on the outside surface of the tendon. Physical therapy should begin immediately after the repair to prevent the tendon from adhering to the tendon sheath creating adhesions that limit the full excursion of the tendon in its sheath. For this reason, the repair site must withstand the immediate tensile stress being applied to it during physical therapy. In a relaxed state, a flexor tendon experiences about one pound of constant tension. When a person applies a light grip, such as by grasping a key, about three to four pounds of tensile force is applied to the tendon. A strong grip can apply over ten pounds of tensile force to a tendon.

Since most suture-based tendon repairs reach their tensile limit at about 6 lbs., surgeons must balance the desire to have full and immediate active motion to prevent adhesions against the need for immobilization to prevent rupture of the repair. Earlier loading of a repaired tendon promotes a more rapid increase in repair strength. For a tendon to properly rejoin, the opposed tendon ends do not have to touch but they do need to be approximated within 1-2 mm of each other to properly reattach. An ideal tendon repair would hold the lacerated tendons together to begin healing and tissue generation but slowly release tension allowing the tendon to become the primary load bearing structure. Tendons will heal at a rate that is proportional to the load being applied during physical therapy.

Another major problem is the softening of the damaged tendon ends, which begins shortly after the damage or injury occurs and continues for approximately the next twelve days. This softening results in a weakening of the tendon fibers, which contributes to the formation of a gap at the repair site during the early phases of tendon healing. It is believed that gaps form at the site of repair due to a loss of purchase by the grasping portion of the suture at the tendon-suture interface. The grasping suture may even completely tear out, resulting in a failure of repair. A term for this failure is "rake-out". Rake-out is a failure mode associated with suture tendon repair in which the end of the severed tendon has weakened and the suture tends to pull out of the tendon ends. This splits the tendon and results in an undesirable gap or total failure. Another common type of suture repair failure is of a suture knot.

The effectiveness of a suture depends on many factors, such as the suture material, the technique with which the suture is inserted, and knot strength. Immediately after a tendon is repaired, the strength of the repair depends almost entirely on the suture technique. The ideal suture knot should terminate securely, be strong, easy to handle and inelastic. The suture material used today is generally braided polyester or a monofilament polypropylene. Using current suture techniques, absorbable suture materials do not have enough residual tensile strength over time to resist gapping and rupturing. The ideal suture technique should be easy to use, minimize interference with tendon vascularity and be completely internal to the tendon without increasing the bulk of the tendon. Locating the knots outside the tendon rather than within the repair site may result in higher ultimate tensile strength but will also increase the risk of adhesions and increase the friction through the pulleys. This latter characteristic is known as "work of flexion".

Most suture methods employ an internal suture with external knots distal and proximal to the laceration or within the laceration. The surgeon typically uses a continuous running external suture at the junction of the repair, known as an epitendinous suture, to approximate the tendon ends. The use of the epitendinous suture increases the tensile strength of the repair and helps to resist gapping, but it can also increase the risk of adhesions and is difficult to master and very tedious to execute. The evolution of tendon repair with sutures starts with the two-strand technique. Some of the variations of this technique are the Bunnell, Kessler, and Tsuge methods. When two-strand repairs fail, the failure usually occurs at the knots. Studies have shown that the initial strength of these repairs is proportional to the number of suture strands that cross the repair site. This has led to a trend of doubling, tripling, and even quadrupling the number of strands placed across the repair site. With these multiple strand techniques, Savage, Becker and Ketchum have shown significant tensile strength over the two-strand methods but they are more difficult to perform and add material to the outside surface of the tendon with more exposed knots. These techniques focus primarily on the increased effect on tensile strength and disregard the increased resistance to the tendon gliding through the pulleys. Therefore, the quest continues for the ideal suture technique having the tensile strength required to allow the patient to start physical therapy immediately, and having the low profile necessary to minimize adhesions that compromise the ability of the tendon to glide through the pulleys.

Techniques have also been developed that incorporate an internal or external prosthetic splint. Low porosity woven polyester, which is the same material used for aortic graft repair, is being used as an artificial splint. There are basically two methods of splint repair. The internal splint technique is accomplished by placing a horizontal slit transversely in each tendon stump proximal and distal to the laceration site. A rectangular piece of polyester splint is placed into this slit on both sides of the tendon. Sutures are then placed perpendicular to the graft along each tendon thereby attaching the splint to the tendon. The sutures attach the splint, which is basically a flexible tensile member, to the interior surface of the tendon. These suture knots are then tied on the outside of the tendon for ease of placement and an epitendinous suture is placed at the junction of the repair. As previously mentioned, the external knots will increase the risk for adhesions and also increase the work of flexion. The material of the tendon splint is inert and similar to the suture material being used in other techniques and its internal position within the substance of the tendon should promote tissue ingrowth and enhance the repair site. However, the large slits in the tendon ends might structurally damage the internal blood supply of the tendon and cause tissue degeneration.

In the external splint technique, also known as the dorsal tendon splint technique, the surgeon aligns both tendon ends and places a two-strand Savage type core suture on the anterior surface of the tendon. The surgeon then places a rectangular Dacron® splint on the dorsal surface of the tendon across the laceration site and sutures it to both tendon ends. In this technique, and as mentioned earlier, the splint acts as a flexible tensile member that prevents the tendons from gapping and rupturing during early movement. As with the internal method, the knots are placed on the exterior surface of the tendons and the splint is actually on the outside surface. This will increase the risk of adhesions and consequently increase the work of flexion. The internal tendon splint may add too much bulk to the repair site, and the external tendon splint may interfere with tendon gliding. Preliminary work of flexion studies suggest both tendon splints increase the work of flexion by 16-19%.

Another splint-type technique being used today is a Dacron® or Prolene® mesh sleeve that surrounds the tendons. The two ends of the lacerated tendons are placed in the proximal and distal openings of the sleeve. The tendon ends are butted together without any additional sutures, except that an epitendinous suture is placed thereby attaching the sleeve to the outside surfaces of the tendons. This is done on both ends of the sleeve. This technique is 117% stronger in tension than a conventional two-strand core stitch technique with an epitendinous suture on the external surface. Like the aforementioned splint techniques, these are tested in vitro (outside of the body) and do not take into account any of the in vivo (inside the body) problems that occur such as placing a significant amount of repair material external to the tendon and within the tendon sheath. Again, external repair material provides a potential source of fibrous adhesions and an increase in work of flexion.

Implanted anchors have also been used to attach two ends of a severed tendon. This type of anchor is similar to a Dacron® splint in concept but is usually fabricated from stainless steel or titanium. The geometry of the anchor also differentiates the anchor from a splint. The anchor, which may measure 20 mm in length, 3 mm in width and 1 mm in thickness, has a symmetrical double barbed end configuration. The anchor is placed into the severed end of the tendon by making a small transverse incision. Once the anchor is in the correct depth the surgeon will place a suture through the tendon at the flat side of the barb and knot the suture into a loop thereby preventing the barb from being pulled out of the tendon. The tendon will be sutured at each flat on the barb, providing two suture loops per tendon end. The same suture technique is performed on both ends thereby re-attaching the severed tendon. This repair technique shows an increase in mean ultimate tensile strength of 49-240% over traditional two-strand and multi-strand suture techniques. This technique is relatively easy to perform but it does not address the in vivo problems caused by placing the suture knots on the outside of the tendon. Here, they become a potential source of fibrous adhesions and increase the work of flexion. This type of tendon anchor can limit motion or cause pain when positioned directly over a joint with the finger in maximal flexion since it is long and fairly rigid. Also, the surgeon must still bring the tendon ends together with a separate surgical tool and, in the process, risk damaging the tendon ends.

Adhesives have been evaluated in the search for the ideal tendon repair. Studies have been conducted using adhesives of the cyanoacrylate group, more commonly known as super glues. These adhesives form a strong adhesive bond with most human tissue, particularly those containing a large amount of protein, such as skin and tendon tissue, because they polymerize in the presence of water and hydroxyl groups, both of which are abundantly present in tendon tissue, and they do not require a solvent. They are known to be biodegradable, although the time taken to degrade in tendons is unknown and only the long chain varieties are known to be minimally toxic to human tissue. The application of adhesives in tendon repair is in conjunction with two-strand or multi-strand core suture with an epitendinous suture. The adhesive is placed on the tendon ends after the sutures have been placed and approximated to allow for polymerization. The shortcomings that were discussed in connection with suture repair are experienced with adhesive techniques as well. Some problems with adhesives include their potential non-biodegradability within the tendon, their questionable effect on tendon healing, and their potential local and systemic toxicity. Currently, therefore, adhesives do not provide an adequate solution to tendon repair problems.

Current and past tendon or ligament repair techniques concentrate on increasing the tensile strength of the repair by adding more structural components to the repair, e.g., sleeves, splints, additional suture strands, additional knots and adhesive. All of these techniques trade off between early tensile strength, increased work of flexion, and increased risk of adhesions or other problems. While the surgeon debates the clinical technique, the patient may suffer from a less than desirable outcome and discomfort over the life of the repair. Adhesions cause pain and limit motion of the affected joints. By increasing bulk to the tendon, motion may be further limited and this can result in a defect called "trigger finger."

None of these techniques have utilized the physiological makeup of the tendon to provide a stronger repair. The tensile strength of the tendon is provided by the lengthwise parallel collagen fibers, which give it the ability to withstand high tensile loads. The ground substance is made up primarily of water and cannot be used to provide strength to the repair. The tendon sheath is also too weak to provide meaningful assistance with holding the two tendon ends together.

Similar problems arise when attaching tendons or ligaments to bone. That is, simply suturing the tendon or ligament to a bone anchor or using external tendon anchor members may not provide the necessary strength of repair. As further discussed above, these techniques also promote adhesion formation.

Finally, tendon retrieval has also been a problematic portion of tendon repair surgery. Typically, the surgeon must use a small grasping tool with thin, movable jaws similar to needle-nose pliers to grasp a tendon end and pull and transfix it in an appropriate operating position. Unfortunately, gripping the tendon ends in this manner often damages them and makes the tissue less able to hold the epitendinous suture. The damaged tendon ends will also form scar tissue or adhesions which further adversely affect the repair.

Therefore, there is a need for tendon repair techniques and apparatus that harness the intrinsic strength of the tendon fibers, but allow the tendon to flex while moving through the sheath. This repair apparatus should resist any gapping or rupture during immediate post-operative physical therapy, and reside in the interior of the tendon to reduce or possibly eliminate post-operative adhesions. The repair apparatus should also produce low work of flexion while gliding unhindered through the tendon sheaths. There is generally a need for tendon repair apparatus and methods that allow the patient to immediately begin active physical therapy without risking any tendon repair failure while minimizing or eliminating the need for sutures or other repair structure on the external surfaces of the tendon thereby reducing the occurrence of adhesions and friction between the tendon repair and the sheath pulley. There is a further need for tendon-to-bone repair techniques and apparatus with at least some of these attributes. Finally, there is a need for a tendon retrieval device which also harnesses the inherent strength of the tendon fibers and minimizes damage to the retrieved tendon end.

SUMMARY OF THE INVENTION

The present invention generally provides apparatus for repairing damaged tendons or ligaments. The various repair apparatus according to the invention employ an elongate tensile member adapted to extend within the interior of the tendon or ligament and various types of anchor structures configured for insertion within the interior of the tendon or ligament. The anchor structures are both movable along and lockable to the elongate tensile member at a selected position. As some examples, these anchor structures may comprise helical anchors with separately connectable tendon fiber retaining members, unitary helical anchor/tendon fiber retaining member assemblies, compressible helical anchors, anchor bodies secured inside the tendon with sutures or projections such as barbs, and crimp-type anchor members that grip tendon fibers between two crimp portions or members, as well as other configurations. Various embodiments of repair apparatus are disclosed herein each serving to address the general needs and drawbacks presented by the prior art as discussed above.

Among the various advantages and objectives of this invention, apparatus comprising at least one tendon or ligament anchor structure in combination with an elongate tensile member are provided and utilize the inherent strength of the bundles of parallel collagen fibers in tendons or ligaments. Repair techniques are provided that address the tensile component of the repair and eliminate the increase of bulk to the tendon or ligament. This is accomplished while reducing externally placed components that compromise the ability of the tendon to glide through the pulleys. Through an understanding and utilization of the inherent strength provided by the bundles of parallel collagen fibers, the inventors have developed anchor structures that grasp these high strength fibers without constricting the blood flow to the tendon, and without adding external bulk or additional knots. The anchor systems of this invention further allow the patient to begin immediate active motion physical therapy resulting in a quicker and stronger tendon repair with fewer adhesions. Also, the combined anchor structure and elongate tensile member of this invention provide a tendon or ligament repair that can withstand greater tensile loads than current and past repair techniques while retaining the repaired tendon or ligament ends in a viable repair position.

Generally stated, the present invention comprises at least one anchor structure coupled for movement along the length of an elongate tensile member. The anchor structure is lockable at a desired location along the tensile member and generally includes first and second fiber gripping portions configured for insertion within the interior of a tendon or ligament. The gripping portions may be on two separate components of the anchor structure or may be portions of the same component. In several embodiments of the invention, at least one of the fiber gripping portions is movable with respect to the other to grip the fibers therebetween. Many different configurations of anchor structures are disclosed herein including single-piece anchor structures and multi-piece anchor structures. In the single-piece anchor structures, one portion of a member, such as a crimp member, is movable toward another portion of the member to grip tendon fibers therebetween. In other embodiments, separate pieces of the anchor structure are brought together and locked to grip, engage or compress the tendon fibers therebetween. In the most preferred embodiments, two anchor structures are each initially movable along the length of the elongate tensile member on opposite sides of a torn, lacerated or otherwise damaged portion of the tendon. The anchor structures may be locked to the fibers within the tendon and to the elongate tensile member itself when the tendon is at the proper repair position. Various more specific embodiments of the anchor structures and elongate tensile members of this invention are described hereinbelow.

In one embodiment of the invention, an anchor body in the form of at least one helical anchor is configured for insertion within the interior of the tendon or ligament. At least one retaining member is coupled with the elongate tensile member and provides a securing structure to hold the helical anchor to the fibers extending within the interior of the tendon or ligament. In a preferred apparatus of this type, first and second helical anchors are provided with respective first and second retaining members each being couplable for movement along the elongate tensile member on opposite sides of a repair site. The retaining members may each include, for example, an axial hole to allow this movement. Optionally, a lengthwise slot may be provided in the retaining member. In this embodiment, and the other embodiments of the invention, the elongate tensile member may comprise a rigid, semi-rigid or flexible member, including flexible sutures formed from absorbable or non-absorbable materials, as well as tensile members formed from various biocompatible metals, plastics, ceramics, etc. The helical anchor preferably comprises a helically wound coil which may be of constant or variable diameter and may be formed of biocompatible metal. Optionally, the coil may be formed from absorbable material or other non-absorbable biocompatible materials. The retaining member is preferably configured to be received within a corresponding helical anchor for compressing the fibers between the retaining member and the helical anchor. When the helical anchor is rotated into the tendon or ligament, fibers of the tendon or ligament will be captured within the coils of the anchor. When the retaining member is then inserted and affixed within the helical anchor, the outer surface of the retaining member compresses the fibers against inner surfaces of the helical coils. Preferably, locking structure in the form of at least one locking member is used for holding the retaining member to the elongate tensile member at a desired position. This locking member may be a separate slidably adjustable member or an integral portion of the corresponding retaining member and may, for example, comprise a deformable or crimpable portion of the retaining member or a separate crimp member.

The retaining member or members preferably have associated retaining structure either integrated therein or used as separate structure for gripping the tendon fibers against the helical anchor. For example, the retaining structure may comprise a discontinuous surface adapted to aid in holding the fibers between the retaining member and the helical anchor. As examples, this discontinuous surface may be an exterior serrated surface, a generally threaded surface, or another type of convoluted or discontinuous surface. This surface may also serve to prevent the retaining member from backing out of the helical anchor.

As another feature, the elongate tensile member and the respective retaining member or members may include respective engageable portions, such as ratchet-like portions, for holding the retaining member at the desired position along the elongate tensile member.

As still another feature, at least one of the elongate tensile member, the first helical anchor and the retaining member may be comprised of an absorbable material. During the absorption process, this will allow a gradual transfer of tensile load to the repair site to aid in healing. More generally stated, at least one component of the anchor system will be made from an absorbable material, such as polyglycolic acid or polyglyconate. This will allow for the tensile stress of the anchor system to be gradually transferred from the anchor system to the tendon during the healing of the tendon repair site. As revealed previously, the healing response of the tendon is directly proportional to the amount of tension being applied to the tendon. In other words, more tension on the tendon results in a stronger repair. However, the initial condition of the repaired tendon does not withstand any tensile load. Therefore, a timed release of the tension being applied to the tendon will result in a stronger repair. By making a key component or components from an absorbable material, the repair apparatus slowly transfers tension to the tendon until the component(s) completely degrade and releases all the tension to the tendon repair site.

As an additional feature of the invention, the retaining members may include structure configured to directly engage the helical anchor to prevent the retaining members from backing out of the helical anchors after implantation. As one example, this may include ratchet-type structure on the retaining member adapted to engage the trailing end of the helical anchor.

The retaining members of the various embodiments of this invention may also have various configurations. One configuration is a helical retaining member. In this case, the helical anchor will be either received within the helical retaining member or may receive the helical retaining member. Either construction forms inner and outer helical members. This is helpful because the helical members will compress tendon or ligament fibers therebetween in a generally sinusoidal pattern. At least one of the inner and outer helical members is collapsed or expanded toward the other to clamp or compress the tendon or ligament fibers therebetween. This may be accomplished, for example, through mechanical spring action of the helical members during insertion or through the use of electromagnetic impulse deformation. In the latter case, and as detailed further below, one helical member may be formed of a magnetic material while the other is not. Upon the application of one or more impulses of electromagnetic energy, the magnetic helical member will collapse onto the nonmagnetic helical member compressing the tendon fibers therebetween.

As another option, the helical anchor of this invention may be formed from a flexible suture material. In this case, the retaining member is adapted to be inserted into the tendon or ligament and the flexible suture material is then wrapped generally helically about the retaining member to hold the tendon or ligament fibers therebetween. As the flexible suture material which is wrapped around the retaining member is not held in significant tension, it may be formed of material having lower tensile strength than the elongate tensile member.

In another embodiment of the invention, the apparatus may comprise first and second helical anchors integrally formed from a wire with the elongate tensile member extending therebetween. In this embodiment, the anchors are helically wound in opposite directions such that rotation of the integral apparatus in a single direction, with the elongate tensile member disposed generally between the damaged or severed tendon ends, will cause rotation of each respective helical member into a respective tendon end. Retaining members in accordance with the invention may then be used to grip, compress or otherwise engage the tendon fibers to the helical anchors.

In yet another embodiment of the invention, the apparatus may include a helically coiled, compressible anchor configured for insertion within the interior of the tendon or ligament and couplable with the elongate tensile member. This compressible anchor traps the fibers of the tendon or ligament between the coils as its coils are moved from their uncompressed state to their compressed state. As with the other embodiments of this invention, the apparatus preferably includes a second anchor structure in the form of another helically coiled, compressible anchor which is also couplable to the elongate tensile member. It should also be noted that the elongate tensile member of this invention may be formed by two or more separate tensile members, such as sutures, which are then tied or otherwise directly or indirectly affixed together during the repair procedure such that a unitary elongate tensile member is formed connecting at least two anchors together to hold the tendon or ligament in an approximated repair position. In other words, the elongate tensile member may be formed from a number of different segments or portions which are ultimately secured together and secured to the anchor structures. In the embodiment employing compressible anchors, these anchors are also preferably coupled for movement along the elongate tensile member and include respective locking members, preferably slidably coupled to the elongate tensile member, and adapted to hold the compressible anchors at desired locations on the elongate tensile member. The locking members may be, for example, formed as crimp members or other structures formed integrally or separately from the corresponding compressible anchor.

The retaining members of this invention may also be slotted members. In a general sense, this allows the retaining member to be coupled to the elongate tensile member without necessarily using a sliding motion along the tensile member as with a retaining member that includes an axial hole. The slot or slots may further act as a collet structure configured to clamp onto the elongate tensile member upon insertion into the helical anchor or through the use of a separate tool. In another advantageous embodiment of a collet structure, the retaining member may be a two-piece slotted collet structure with an interior piece and an exterior piece. Upon insertion of the exterior piece into the helical anchor and the interior piece into the exterior piece, the interior piece is configured to clamp onto the elongate tensile member and the exterior piece is configured to expand within the helical anchor to compress the fibers against the helical anchor.

In yet another embodiment, the elongate tensile member will be locked to the helical anchor by trapping the elongate tensile member between the internal retaining member and the helical anchor. This will eliminate the need to have a locking feature built into the internal retaining member in order to lock the elongate tensile member to the helical anchor.

In yet another embodiment, the tendon repair apparatus has multiple helical anchors. In this embodiment, there is more than one helical anchor placed within the tendon. The helical anchors may be wound in opposite directions and/or intertwined together. This configuration is based on the aforementioned method of grasping parallel collagen fibers. An advantage to multiple anchors is that the amount of collagen fibers being trapped is directly proportional to the amount of coils on the helical anchor. Increasing the length and the number of coils of the helical anchor likewise increases the amount of trapped collagen fiber. Since there are limitations to the length of the anchor, an additional anchor of the same length is placed in the tendon.

Another more specific anchor structure of this invention utilizes a crimp-type anchor member. In this embodiment, one of the fiber gripping portions further comprises at least one first deformable portion adapted to be crimped within the tendon or ligament to grip the fibers. In one specific embodiment, the crimp member will have opposed legs that may be deformed toward one another and onto the tendon fibers. The crimp member may further include a second deformable portion configured to be crimped onto the elongate tensile member to retain the crimp member at a desired location thereon. In a related embodiment, the anchor structure may further comprise first and second separate crimp members adapted to be crimped onto the fibers generally from opposite sides of the elongate tensile member. The first and second crimp members can each include a respective plurality of deformable legs configured to interlock after crimping to securely hold the first and second crimp members to the tendon fibers. The first and second crimp members can further include respective crimp portions configured to be crimped onto the elongate tensile member to retain the first and second crimp members at a desired location along the length of the tensile member. As one other alternative, a separate locking member may be used to retain the first and second crimp members at a desired position along the length of the elongate tensile member.

In another aspect, the anchor structures further comprise first and second anchor bodies with respective first and second securing structures. These securing structures may, for example, comprise projections extending respectively from the first and second anchor bodies that retain the anchor bodies within the tendon or ligament. The anchor bodies may be tubular-shaped members or members having various other shapes configured for insertion within the tendon or ligament. As another alternative or additional securing structure, the anchor bodies may include portions for receiving sutures used to secure the first and second anchor bodies within the interior of the tendon or ligament. As with the previous embodiments, the locking structure can, for example, include a crimpable or swageable member or an integral portion of an anchor body operable to affix the anchor body onto the elongate tensile member. In many of the embodiments of this invention, two anchor bodies are each initially connected for movement along the elongate tensile member and first and second respective locking structures or members are used to lock each anchor body to the elongate tensile member with the tendon or ligament in a desired repair position.

As a further aspect, the invention provides apparatus for affixing a tendon or ligament to a bone. In this embodiment, the apparatus includes an elongate tensile member, a tendon or ligament anchor structure constructed in accordance with any of the anchor structures of this invention, and a bone anchor. The elongate tensile member, for example, may be a flexible suture adapted to extend within the interior of the tendon or ligament. The bone anchor is coupled with the elongate tensile member and is configured to be retained within the bone. As a more specific feature of the preferred embodiment of this invention, the tendon or ligament anchor may be a helical anchor as generally described above and may be compressible. A retaining member is adapted to be retained at a selected position along the elongate tensile member to hold the bone anchor, elongate tensile member and helical anchor together with the tendon or ligament against the bone. The retaining member and the bone anchor may include cooperating locking portions for connecting the retaining member and bone anchor together with the helical anchor held generally therebetween. Alternatively, or in addition, the retaining member may be sized and configured to be received at least partially within the helical anchor and a locking member, such as a crimp, may be coupled with the elongate tensile member to hold the retaining member at a desired position. As with the other embodiments of this invention, the locking member may be, for example, a deformable and slidable crimp member either separately formed or integrally formed with the retaining member.

In another aspect of the present invention, a tendon or ligament retrieval device is provided and operates to move a tendon or ligament end to a desired operating position. The device generally comprises an elongate body, a helical member coupled with the elongate body and at least one drive mechanism coupled with the helical member for effecting rotational movement of the helical member into the tendon or ligament and subsequent translational movement of the helical member to move the tendon or ligament to the desired operating position. To facilitate this function, the helical member is mounted for rotational and translational movement relative to the elongate body. The elongate body is adapted to be inserted into a tendon sheath, for example, and is preferably flexible to allow manipulation therein by the surgeon. The elongate body may also include a distal tip with anti-rotation structure for engaging the tendon or ligament end and preventing rotation thereof as the helical member rotates into the tendon or ligament end. As one optional anti-rotation feature, the helical member may further include first and second, counter-rotating helical grasping bodies each being connected for rotation and translation by the drive mechanism.

Various methods are also contemplated in accordance with the invention relative to tendon or ligament repair. A representative method involves installing an elongate tensile member within the tendon or ligament and driving a first helical member into the tendon or ligament. The first helical anchor is secured to the elongate tensile member and a second helical anchor is driven into the tendon or ligament. The tendon or ligament is then moved to a repair position at least prior to securing the second helical anchor to the elongate tensile member whereupon the second helical anchor is then securely fastened to the elongate tensile member to hold the tendon or ligament in the repair position. The various tendon or ligament anchor structures disclosed herein may be used for carrying out the repair methods and additional repair methods will become more apparent upon review of the detailed description of this invention.

In another embodiment of the invention, a helical anchor is coupled to a tendon fiber retaining member to form a unitary anchor assembly. The anchor and attached retaining member are driven into the tendon or ligament at one time. This aspect of the invention further includes an insertion tool for driving the assembly into the tendon or ligament preferably with a simultaneous rotating and translating movement. More specifically, the anchor assembly comprises a core portion or retaining member positioned inside of a helical anchor with the distal end of the anchor preferably being tapered or sharpened to ease insertion and also extending distally outward of a distal end of the retaining member. The distal end of the retaining member may also be tapered and the outer surface can include a helical groove or generally helically configured surface which generally corresponds with the helical anchor. At the proximal end of the retaining member, a slot is provided and the proximal end of the anchor resides in the slot and is secured in a suitable manner, such as through laser or resistance welding. The extreme proximal end of the core portion or retaining member includes tool engagement structure, such as a slot, which allows the insertion tool to be used to rotate and translate the assembly into the tendon or ligament. The core portion or retaining member includes a central bore through which the elongate tensile member extends and, in the preferred manner of making and using this embodiment, a separate crimp member is secured to the tensile member at the proximal end of the core portion or retaining member. However, integral crimp members or other types of locking members may be used instead. The separate crimp member of this embodiment has an annular groove in its outer surface to reduce the force necessary to collapse the crimp on the elongate tensile member.

A unique crimp tool is provided with a jaw configuration which both collapses the crimp, when desired, and which retains the crimp between the jaws prior to use, such as during packaging, shipping, and storage. For this latter purpose as well, a flexible or frangible bar is coupled between two handles of the crimp tool and aids in holding the jaws in a closed position to retain the crimp therein prior to use, but also prevent the jaws from moving together and prematurely collapsing the crimp until necessary during surgery. The bar or bars may be formed of a suitable material, such as plastic, which will bend or fracture during use. The jaws also include a projection on one jaw and a recess in an opposing jaw for receiving the crimp member. During use, the projection is forced against the crimp member to collapse the crimp member against the tensile member. The recess includes a ridge for registering in the annular groove of the crimp member and thereby assisting to hold the crimp member therein.

The method of using the unitary anchor assembly generally corresponds to the broader aspects of the methods disclosed herein. In a more specific and preferred method of using the embodiment of this invention which comprises a unitary helical anchor and tendon fiber retaining member, an anchor assembly is driven into the tendon or ligament on each side of the damaged or lacerated area. An elongate tensile member having a needle at one end and a preset crimp member at an opposite end is then threaded through the proximal end of a first one of the anchor assemblies and into the space between the ends of the damaged tendon or ligament. A second capturing member, such as a vena-puncture or syringe needle is then inserted through the proximal end of the second anchor assembly and into the space between the damaged or lacerated tendon or ligament ends. The needle coupled to the elongate tensile member is then captured, such as by inserting its end into the syringe needle, and the elongate tensile member is pulled through the second anchor assembly. A crimp member is then threaded onto the elongate tensile member to a position abutting the proximal end of the second anchor assembly and the tendon or ligament ends are pulled together to the desired position. The crimp member is then deformed or collapsed onto the tensile member to fix the tensile member and two anchor assemblies at the desired length. The excess length of the tensile member is then cut at the proximal end of the second anchor assembly and any necessary additional closing procedures are performed by the surgeon.

As one additional aspect of the invention, a removal tool is provided which is especially useful for the latter embodiment and comprises a rotatable tool having a pointed needle projecting from a tool driver head. The tool driver head is configured to engage the tool engagement structure on the proximal end of the unitary anchor assembly and, in the preferred embodiment, comprises a generally conventionally-shaped screwdriver projection complementary to a slot in the proximal end of the anchor assembly. It will be understood that many types of tool engagement structure may be used for this purpose.

Various additional features, advantages and objectives of the invention will become more readily apparent to those of ordinary skill in the art upon review of the following detailed description of the preferred embodiments, taken in conjunction with the accompanying drawings.

BRIEF DESCRIPTION OF THE DRAWINGS

FIG. 7 is a top view of a third embodiment of a button to be used with the bone repair device of the present invention;

FIG. 8 is a side view of a third embodiment of a button to be used with the bone repair device of the present invention;

FIG. 9 is a sectional view of the third embodiment of a button to be used with the bone repair device of the present invention being attached to a suture;

FIG. 10 is a sectional view of a fourth embodiment of a button to be used with the bone repair device of the present invention being attached to a suture;

FIG. 11 is a perspective view of the bone repair device of the present invention being used to repair a torn or fractured meniscus;

FIG. 12 is a top view of the incisions made in a hand in the prior art to repair a torn tendon;

FIG. 15A is a cross-sectional view of a first embodiment of a button as shown in FIG. 15;

FIG. 15B is a cross-sectional view of a second embodiment of a button as shown in FIG. 15;

FIG. 15C is a cross-sectional view of a third embodiment of a button as shown in FIG. 15;

FIG. 15D is a cross-sectional view of a Fourth embodiment of a button as shown in FIG. 15;

FIG. 16 is a sectional view of a repaired tendon using a first embodiment of a button in accordance with the present invention;

FIG. 16A is a sectional view of a revised stitching procedure in accordance with the invention of FIG. 15;

FIG. 17 is a sectional view of a repaired tendon using a second embodiment of a button in accordance with the present invention;

FIG. 17A is a sectional view of a second embodiment of a button in accordance with the present invention being swaged to a suture;

FIG. 17B is a top view of a second embodiment of a button in accordance with the present invention;

FIG. 28 is a top view similar to FIG. 27, but isolating the finger to be repaired and showing transfixation of the tendon segments;

FIG. 29 is a perspective, schematic view showing initial steps in a tendon repair procedure in accordance with the invention;

FIG. 30 is an enlarged perspective view of the distal end of the tool shown in FIG. 29, illustrating the attachment of a helical anchor in accordance with the invention;

FIG. 31 is a perspective view showing the insertion of the helical anchor within a tendon segment;

FIG. 31A is a partially cross sectioned, perspective view illustrating a modified form of the anchor insertion tool shown in FIGS. 29-31;

FIG. 32 is a perspective view similar to FIG. 31, but showing the subsequent insertion of a retaining member into the tendon segment;

FIG. 40 is a schematic, sectional view showing an alternative configuration of a helical anchor;

FIG. 41 is a schematic, sectional view of another alternative helical anchor;

FIG. 42 is a schematic, sectional view of another alternative helical anchor;

FIG. 43 is a partially sectioned view of another alternative repair apparatus connected within a tendon;

FIG. 44A is a partially sectioned view of another alternative repair apparatus in accordance with the invention;

FIG. 44B is a partially sectioned view similar to FIG. 44A, but showing the partial absorption of the retaining member of this embodiment;

FIG. 45A is a partially sectioned view showing another alternative embodiment of a repair apparatus in accordance with the invention;

FIG. 45B is a partially sectioned view similar to FIG. 45A, but showing partial absorption of the various components of the apparatus;

FIG. 45C is a partially sectioned view similar to FIG. 45B, but illustrating full absorption of the helical anchor and internal retaining member and partial absorption of the elongate tensile member;

FIG. 79 is an enlarged cross sectional view of the tool being used to drive the unitary anchor assembly into a tendon or ligament;

FIG. 80 is a side elevational view schematically showing an alternative pistol grip assembly for the insertion tool of FIG. 77 allowing one-handed operation by a surgeon;

FIG. 80A is a fragmented end view of the pistol grip assembly of FIG. 80 schematically illustrating the interaction between the rack and pinion drive;

DETAILED DESCRIPTION OF THE PREFERRED EMBODIMENTS

Bone and Meniscus Repair Device

Figure 1:
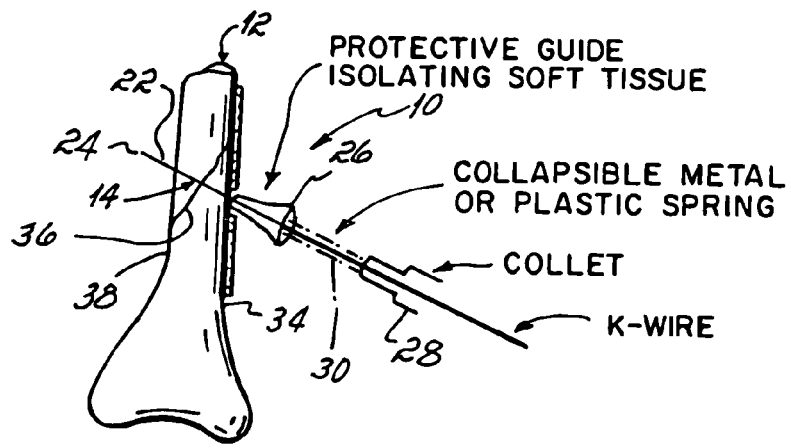
FIG. 1 is a perspective sectional view of the bone repair device according to the present invention.

As shown in FIGS. 1-10, a novel device 10 for repairing a fractured bone 12 is shown. The fractured bone repair device 10 has three primary parts, a flexible or rigid suture or filament 14, a first button 16, and a second button 18. First button 16 is ideally identical to second button 18. The suture or filament may be rigid or flexible, monofilament or multifilament.

Figure 2:
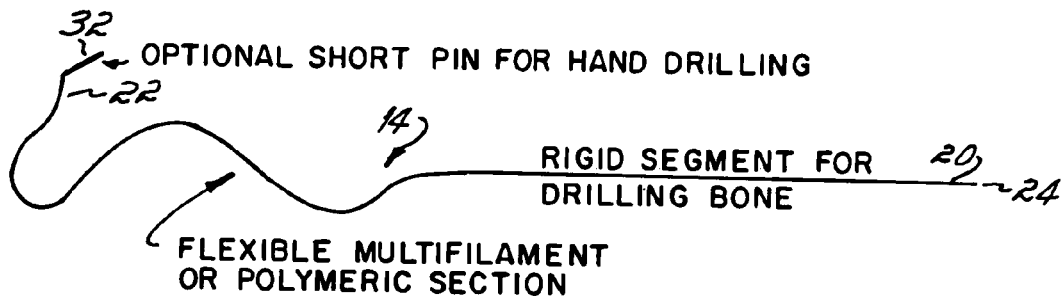
FIG. 2 is a side view of the suture to be used with the bone repair device according to the present invention.
Figure 3:
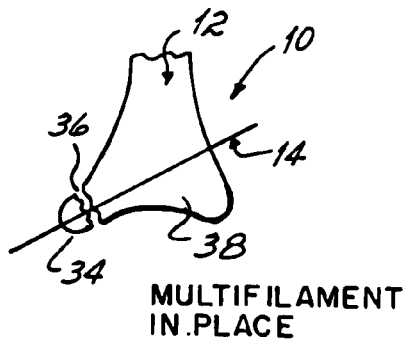
FIG. 3 is a sectional view of the suture in place in a bone to be repaired in accordance with the present invention.
Figure 4:
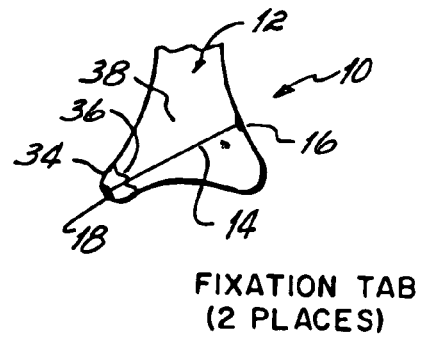
FIG. 4 is a sectional view of a fractured bone repaired with the bone repair device according to the present invention.

As shown most particularly in FIG. 2, suture 14 has a first end 20 and a second end 22. First end 20 of suture 22 is made rigid so as to allow the suture to be drilled through a fractured bone 12, as shown in FIG. 1. The rigid segment 20 is placed in a standard driver (not shown) which is well-known to one of ordinary skill in the art, most preferably a MicroAire Wire Driver. The rigid segment 20 ideally has a sharp point 24 to allow for easier drilling.

A sheath 26 may also be provided for the filament 14 during the drilling procedure and forms a part of this invention. The sheath 26 would serve as an extension from the collet 28 of any of the well-known drilling tools. Two forms are contemplated. The first would use a collapsing sheath (not shown), such as an accordion pleat such that the sheath will buckle as the tool moves towards the bone 12. alternatively, a concentric spring 30 may be made of any of a variety of materials. The material must be strong enough to withstand any punctures from small bone fragments which may be displaced through the drilling procedure. However, it must be thin enough to allow its collapse as drilling progresses. The material must also have sufficient heat resistance or a sufficiently high melting point that it is unaffected by the heat generated by the drill. The sheath 16 will extend the full length of the drilling tool from the collet 28 to fully protect surrounding tissues.

Optionally a short pin is located on the second end 22 of the suture 14. This pin 32 may be used for hand drilling the bone 12. whether the bone 12 must be hand-drilled or may be drilled by machine is based on a number of factors, all of which are well-known by these of ordinary skill in the art. The filament may alternately be passed through a pre-drilled hole in the bone 12.

Regardless of how the bone 12 is drilled, the method of operation of the bone repair device 10 is the same. The rigid second end 22 is drilled from a first side 34 of a fracture 36 to a second side 38 of fracture 36. The rigid second end 22 is then pulled such that the suture portion 14 is within the bone 12. The purpose of the suture 14 being optionally flexible is that many bones which are fractured are small in size and are not easily aligned. In order to properly repair a bone, most particularly a small bone, using prior art technology, a practitioner must spend a large amount of time precisely aligning the first side 34 and second side 38 of fracture 36. If the suture used is flexible, the first side 34 and second side 38 need not be precisely aligned, since the flexible suture 14 can bend at any point. While it is desirable that first side 34 and second side 38 be somewhat aligned, it is not necessary to have as great a precision and much time can be saved.

The suture 14 is preferably a monofilament or multifilament wire or flexible polymer. The thickness of suture 14 depends on the size and location of the bone but, for small bones such as are in the hand, will fall within the range of 0.02 to 0.06 inches in diameter. The differing tensile strengths which will be needed for various bones and the tensile strengths of various thicknesses are well-known to one of ordinary skill in the art.

Once the suture 14 has been drilled through bone 12, or passed through a pre-drilled hole, it extends completely through bone 12 from the first side 34 of fracture 36 to the second side 38 of fracture 36. The suture 14 must then be secured in order to hold the first side 34 and second side 38 together until fracture 36 is healed. The suture is secured on each side 34, 36 by a button 16, 18. Because each button 16, 18 is selected from the same group of possible designs, the designs are described only in reference to first button 16. However, it will be understood that second button 18 may have a similar design.

Figure 5:
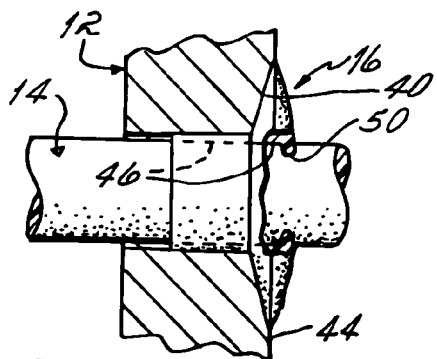
FIG. 5 is a sectional view of a first embodiment of a button to be used with the bone repair device of the present invention.
Figure 6:
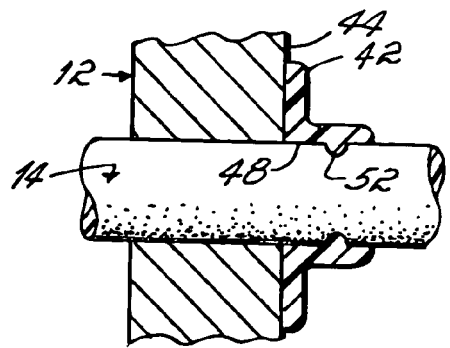
FIG. 6 is a sectional view of a second embodiment of a button to be used with the bone repair device of the present invention.

As is most clearly shown in FIGS. 5 and 6, two types of buttons 16 are preferred. FIG. 5 shows a button 16 which includes a flange 40 which extends to or beneath the surface 44 of bone 12. FIG. 6 shows a button 16 which includes a flange 42 resting on the surface 44 of bone 12.

Flanges 40, 42 serve to aid in distributing the tension load from the suture 14. Each button 16 has an inner surface 46, 48 which slidably contacts and circumscribes suture 14. On the inner surfaces 46, 48 of the buttons 16 is one or more notches 50, 52. Notch 50 is formed such that it is an extension of flange 40, whereas notch 52 is formed separately of flange 42. Because suture 14 is flexible and somewhat soft, compared to buttons 16, a crimping tool (not shown) may be used to press inwardly on or crimp button 16 such that notches 50, 52 penetrate suture 14 and become secured to suture 14. In this way, the buttons 16, 18 may become attached to suture 14.

An alternative button 16 is shown in FIGS. 7-10. This button 16 is a locking spring washer. With such a button 16, the tension on the suture 14 may be increased, but not decreased. This type of button 16 locks by itself with no crimping tool required. The suture 14 ideally includes notches or grooves 54 to aid in the attachment of button 16 to suture 14.

This method if ideally designed for use with bones in the hands or feet which are smaller and more delicate. However, the same invention may be used in connection with larger bones and may be particularly useful if a larger bone is broken into many smaller pieces. The diameter of the rigid segment, filament, and pin must be adjusted to effectively join the bone and fragment, especially if the bone and fragment are large.

Turning to FIG. 11, the same invention may also be used to repair a torn meniscus 56. The suture 14 (shown in dashed lines) is threaded through the meniscus 56 from a first side 58 to a second side 60 of fracture or gear 62. While a meniscus 56 is typically referred to as being torn rather than fractured, the word "fracture" and all forms thereof should be understood to refer to both bones and to menisci in the context of this invention for ease of understanding and vocabulary and to avoid confusion with the invention (described below) which relates to the repair of torn tendons. A first button 16 is attached to and circumscribes suture 14 on a first side 58 of the fracture 62 and a second button 18 is attached to and circumscribes suture 14 on a second side 60 of fracture 62. Buttons 16, 18 may have the same configuration as those described above or may resemble the tabs 144 as described in tendon repair, FIG. 17B.

Tendon Repair Device and Method

The method described may be used with any of the relevant buttons in the present invention. The prior art method for repairing a torn tendon is shown in FIG. 12, and involves making a single long incision over the location of the torn tendon. The present invention (shown in FIG. 13) uses a device and method for repairing a torn tendon through one or more skin incisions and two or more smaller incisions in the sheath, minimizing trauma to critical tissues. This invention may be used to repair either a tendon or a ligament. The term "tendon" as used in the application should be understood to also encompass ligaments.

Figure 13:
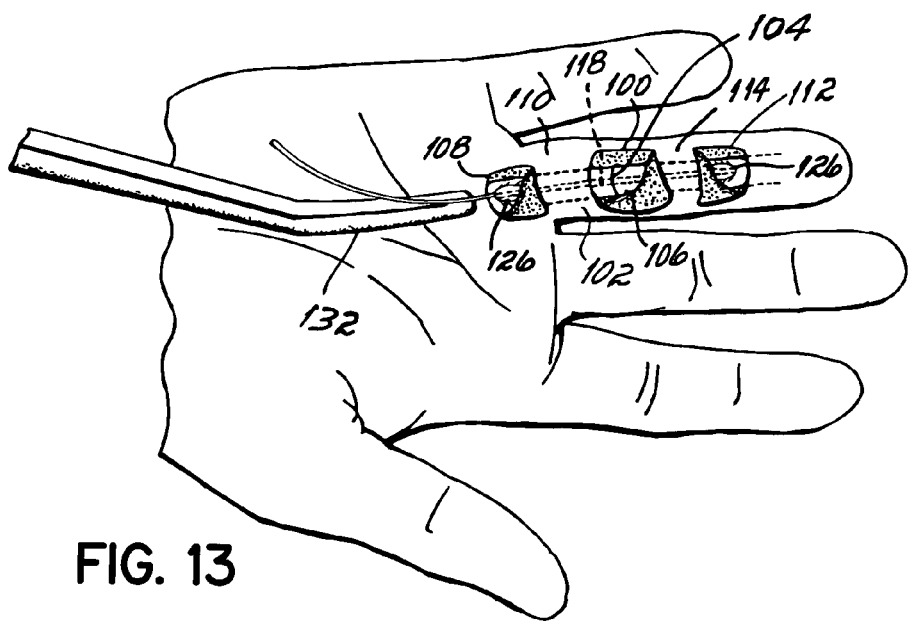
FIG. 13 is a top view of the incisions made in accordance with the present invention to repair a torn tendon.
Figure 14:
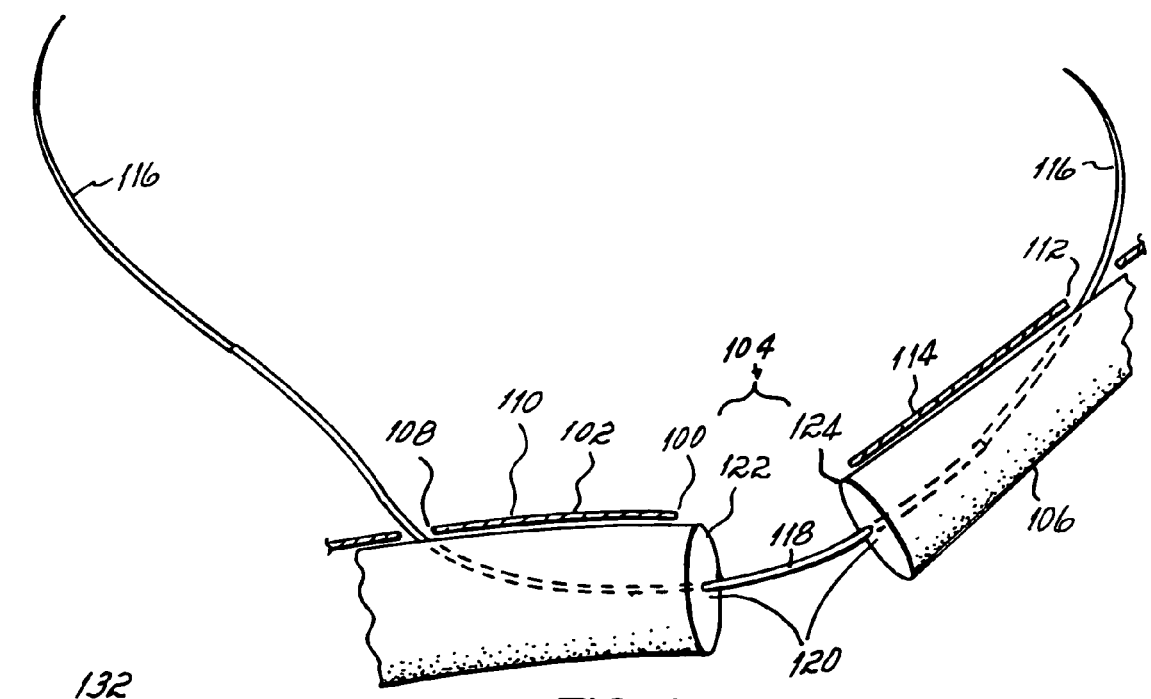
FIG. 14 is a sectional view of a tendon being repaired in accordance with the present invention.

As shown in FIGS. 13 and 14, a surgeon makes a first incision 100 in the skin 102 above the location of the tear 104 in the tendon 106. It is noted that the skin above the tendon tear 104 may have already been incised as in a laceration. If such is the case, only a small neatening of the incision may be relevant. The surgeon then makes a second incision 108 on the first side 110 of the first incision 100. The surgeon also makes a third incision 112 on the second side 114 of the first incision. These incisions 100, 108, 112 preferably involve several transverse incisions or short "T" or "L" incisions. Additional small "window" incisions may be necessary to gain access for retrieval of the tendon end. The incisions 100, 108, 112 may also involve rolling the tendon or ligament sheath down a distance of about 3 mm. A needle 116 (FIG. 14) is then threaded with a core suture or elongate tensile member 118. The needle 1167 is preferably a swaged, large radius, non-cutting needle, which allows the needle 116 to penetrate the filamentous tendon 106 without weakening it. For flexor tendons in the hand, the suture 118 is preferably USP size No. 1 or No. 2 and is preferably made of a monofilament of polyester, stainless steel, or polyglactin 910, or other high strength material. The needle 116 and attached suture 118 are then inserted into the tendon at the first side 112 of the tear 104. The needle 116 and the suture 118 travel down the center 120 of the tendon 106, exiting at the second incisions 108. The surgeon then inserts needle 116 and attached suture 118 at approximately the same center 120 of the second side 124 of tear 104. The needle 116 and attached suture 118 exit the tendon 104 through the third incision 112 on the second side 114 of the tear 104. The suture 118 is then tightened such that the first side 122 of the tear 104 is drawn into abutting relationship to the second side 124 of the tear 104, shown most clearly in FIG. 13. A second suture 118 may also need to be inserted in a similar fashion, as will become clear from the following description. Once the suture 118 has been properly placed, it must be secured in order to maintain the abutting relationship between first side 122 and second side 124 of tear 104.

Figure 15:
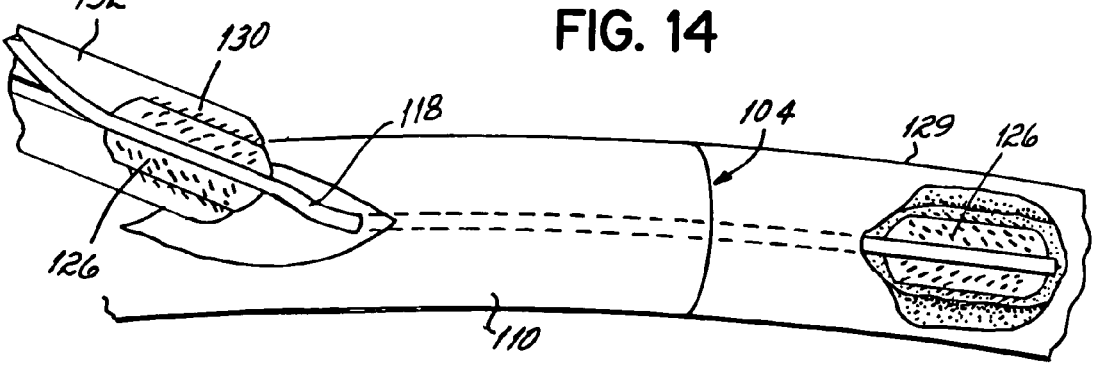
FIG. 15 is a sectional view of a tendon being repaired using a first embodiment of a button.
Figure 18A:
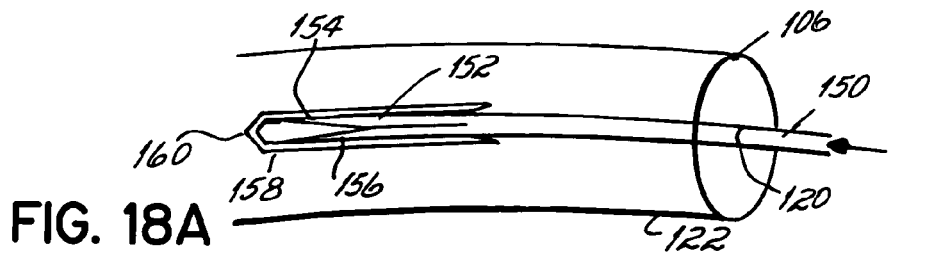
FIG. 18A is a sectional view of a step in repair of a tendon using a second embodiment of a suture in connection with the second embodiment of the button.
Figure 18B:
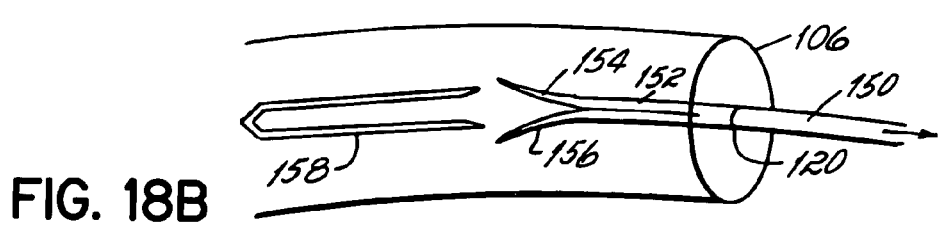
FIG. 18B is a sectional view of a step in repair of a tendon using a second embodiment of a suture in connection with the second embodiment of the button.
Figure 18C:
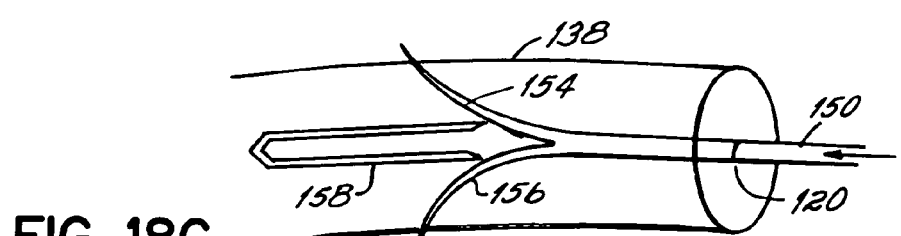
FIG. 18C is a sectional view of a step in repair of a tendon using a second embodiment of a suture in connection with the second embodiment of the button.
Figure 18D:
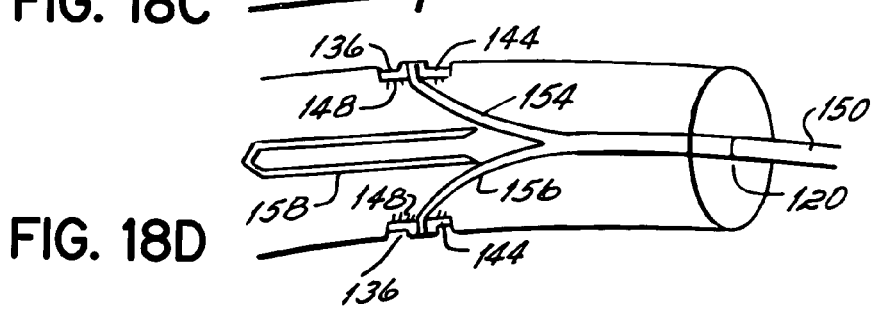
FIG. 18D is a sectional view of a step in repair of a tendon using a second embodiment of a suture in connection with the second embodiment of the present invention.

A first way of securing the suture is with a variety of buttons. A first embodiment is shown in FIG. 15 which shows the use of a sliding anchor button or body 126. A surgeon makes a stab or slit wound 128 in the tendon 106 in an area generally under the second incision 108 made on the first side 110 of the first incision 100. The sliding anchor button or body 126 slips onto the suture 118 and into the stab wound 128 under the exterior surface 129 of tendon 106. The sliding anchor button 126 has burrs 130 which serve to assist in holding sliding anchor button 126 in place in tendon 106 once it reaches the desired location. The burrs 130 are directed such that they are facing towards the tear 104 and generally outwardly from the suture 118 and serve to reduce the possible motion of sliding anchor button 126 and to distribute the axial load. In order to properly place the sliding anchor button 126, a tool 132 should be used which is capable of keeping the exterior surface of sliding anchor button 126 from coming into contact with tendon 106 prior to its correct placement. The tool 132 is important, since otherwise, the burrs 130 can tear or otherwise damage the tendon 106. Once the sliding anchor button 126 is in place, the tool 132 is retracted and sliding anchor button 126 is swaged to the suture 118 such that sliding anchor button 126 is attached to and at least partially circumscribes suture 118. FIGS. 15A-15D show a variety of possible forms for the sliding anchor button 126 in cross section. Each of these sliding anchor buttons 126 has a width W. Preferably width W is about 2 mm. As can be seen in these Figs., the sliding anchor button 126 can be configured such that it slides onto suture 118 by being threaded, as in FIGS. 15B-15D, or through a side slot as in FIG. 15A. Note also that in these embodiments, the burrs 130 are directed radially outwardly from the suture. Once the sliding anchor button 126 has been placed and swaged onto suture 118, the stab wound 128 is closed, preferably using a continuous microsuture. As can be seen in FIG. 16A, the stitches used to close the stab wound 128 may also penetrate to sliding anchor button 126 and to optional holes 133. Once one sliding anchor button 126 has been placed, a surgeon can insert a second sliding anchor button in the same way on the second side 114 of the first incision 100 below the third incision 112. During the installation of the second button 126, the abutting relationship between first side 122 and second side 124 of tear 104 is assured by pre-tensioning the core suture 118 as the second button 126 is attached. Tension may be applied by a special aspect of tool 132 or by manual means. The remainder of the procedure is the same as that mentioned above. Once a button has been inserted on each of first side 110 and second side 114, the tendon appears as is shown in FIG. 16. The incisions 100, 108, 112 may then be closed in any fashion known in the art.

A second embodiment of securing buttons is shown in FIG. 17. In FIG. 17, two sutures 118 are used to hold first side 122 and second side 124 in abutting relationship, as was mentioned above. In such a case, a first suture 118 must be placed to one side of the center 120 of tendon 106 and a second suture 118 must be placed to another side of the center 120 of tendon 106. If this embodiment is used, no stab wound need be made in the tendon 106. In this embodiment, once the suture is placed, the tab buttons 136 slide onto suture 118 until they reach the exterior surface 129. The suture 118 may be placed under greater tension by pushing tab buttons 136 such that they place some pressure on the exterior surface 138 of tendon 106. Once the tab buttons 136 have been appropriately placed, they are swaged or crimped to suture 118 such that they are attached to and circumscribe at least a part of suture 118, as shown most clearly in FIG. 17A, by a swaging tool 140. Preferably, as shown in FIG. 17B, the tab button 136 has a circular shape, and includes a central portion 142 and a circular flange 144. The central portion 142 and flange 144 include a slot 146 which allows tab button 136 to be easily placed on suture 118. When tab button 136 is in place, the flange 144 extends radially outwardly of the suture 118, shown most clearly in FIG. 17. The tab button 136 may include burrs 148 which extend generally outwardly from the suture 118 and serve to keep the tab buttons 136 in place and distribute the axial load. Once the first tab button 136 has been placed, a second, third, and fourth tab button 136 may be similarly placed using a similar method for each suture 118.

The tab button 136 may also be used with a different embodiment of the suture, as shown in FIGS. 18A-18D. In this embodiment, a split and monofilament 150 is used. The split end suture 150 is inserted in the center 120 of first side 122 of tendon 106, as shown by the direction of the arrow in FIG. 18A. The split end suture 150 has a first end 152. The first end 152 of split end suture 150 is divided into a first part 154 and a second part 156. When split end suture 150 is inserted into tendon 106, the first part 154 and second part 156 are contained within a cap 158 to retain first part 154 and second part 156 together. Cap 158 has a sharp end 160 to allow cap 158 to penetrate tendon 106. After the split end suture 150 and cap 158 reach an appropriate depth, the split end suture 150 is withdrawn in the direction of the arrow shown in FIG. 18B. The split end suture 150 is withdrawn only to just beyond the cap 158. The split end suture 150 is then pushed in an inward direction as noted by the arrow in FIG. 18C. When the split end suture 150 is pushed, the first part 154 and second part 156 split apart and eventually break the exterior surface 138 of tendon 106. A fifth and sixth tab button 136 are then attached to the first part 154 and second part 156, respectively, such that fifth and sixth tab buttons 136 are attached to and at least partially circumscribe the first part 154 and second part 156, respectively. The same operation would apply on the second end (not shown) of the split end suture 150, which is substantially the same as the first end 152 of split end suture 150. The second end would simply be inserted into the second side 124 of tear 104. Other considerations which would be relevant are that the split end suture 150 should ideally be inserted such that half of it extends into each of first side 122 and second side 124, and the first side 122 and second side 124 must be held in an abutting relationship, so that the entire length of the split end suture 150 should be within the tendon 106. The tab buttons 136 used with the split end suture 150 are the same as those mentioned earlier and may include flanges 144 or burrs 148.

Figure 19:
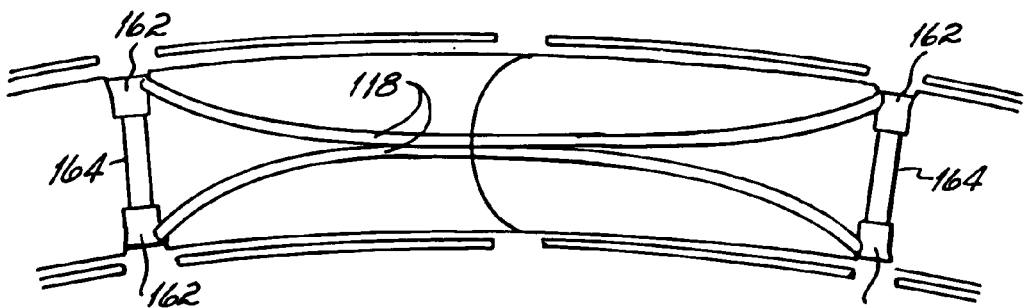
FIG. 19 is a sectional view of a repaired tendon using a third embodiment of the present invention.
Figure 19A:
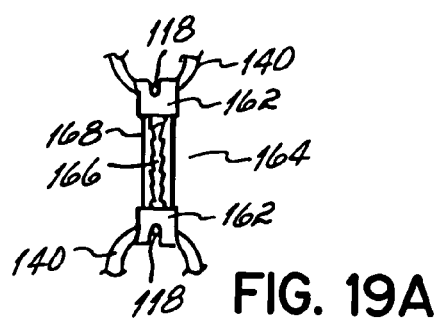
FIG. 19A is a sectional view of the button of FIG. 19.

Turning now to FIG. 19, a third embodiment of buttons is shown. The transverse button 162 is again used in conjunction with two sutures 118, inserted as described above. The transverse button 162, as shown in FIG. 19A, is attached to an partially circumscribes a first suture 118 and is swaged or crimped onto the first suture 118 with a swaging tool, such as tool 140. Another transverse button 162 is attached to and partially circumscribes a second suture 118 and is swaged or crimped onto the second suture 118 with a swaging tool, such as tool 140. In this embodiment, the transverse buttons 162 are attached to each other by a telescoping mating pin 164. Attached to one of the transverse buttons 162 is the male portion 166 of the pin 164, and attached to the other transverse button 162 is the female portion 168 of the pin 164. The male portion 166 and the female portion 168 are pushed towards each other through tendon 106. When male portion 166 and female portion 168 reach each other, they ratchet and lock, thereby causing one of the transverse buttons 162 to be attached to the other transverse button 162.

Figure 20A:
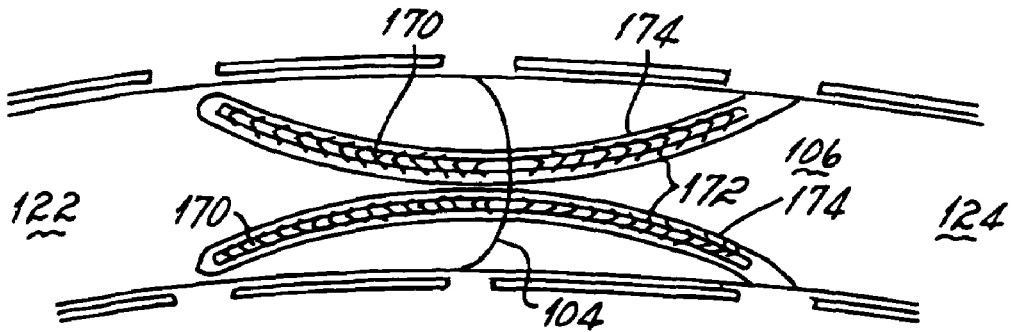
FIG. 20A is a sectional view of a step in the repair of a tendon using a fourth embodiment of the present invention.
Figure 20B:
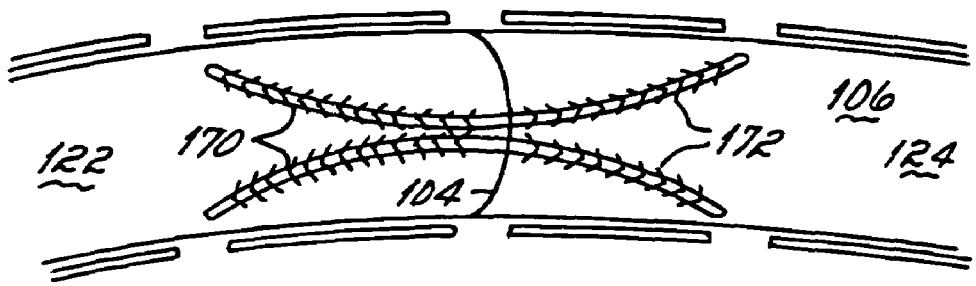
FIG. 20B is a sectional view of a repaired tendon using the fourth embodiment of the present invention.

The second method of securing the suture, instead of using buttons, is by using the suture itself. Turning to FIGS. 20A and 20B, the suture 170 includes barbs 172, which serve to secure the suture 170 and distribute the axial load. When the barbed sutures 170 are inserted into tendon 106 as described above, the sutures must be completely surrounded by a cannula 174 or other protective device which serves to keep barbs 172 from become attached to tendon 106 prior to proper placement. Once suture 170 is properly placed, as shown in FIG. 20A, cannula 174 is removed in any standard way. The barbs 172 will then keep the suture 170 in place and keep first side 122 and second side 124 of tear 104 in abutting relationship.

An alternative installation process may be used in this invention where a single suture has a needle on each end. In which case the needles enter the central wound opening and each penetrates the severed end of the tendon; the two needles moving in opposite directions to exit at one of the window openings spaced from the wound. After each needle exits the suture is tightened and the tendon ends are drawn together by the structure and procedural steps described above.

Device for Securing a Torn Tendon to a Bone

Figure 21:
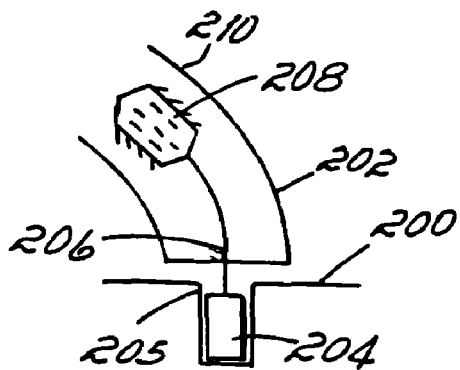
FIG. 21 is a sectional view of a tendon repair device in accordance with the present invention used in connection with a bone anchor.

This invention relates to the use of a button as described above in connection with a known bone anchor in order to secure a tendon to a bone. Turning first to FIG. 21, a system is shown for attaching a bone 200 and a tendon or ligament 202. A bone anchor 204 is installed in a hole 205 in the bone 200. Any of the standard bone anchors known in the art are suitable, as long as they are capable of being attached to a flexible suture 206. As shown in FIG. 21, a sliding anchor button 208 is attached to the flexible suture 206 and at least partially circumscribes the flexible suture 206. The sliding anchor button shown in connection with the bone anchor 204 is inserted as was described earlier in connection with the tendon repair device under the surface 210 of the tendon 202.

Figure 22:
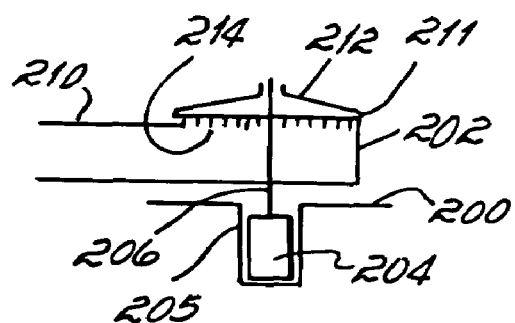
FIG. 22 is a sectional view of a second tendon repair device in accordance with the present invention used in connection with a bone anchor.

Turning now to FIG. 22, a second embodiment of the tendon-bone anchor is disclosed. This embodiment is most preferably used when the tendon has a relatively thin cross-section, such as for exterior tendons and most ligaments. Again, bone anchor 204 is installed in a hole 205 in the bone 200. Any of the standard bone anchors known in the art are suitable, as long as they are capable of being attached to a flexible suture 206. Also attached to the flexible suture 206 is a tab button 212, which includes barbs 214 extending generally parallel with flexible suture 206 and radially outward on flange 211. Tab button 212 is attached to suture 206 as was described above such that tab button 212 is attached to and at least partially circumscribes suture 206.

Figure 23A:
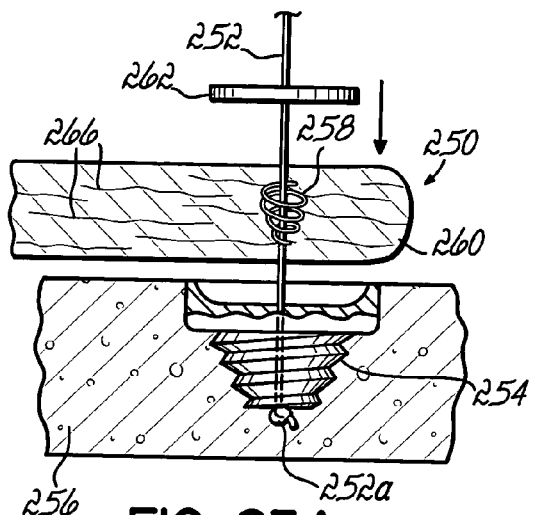
FIG. 23A is a sectional view illustrating an alternative embodiment of a tendon-to-bone repair apparatus in exploded form.
Figure 23B:
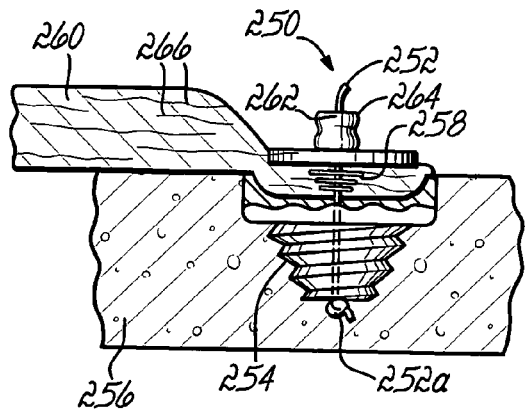
FIG. 23B is a sectional view similar to FIG. 23A, but showing the apparatus in assembled form attaching the tendon to the bone.
Figure 23C:
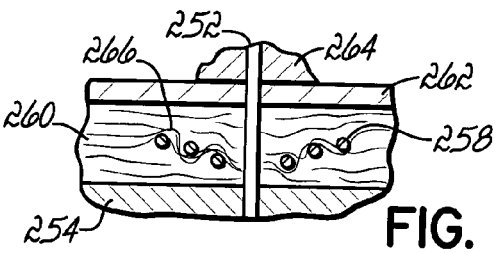
FIG. 23C is an enlarged sectional view of the apparatus as shown in FIG. 23B, specifically illustrating the compression of tendon fibers within a helical anchor of the present invention.

Another embodiment of a tendon to bone repair apparatus 250 is shown in FIGS. 23A-23C. In this embodiment, apparatus 250 includes an elongate tensile member 252 connected at one end with a bone anchor 254, such as by a knot or other stop member 252a. Bone anchor 254 may be a conventional bone anchor configured for retainment within a bone 256. Apparatus 250 further includes a helical, compressible anchor 258 which has been rotated into a tendon or ligament 260. A retaining member 262, which may simply comprise a small button in this embodiment, receives elongate tensile member 252, which may be a strong suture, and slides down onto tendon 260 as shown in FIG. 23B. A locking member, which may be a crimp member 264 receives elongate tensile member 252 and slides down on top of retaining member 262 where upon it is deformed or crimped and locked onto elongate tensile member 252 to hold apparatus 250 together with a portion of tendon 260 held firmly against bone anchor 254. As further detailed in FIG. 23C, the compressible, helical anchor 258, which may have the tapered configuration as shown or other configurations as detailed herein, traps fiber 266 of tendon 260 in a generally sinusoid pattern between respective coils of anchor 258.

Figure 24A:
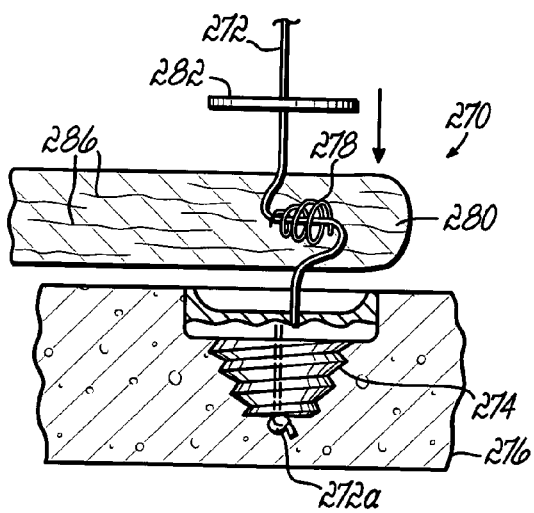
FIG. 24A is a sectional view of another alternative tendon-to-bone repair apparatus shown in exploded form.
Figure 24B:
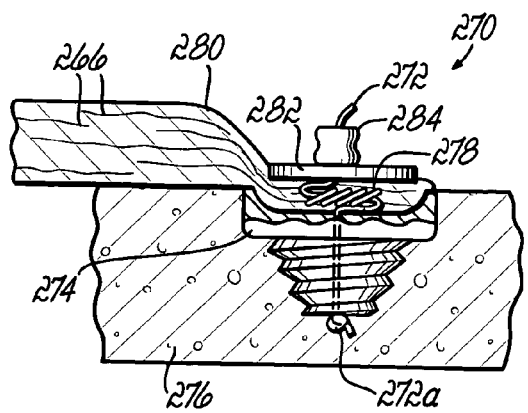
FIG. 24B is a sectional view similar to FIG. 24A, but showing the apparatus in assembled form.
Figure 24C:
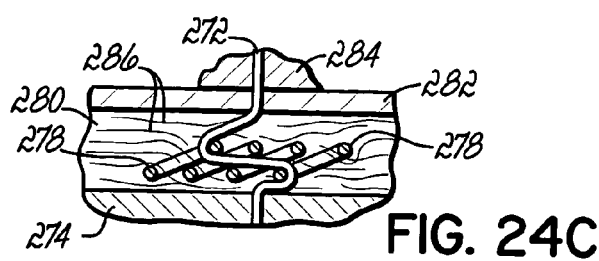
FIG. 24C is an enlarged sectional view of the apparatus shown in FIG. 24B.

Another embodiment of a tendon to bone repair apparatus 270 is shown in FIGS. 24A-24C. Apparatus 270 also comprises an elongate tensile member 272 connected with a bone anchor 274 again by way of a suitable stop, knot or other method. Bone anchor 274 is fixedly secured within a bone 276. A helical anchor 278 is rotated into a tendon or ligament 280 and is compressible. Unlike the previous embodiment, however, anchor 278 is inserted generally with its axis in line with the length of tendon or ligament 280 and anchor 278 is compressible generally along its length, as shown in FIG. 24B. When a retaining member 282 is received on elongate tensile member 272 and compressed onto tendon 280, against bone anchor 274, this will compress helical anchor 278 in a sideward manner as shown. A locking member 284, which again may be a crimp member integral or separate from retaining member 282, is then slid down elongate tensile member against retaining member 282 to hold apparatus 270 in the position shown in FIG. 24B. As shown in FIG. 24C, elongate tensile member 272 extends through the center of helical anchor 278 generally along the lengthwise axis thereof and from one end to the other, although the helical anchor may intertwine with the coils of anchor 274 in other manners as well. Fibers 286 of tendon 280 will extend between the coils of anchor 274 in a generally sinusoidal pattern thus firmly trapping anchor 274 within tendon or ligament 280.

Figure 25A:
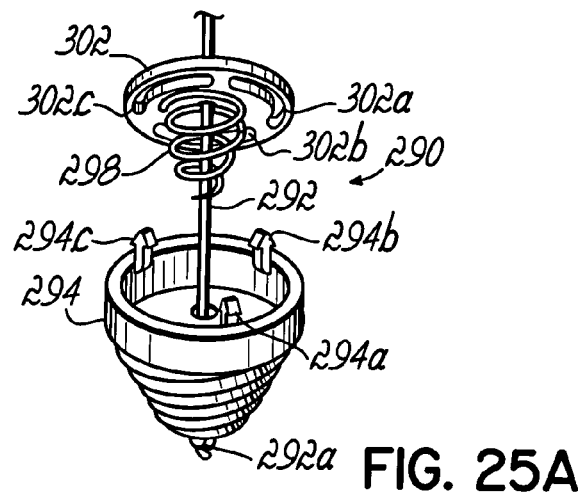
FIG. 25A is a perspective view showing another alternative tendon-to-bone repair apparatus in exploded form.

Another embodiment 290 is shown in FIG. 25A. Apparatus 290 comprises an elongate tensile member 292 suitable connected to a bone anchor 294 by way of a knot or stop member 292a or another method. Apparatus 290 further includes a helical anchor 298, which again is preferably compressible, and received on elongate tensile member 292. A retaining member 302 is also received on elongate tensile member 292 as shown in FIG. 25A. Locking members, in the form of projections 294a, 294b, 294c, are disposed on bone anchor 294 and register in receiving slots 302a, 302b, 302c within retaining member 302. Apparatus 290 is used in a manner similar to apparatus 250 shown in FIGS. 23A-23C, except that after helical anchor 298 has been rotated into a tendon, retaining member 302 is pushed or rotated simultaneously with helical anchor 298 if anchor 298 is attached to retaining member 302, and locked onto bone anchor 294 through the receipt of projections 294, 294b, 294c within the respective slots 302a, 302b, 302c. The insertion and retainment of helical anchor 298 within a tendon or ligament may advantageously occur in a single surgical step if helical anchor 298 is connected for rotation with retaining member 302. In this case, for example, rotation of retaining member 302 can simultaneously rotate helical anchor 298 into a tendon or ligament and lock the assembly onto bone anchor 294.

Figure 25B:
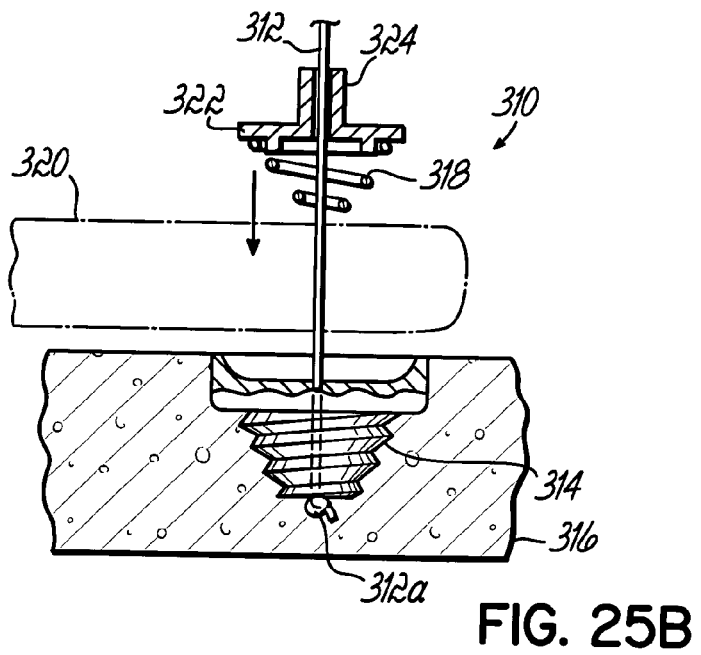
FIG. 25B is a sectional view of another tendon-to-bone repair apparatus.

Another embodiment of a tendon to bone repair apparatus 310 is shown in FIG. 25B. In apparatus 310, an elongate tensile member 312 is again connected with a bone anchor 314 by a suitable method, such as a knot 312a. Bone anchor 314 is securely affixed, such as by a threading action within a bone 316. A helical anchor 318 is received on elongate tensile member 312 and is adapted to be rotated into a tendon 320. Helical anchor 318 is connected to a retaining member 322 in this embodiment either through a mechanical or integral connection. A locking member 324, which again may comprise a crimp member, is integrally formed with retaining member 322 in this alternative embodiment. In its attached configuration, apparatus 310 is very similar to apparatus 250 shown in FIGS. 23A-23C with helical anchor 318 being trapped within tendon 320 and fibers thereof being generally sinusoidally trapped between the coils of anchor 318.

Figure 26:
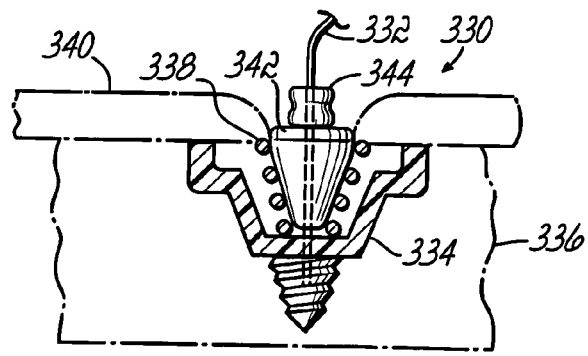
FIG. 26 is a sectional view illustrating yet another alternative tendon-to-bone repair apparatus also including a helical anchor system according to the invention.

Another alternative tendon bone repair apparatus 330 is shown in FIG. 26. Apparatus 330 includes an elongate tensile member 332 connected in a suitable rigid manner to bone anchor 334 such that it may be placed into tension. Bone anchor 334 is again affixed securely within a bone 336. A helical anchor 338 is rotated into a tendon or ligament 340 in a manner similar to the embodiment, for example, of FIGS. 23A-23C. In this embodiment, however, a retaining member 322 is provided for at least partial insertion within anchor 338 as shown in the assembled condition of FIG. 26. This traps fibers between retaining member 342 and the coils of anchor 338. Once retaining member 342 is securely received within anchor 338, a locking member 344, which may be integral to or separate from retaining member 342, is slid onto elongate tensile member 332 against retaining member 342 and crimped onto tensile member 332. It should be appreciated that, although the elongate tensile members of the embodiments shown in FIGS. 23A-26 are flexible sutures, these may also be more rigid tensile members, such as members made of biocompatible metals or they may alternatively be formed of absorbable materials. One or more of the other elements of these tendon to bone repair apparatus may also be formed of absorbable materials.

Alternative Tendon Repair Apparatus

Figure 27:
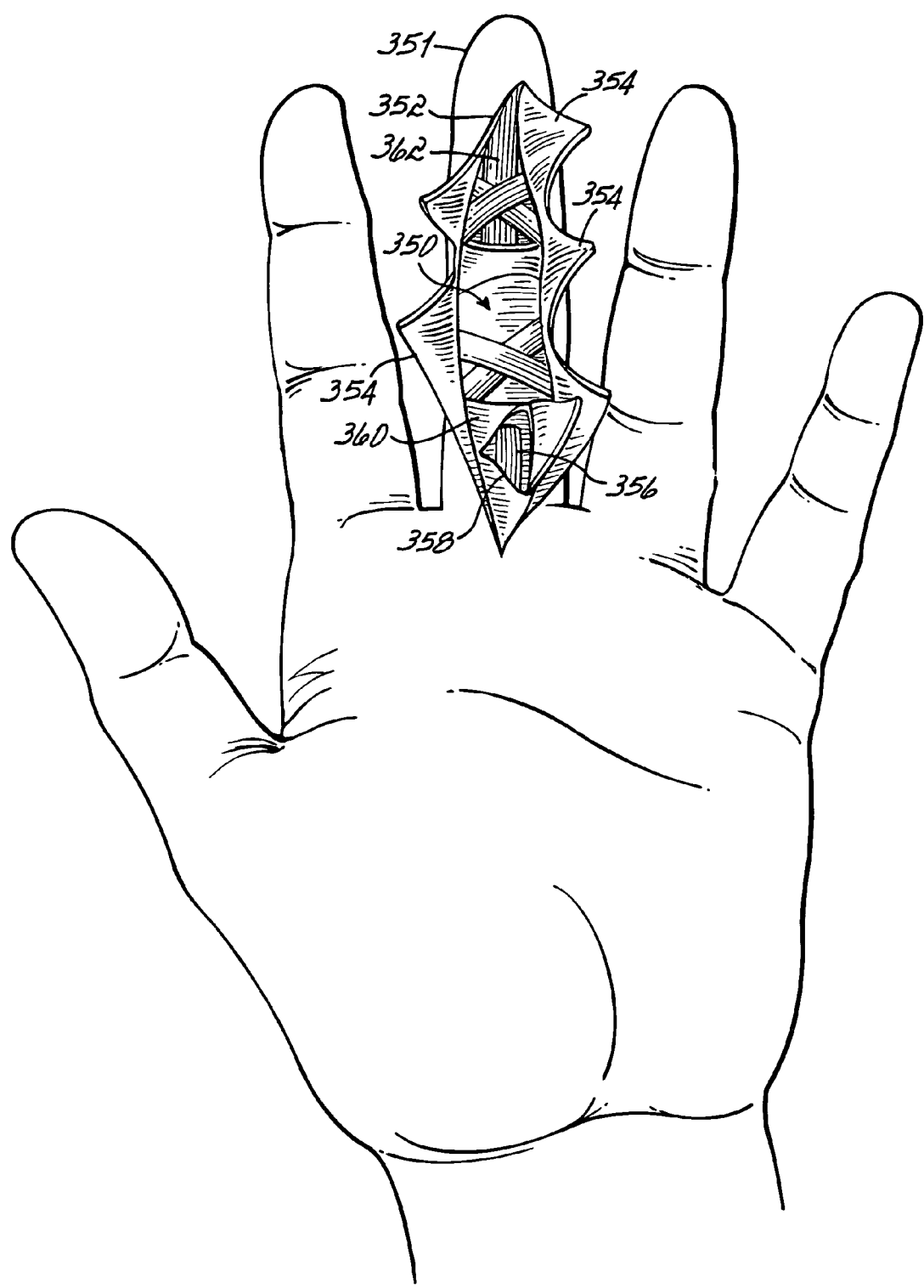
FIG. 27 is a top view showing incisions made in a finger to access a tendon in accordance with additional aspects of the invention.

The invention contemplates further embodiments of tendon-to-tendon or ligament-to-ligament repair apparatus. For simplicity, only the term "tendon" is used herein at various points. A review of the general procedure is appropriate with reference first to FIGS. 27 and 28. When faced with repairing a severed or otherwise damaged tendon, the surgeon must make an incision to repair the severed or damaged tendon. FIG. 27 shows the actual laceration site 350 of a finger 351 and the augmented incision 352 made by the surgeon to gain access. After the incision has been made the skin flaps 354 are reflected back for full visualization of the damage. The surgeon will retrieve the proximal tendon segment 356 of the damaged tendon through a triangular window access incision 358 made in the tendon sheath 360. The triangular incision 358 helps prevent the end of the proximal tendon segment 356 from catching on window incision 358 as it is retrieved. The distal segment 362 of the damaged tendon will also be retrieved in the same manner. Once the tendons ends have been retrieved as shown in FIG. 28, they are held in place temporarily with transfixation needles 364. The function of these needles is to hold the tendon segments 356, 362 together without damaging the tips of the tendon which must be kept as trauma free as possible to promote a good repair.

FIG. 29 shows the transfixed tendon ends 370, 372 without the surrounding anatomy and transfixation needles 364. In accordance with the invention, access incisions 374 of about 0.5 cm in length is made approximately 2-3 cm from the lacerated ends 370, 372 of the tendon. Preferably, a No. 2 suture 376 is placed in through the access incision 374 of the proximal tendon segment 356 out through the lacerated end 372 of the proximal segment 356 into the lacerated end 370 of the distal tendon segment 362 and out through the access incision 374 of the distal tendon segment 362. Once the suture 376 is placed lengthwise through the tendon with a needle 378, the surgeon places an anchor system of this invention into the tendon body.

FIG. 31A illustrates an alternative tool 392' for rotating helical anchor 390 into the tendon. Tool 392' includes a flexible, hollow shaft 396', however, in this embodiment shaft 396' is contained within a hollow sheath 397 which is also flexible. Anti-rotation structure 399 is disposed within sheath 397 and may be actuated between a retracted position within sheath and an extended position as shown in FIG. 31A. In the illustrative example shown, structure 399 comprises spikes that flare outwardly into tendon segment 356 to prevent rotation of tendon segment 356 as flexible shaft 396' is rotated, while sheath 397 remains stationary. This prevents the tendency of the tendon from rotating with the anchor as the anchor is rotated into place.

Referring now to FIGS. 29-31, a first alternative helical anchor repair apparatus is shown being inserted into tendon segments 356, 362. This includes a first helical anchor 390 being applied with a tool 392 having a handle 394 and a flexible shaft 396. It will be appreciated that many different tool configurations may be used in place of tool 392. A distal end of tool 392 includes an anchor mounting portion 398 having a blunt tip. A trailing end 400 of helical anchor 390 includes a drive portion received in an aperture 402 associated with a hub 404 of end portion 398. Anchor 390 further includes a leading end 406 which may be formed as either a sharpened or blunt tip. Anchor mounting portion 398 further includes a suitable aperture (not shown) along its length such that elongate tensile member or suture 376 may be threaded therethrough as shown in FIG. 29. Thus, anchor 390 is releasably attached to end portion 398 and elongate tensile member 376 extends through the center of helical anchor 390.

Figure 33:
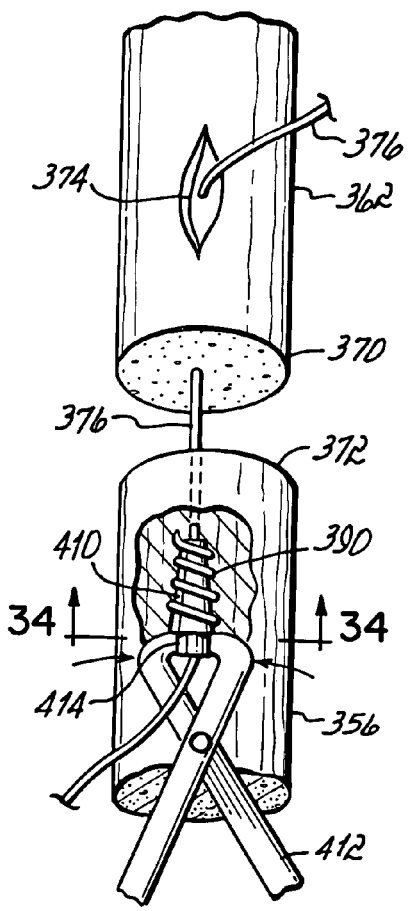
FIG. 33 is a partially fragmented sectional view similar to FIG. 32, but showing the locking of the retaining member to the elongate tensile member.
Figure 34:
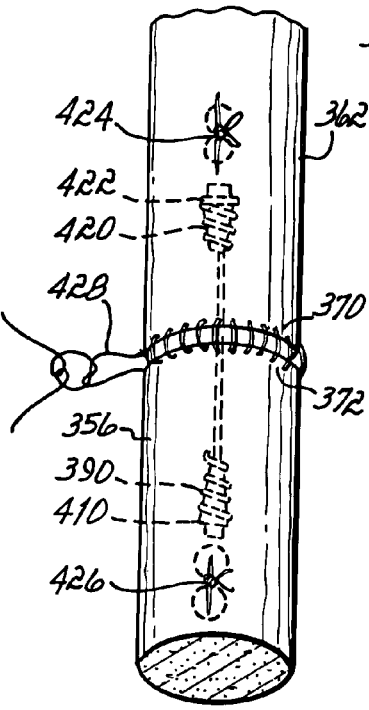
FIG. 34 is a sectional view taken along line 34-34 of FIG. 33.
Figure 34A:
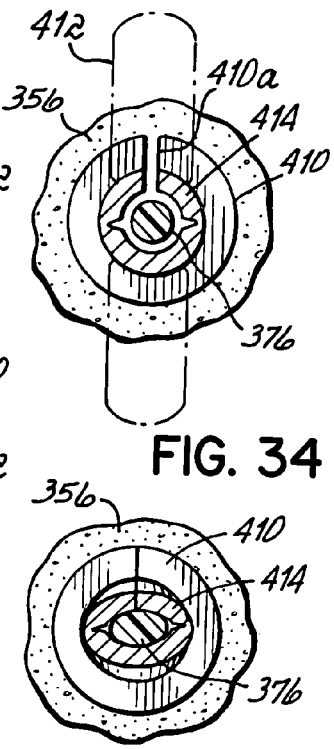
FIG. 34A is a sectional view similar to FIG. 34, but illustrating the locking portion of the retaining member in a crimped or deformed condition.

Tool 392 is used to rotate helical anchor 390 like a screw into tendon segment 356 through access incision 374 and rotated into place as shown in FIG. 31. At this point, the surgeon pulls back on tool 392 thereby releasing mounting end portion 398 from helical anchor 390. At this point, and as shown in FIG. 32, a retaining member 410 is installed at least partially within helical anchor 390. An installation tool 412 is used to grasp retaining member 410, which is slidably received on elongate tensile member 376. The surgeon slides retaining member 410 along elongate tensile member or suture 376 until reaching the position shown in FIG. 33. This traps and compresses the collagen fibers of the tendon between retaining member 410 and helical anchor 390 in a manner to be discussed further below. When retaining member is firmly situated within helical anchor 390, the surgeon can deform a rear crimpable portion 414 as depicted in FIGS. 33, 34 and 34A. In this regard, FIG. 34 shows rear crimpable portion 414 in an uncrimped state, while FIG. 34A shows crimpable portion 414 in a crimped position securely affixed to elongate tensile member 376. This fixes the anchor structure, comprising anchor 390 and retaining member 410 securely to the fibers within tendon segment 356 and also affixes the anchor structure to the desired location on elongate tensile member suture 376. Upon completion of this step, the surgeon moves on to tendon segment 362 and applies a similar procedure to affix a second helical anchor 420 and retaining member 422 to the suture 376 through access incision 374. Prior to crimping retaining member 422 onto suture 376, the surgeon may adjust the distance between tendon ends 370, 372 by sliding the anchor structure 420, 422 along suture 376 while applying a force, such as with tool 412, to move the assembly 420, 422 along with tendon segment 362 toward the opposite segment 356. When the desired repair position is reached, for example, with tendon ends 370, 372 approximately 1-2 mm apart, the surgeon crimps retaining member 422 to suture 376 in a manner similar to FIG. 34A.

Figure 35:
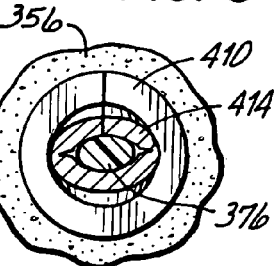
FIG. 35 is a perspective view of the tendon repaired in accordance with the invention.

It will be understood that other manners of locking a retaining member, such as members 410 and 422, in place may be used instead of crimp members or deformable portions of the retaining members. As shown in FIG. 35, opposite ends of suture 376 are cut at locations close to the respective retaining members 410, 422 and access incisions are closed, such as by using sutures 424, 426 or another acceptable method. Finally, a running suture 428 is placed at the junction of tendon ends 370, 372 or, again, another acceptable connection method may be used.

Figure 36:
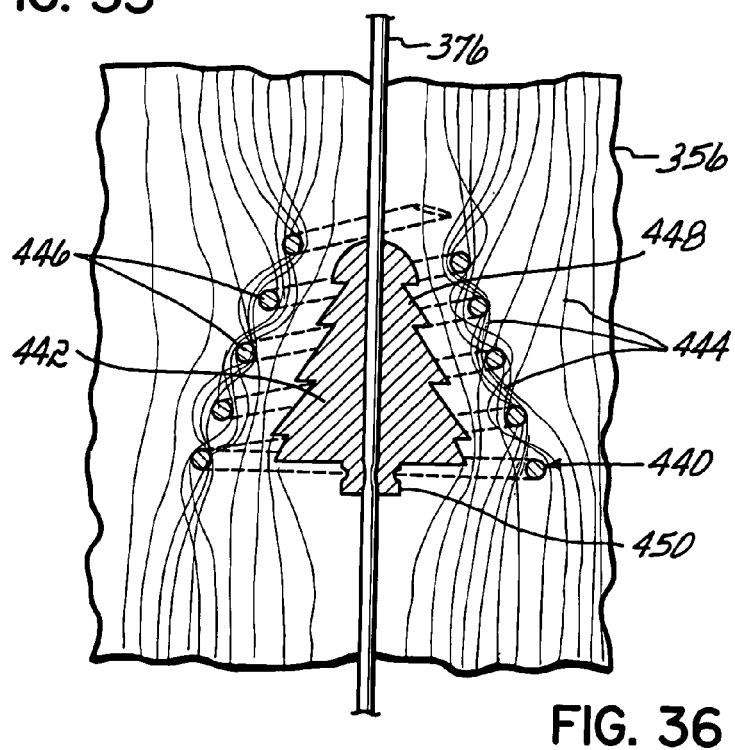
FIG. 36 is an enlarged sectional view schematically illustrating the attachment of a tendon repair apparatus of this invention to the tendon fibers.

FIG. 36 illustrates an alternative helical anchor 440 and retaining member 442 connected to elongate tensile member or suture 376 and held within tendon segment 356. FIG. 36 further illustrates the benefits of the invention in more detail. In this regard, fibers 244, which extend lengthwise within tendon segment 356 have been engaged within coils 446 of anchor 440 as anchor 440 was rotated into place as previously described. This engagement will occur generally in a sinusoidal pattern as shown, although the number and density of fibers 444 has been drastically reduced in the figure for clarity. Retaining member 442 may also have a discontinuous outer surface 448, as shown, such as a serrated surface as shown in cross section in this view. This will further help retain the tendon fibers 444 between retaining member 442 and helical anchor 440 and prevent retaining member 442 from backing out of helical anchor 440. An integral crimp member 450 is disposed on a trailing end of retaining member 442. A separate crimp member or other locking structure may be used in its place.

Figure 37:
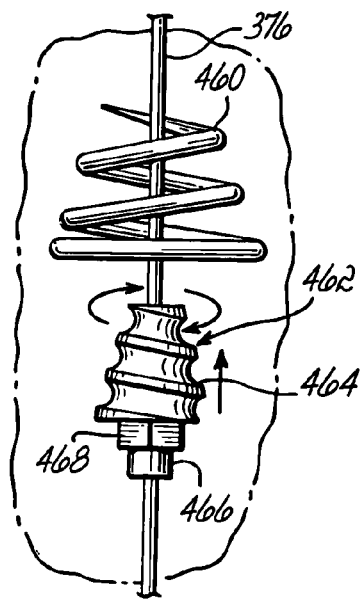
FIG. 37 is a plan view of an elongate tensile member, helical anchor, and retaining member in accordance with another embodiment of the invention.

FIG. 37 discloses another alternative embodiment including a helical anchor 460 and a retaining member 462 adapted to be fixed into place on elongate tensile member 376 in a manner generally similar to the previous helical anchor embodiments. In this embodiment, retaining member 462 includes a discontinuous outer surface in the form of a threaded surface 464 which provides an anti-backout function and will allow gripping of the tendon fibers as retaining member 462 is rotated into helical anchor 460. A crimp member 466 may be provided to fix retaining member 462 in place as previously described. Also, suitable flats 468 may be provided for tool engagement allowing rotation of retaining member 462.

Figure 37A:
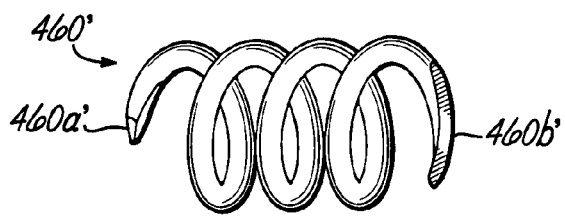
FIG. 37A is a perspective view of another embodiment of a helical anchor constructed in accordance with the invention.
Figure 37B:
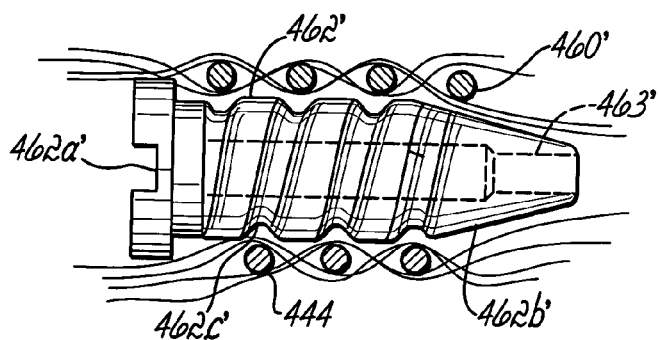
FIG. 37B is an elevational view of repair apparatus including the helical anchor of FIG. 37A and a retaining member shown affixed to an elongate tensile member within a tendon in accordance with the invention.

FIGS. 37A and 37B respectively illustrate another alternative embodiment of a helical anchor 460' and an anchor structure comprising a helical anchor and retaining member 460', 462'. Helical anchor 460' has opposite, tapering but blunt ends 460a', 460b' to allow insertion into a tendon at either end 460a' and 460b'. The blunt ends 460a', 460b' will spread the tendon tissue during entry as opposed to tearing, slicing or otherwise damaging the tissue. Other sharpened or blunt end configurations may be used as well. Retaining member 462' includes a slot 462a' at a trailing end for engagement with a rotating tool, and a tapered leading end 462b' for entry into helical anchor 460'. An outer surface 462c' is discontinuous in a convoluted, generally helical manner to generally register with the coils of helical anchor 460'. Thus, fibers 444 will be retained during use in a generally sinusoidal manner between the coils of helical anchor 460' and the convoluted outer surface 462c' of retaining member 462'. Finally, retaining member 462' includes a central aperture 463 along its longitudinal axis for receiving an elongate tensile member such as the previously described suture 376.

Figure 38:
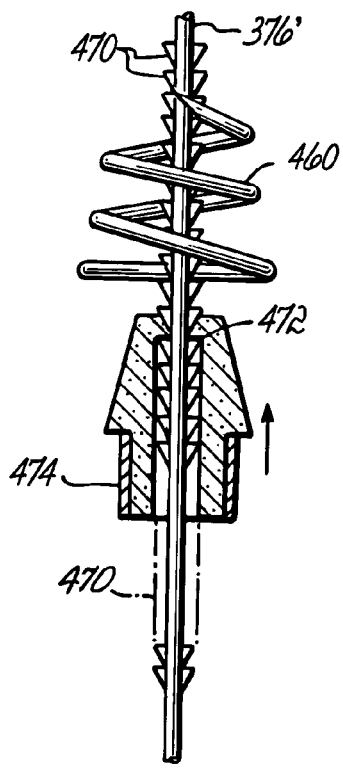
FIG. 38 is a partially sectioned plan view showing another embodiment of a helical anchor system.
Figure 39:
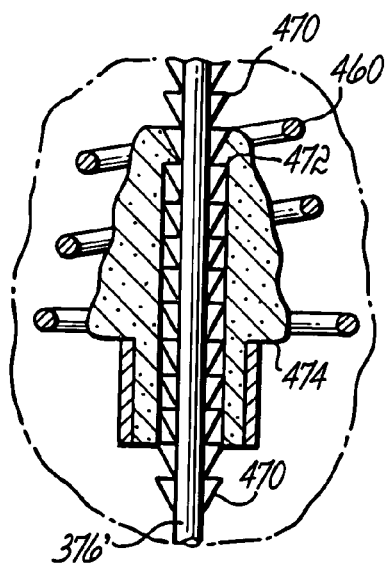
FIG. 39 is an enlarged partially sectioned view similar to FIG. 38, but illustrating the partial absorption of the retaining member in accordance with this embodiment.

FIGS. 38 and 39 illustrate another alternative embodiment utilizing a modified elongate tensile member 376' having barb or ratchet structure 470. Ratchet structure 470 is engageable with an internal portion 472 of a retaining member 474. Therefore, as retaining member 474 is moved into helical anchor 460, the interaction of structures 470 and 472 will prevent retaining member 474 from backing out. This therefore provides an alternative locking structure for holding retaining member 474 against anchor 460 with tendon fibers trapped and compressed therebetween. As further shown in FIG. 39, retaining member 474 may be formed from absorbable material, such as polyglycolic acid or polyglyconate. As retaining member 474 is absorbed, more tensile force will be experienced at the repair site as retaining member 474 will tend to move slightly further into helical anchor 460. This gradual increase in tensile stress at the repair site will promote faster and stronger healing.

FIGS. 40-42 illustrate three potential alternative embodiments of helical anchors, namely, anchors 480, 482 and 484. As currently contemplated, the anchors will be tapered from a larger diameter at a trailing end to a smaller diameter at a leading end to assist in threading the anchor into the tendon tissue. However, it will be understood that many other configurations are possible as well with a few of the possibilities illustrated in FIGS. 40-42. In FIG. 40, helical anchor 480, shown in cross section, has a varying diameter along its length and an axis 486 which is not parallel to elongate tensile member 376 during use. Also, tensile member 376 travels partially within the coils of anchor 480 and partially outside of the coils. In FIG. 41, a similar configuration is shown, except that tensile member 376 is contained entirely within helical anchor 482 and anchor 482 has coils of approximately equal diameter along its length. FIG. 42 illustrates an anchor 484 that converges in diameter centrally from each end.

FIG. 43 illustrates another embodiment of the invention wherein the elongate tensile member 376 is retained by a wedging action between a retaining member 490 and a helical anchor 492. Retaining member 490 may have a serrated or otherwise discontinuous outer surface 494 for assisting in wedging and retaining elongate tensile member 376 against tendon fibers 496 and helical anchor 492. Again, the number and density of fibers 496 is drastically reduced in FIG. 43 for clarity.

Another embodiment of the invention is shown in FIGS. 44A and 44B. This embodiment is similar to the embodiment shown in FIG. 36 but illustrates the effect of forming retaining member 442' from absorbable materials. The effect is similar to the effect described above in connection with FIGS. 38 and 39. That is, as retaining member 442' absorbs into the tendon, the repair site will experience a greater amount of tensile force during physical therapy or other motion of the tendon. Again, this will speed the healing process and result in strengthening the repair site.

FIGS. 45A-45C illustrate a further use of absorbable materials for helical anchor 440', retaining member 442' and elongate tensile member 376". In this embodiment, each of the elements will gradually absorb as shown progressively in the figures such that the function of transferring more tensile stress to the repair site is accomplished and such that the repair apparatus as a whole will fully or substantially absorb into the tendon after it has fulfilled its repair function. In this embodiment, the absorption rates of the different components may be varied by using different materials. For example, retaining member 442' may be formed to absorb faster than elongate tensile member 376" or anchor 440' such that tension is, at first, gradually transferred to the repair site. Then, after full healing has taken place, the remaining components can absorb into the tendon, removing all tensile reinforcement from the repair.

Figure 46:
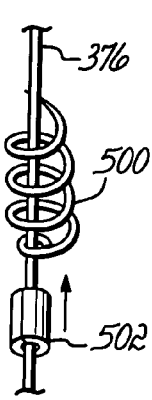
FIG. 46 is a perspective view showing the partially assembled condition of another alternative repair apparatus employing a compressible helical anchor.
Figure 47A:
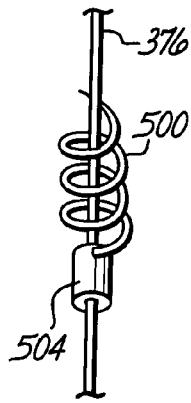
FIG. 47A is a perspective view of an alternative apparatus employing a compressible helical anchor with an integrated locking member.
Figure 47B:
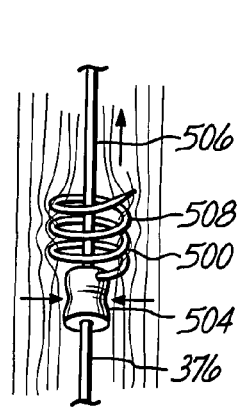
FIG. 47B is a perspective view illustrating the embodiment of FIG. 47A in a compressed and locked condition within a tendon.

FIG. 46 illustrates an alternative embodiment of the invention comprising a compressible, helical anchor 500 receiving elongate tensile member 376 and adapted to be retained in place within a tendon through a compressing action brought about by a suitable structure on elongate tensile member 376, such as a separate crimp member 502 or an integral or attached crimp member associated with helical anchor 500 as shown in FIGS. 47A and 47B. It will be understood that many other potential locking structure may be substituted for crimp members 502 and 504 as long as the ultimate function of compressing helical anchor 500 is accomplished. As shown in FIG. 47B, when crimp member 502 or 504 is fixed onto elongate tensile member 376, an elongate tensile member 376 is pulled in the direction of arrow 506, toward the repair site, the coils of helical anchor 500 will compress and securely engage the tendon fibers therein. In this manner, helical anchor 500 will be locked onto tendon fibers 508 and the tendon segments may be pulled together at the repair site in the manner described above.

Figure 48A:
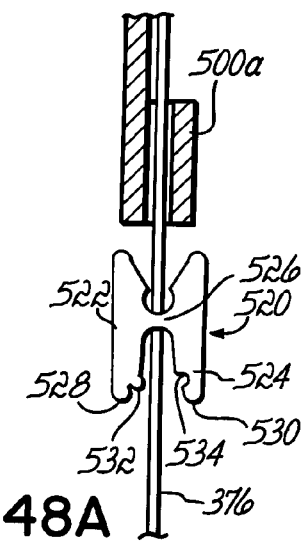
FIG. 48A is a partially sectioned view of an alternative embodiment for a locking member used to retain a helical anchor at a selected position along the elongate tensile member and showing the locking member in an adjustable condition.
Figure 48B:
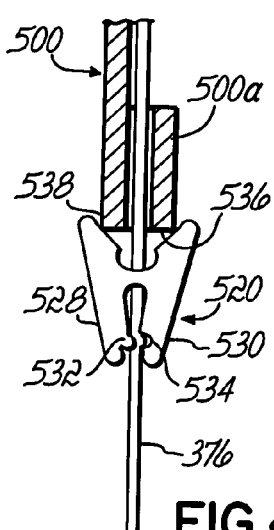
FIG. 48B is a partially sectioned view similar to FIG. 48A, but showing the locking member in a locked condition.

An alternative crimp member is shown in FIGS. 48A and 48B. In this embodiment, crimp member 520 comprises first and second movable portions 522, 524 connected at a central portion 526. Crimp member 520 may be received on and slid along elongate tensile member 376 in abutting relation to a trailing end portion 500a of helical anchor 500 and crimped against elongate tensile member 376 by squeezing ends 528, 530 together as shown in FIG. 48B. A nub 532 and opposing recess 534 may be provided to help retain crimp member 520 fixed against elongate tensile member 376. Opposite ends 536, 538 may bear against trailing end portion 500a. In this manner, the assembly may be used, for example, in the manner described with respect to FIG. 47B.

Figure 49A:
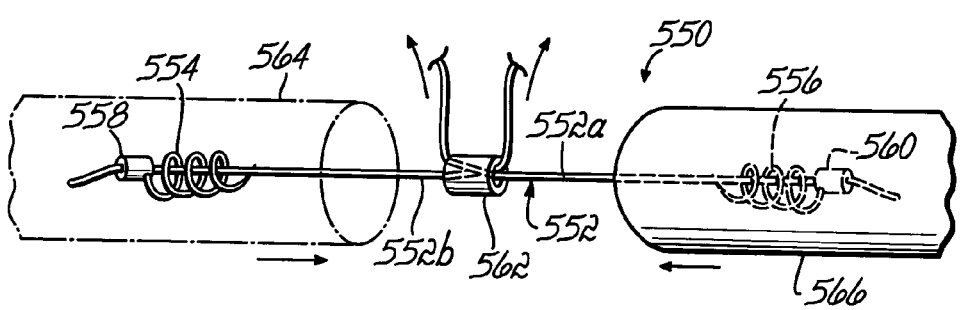
FIG. 49A is a perspective view showing another alternative tendon repair apparatus employing compressible, helical anchors in accordance with the invention.
Figure 49B:
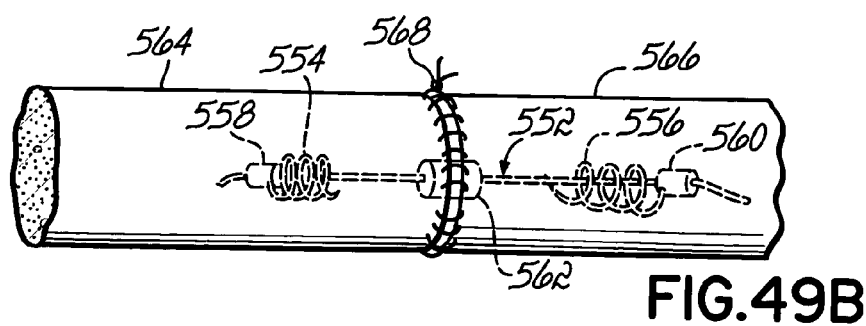
FIG. 49B is a perspective view similar to FIG. 49A, but showing the apparatus fully implanted to repair the tendon.

An alternative embodiment of a repair apparatus 550 incorporating an elongate tensile member 552 and a pair of compressible, helical anchors 554, 556 is shown in FIGS. 49A and 49B. In this embodiment, elongate tensile member 552 is initially comprised of two suture segments 552a, 552b. As with the other embodiments this may be USP No. 2 suture. As in the previous embodiments, a crimp member 558, 560 may be associated with each compressible, helical anchor 554, 556 or the respective tensile member segments 552a, 552b may be connected with anchors 554, 556 in another suitable manner. The two tensile member segments 552a, 552b are threaded through a central crimp member 562 after being introduced through respective tendon segments 564, 566 preferably through respective proximal and distal windows in the tendon as described above. Tensile member segments 552a, 552b are pulled taut through central crimp member 562. This simultaneously compresses helical anchors 554, 556 and pulls tendon segments 564, 566 together to a repair position as shown in FIG. 49B. At this time, a conventional running suture 568, or optionally an adhesive or other acceptable method, may be used to connect tendon segments 564, 566 together at the repair site.

Figure 50:
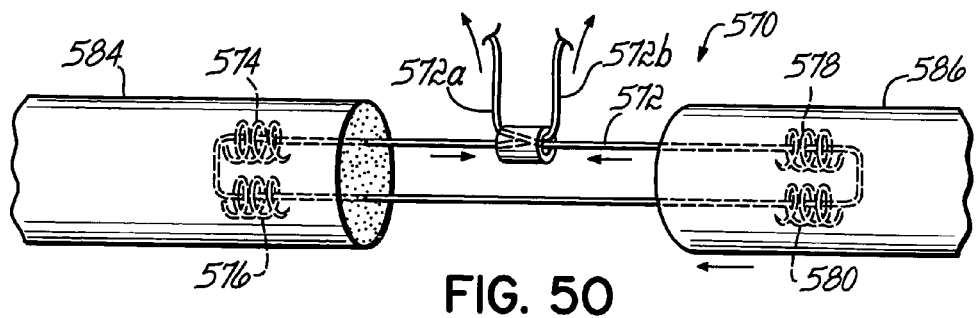
FIG. 50 is a perspective view of another alternative embodiment employing compressible, helical anchors in accordance with the invention.

Another embodiment of a tendon repair apparatus 570 is shown in FIG. 50. Apparatus 570 utilizes an elongate tensile member 572, such as a suture comprised of one suture segment looped through a plurality of, for example, four compressible, helical anchors 574, 576, 578, 580. In this embodiment, separate crimp members at each helical anchor may be eliminated as the suture itself will pull each of the helical anchors 574, 576, 578, 580 to a compressed position as the two suture ends 572a, 572b are pulled through central crimp member 582. As in the embodiment of FIGS. 49A and 49B, pulling the two ends 572a, 572b through central crimp member 582 will simultaneously compress each helical anchor 574, 576, 578, 580 and bring tendon segments 584, 586 together to a repair position at which points ends 572a, 572b may be cut and a running suture or other final attachment method may be employed by the surgeon to complete the repair.

Figure 51A:
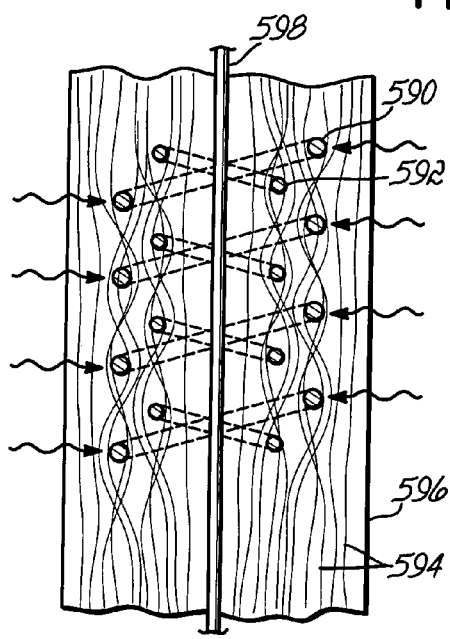
FIG. 51A is a partially sectioned view of another alternative tendon repair apparatus employing electromagnetic impulse energy to collapse one helical member onto another and showing the uncollapsed condition.
Figure 51B:
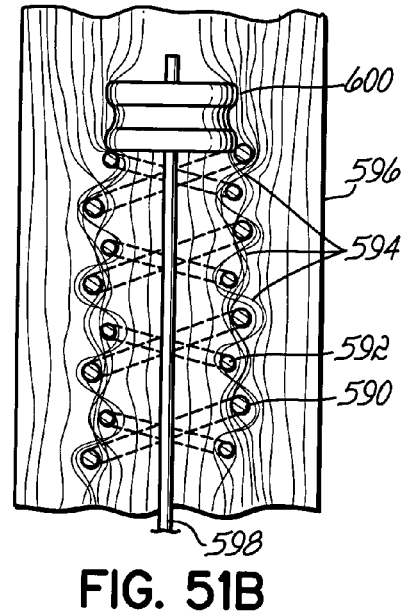
FIG. 51B is a partially sectioned view similar to FIG. 51A, but showing the collapsed condition of the outer helical member and the attachment of a locking member within a tendon.
Figure 52:
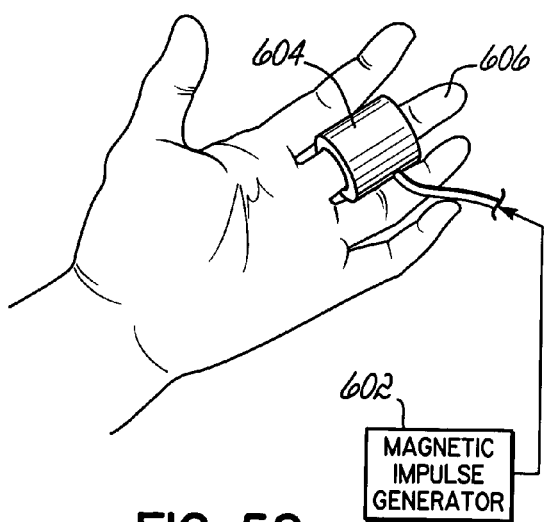
FIG. 52 is a schematic, perspective view showing a magnetic impulse generator operatively connected to a patient's finger for generating the required electromagnetic impulse in the embodiments of FIGS. 51A and 51B.

FIGS. 51A, 51B and 52 illustrate an alternative manner of employing helical anchors to connect a repair apparatus to tendons and ligaments. Specifically, this system employs first and second helical members 590, 592 with at least one of the helical members 590, 592 being movable toward the other to trap and compress tendon or ligament fibers 594 of the tendon or ligament 596 therebetween. As with other embodiments of the invention, a suitable locking member, such as a crimp member 600, may be used to connect elongate tensile member 598 for movement with anchor members 590, 592 such that tendon segment 596 may be pulled and placed under tension with elongate tensile member 598. In the specific embodiment shown in FIGS. 51A, 51B and 52, a magnetic impulse generator 602 is connected with a magnetic impulse supply unit 604 disposed around the patient's finger 606. Analogous systems are available from Maxwell Magneform® in San Diego, Calif. When a magnetic impulse or impulses are supplied with generator 602 this will collapse first helical member 590 onto second helical member 592. To accomplish this, for example, first helical member or outer helical member 590 may be formed from a magnetic metal material, while second helical member or inner member 592 is formed from a non-magnetic material and, therefore, does not deform through the application of an electromagnetic impulse. As with several other embodiments of this invention, this again employs the general technique of providing two portions of a tendon or ligament anchor structure with at least one portion being movable toward the other portion to trap and compress tendon or ligament fibers therebetween. Furthermore, prior to crimping of member 600, crimp member 600 may be moved along elongate tensile member 598, after collapsing outer helical member 590 such that tendon segment 596 is moved to the appropriate repair position at which point the surgeon may crimp member 600 to retain tendon segment 596 at the repair position.

Figure 51C:
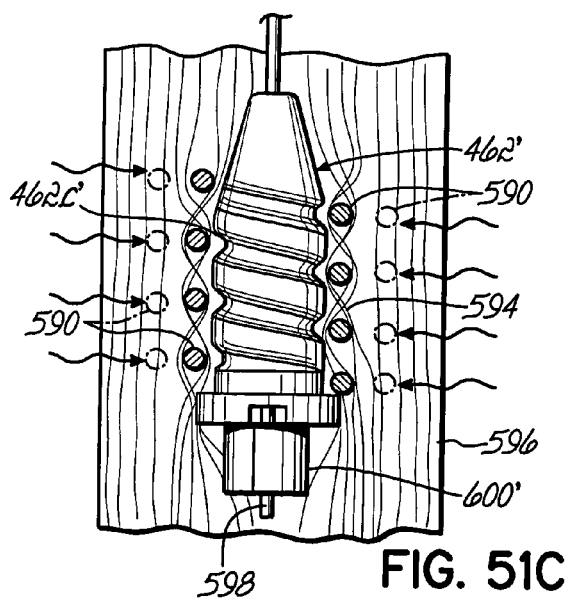
FIG. 51C is a partially sectioned view similar to FIG. 51B, but illustrating an alternative embodiment having a solid or non-helical inner retaining member.

FIG. 51C illustrates another alternative embodiment similar in concept to the embodiment of FIGS. 51A and 51B. In this embodiment, however, an inner retaining member 462' can comprise a solid core member, as opposed to a helical member. Retaining member 462' can be formed of absorbable or non-absorbable materials. Retaining member 462' is preferably threaded over elongate tensile member 598 after insertion of outer helical member 590 within tendon 596. Initially, outer helical member 590 is in an uncollapsed or expanded state, as shown in phantom lines, and receives both elongate tensile member 598 and retaining member 462'. After insertion of retaining member 462', one or more electromagnetic impulses are applied to collapse outer helical member 590 generally to the position shown in solid lines thereby compressing tendon fibers 594 between outer helical member 590 and inner retaining member 462'. As further shown, retaining member 462' may include an outer discontinuous surface, such as a convoluted or threaded surface 462c' to help retain, grip or otherwise engage fibers 594. As necessary, a locking member 600' may be crimped or otherwise locked onto elongate tensile member 598 and against retaining member 462' to lock the anchor structure, comprising retaining member 462' and helical member 590, to elongate tensile member. It will be appreciated that locking member 600' may not be necessary in any given application of the inventive concepts.

Figure 53A:
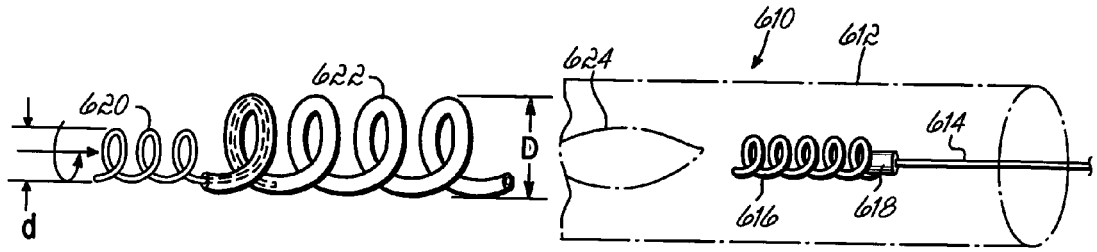
FIG. 53A is a schematic, perspective view showing another alternative embodiment of a tendon repair apparatus employing a collapsible helical member.
Figure 53B:
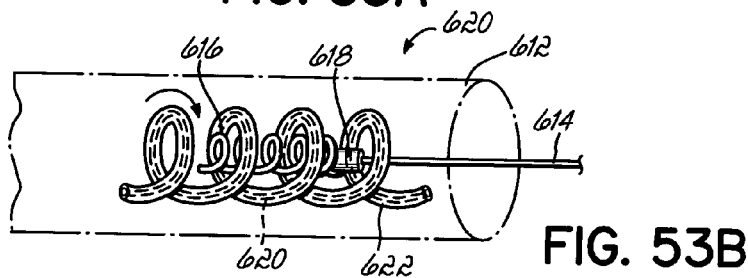
FIG. 53B is a schematic perspective view showing an intermediate step in the application of the collapsible helical member within the tendon.
Figure 53C:
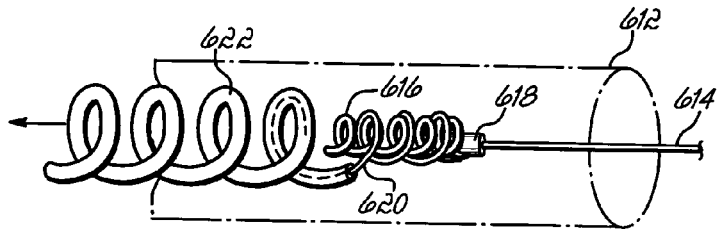
FIG. 53C is a schematic perspective view similar to FIG. 53B, but showing a subsequent step with the collapsible helical member being collapsed onto another helical member to compress tendon fibers therebetween.

FIGS. 53A-53C illustrate another alternative embodiment of a repair apparatus 610 employing generally similar concepts to the embodiment of FIGS. 51A and 51B. Specifically, in FIG. 53A, apparatus 610 is employed in a tendon segment 612 and again includes an elongate tensile member 614 connected with a first helical member 616 by a suitable connector 618. A second helical member 620 is initially contained in a hollow, helical carrier 622. Carrier 622 has a diameter "D" which is greater than the diameter "d" of second helical member 620. Thus, as second helical member 620 is rotated into carrier 622, member 620 elastically expands to the shape of carrier 622 and is therefore initially disposed or carried at a diameter "D". As further shown in FIG. 53B, as carrier 622 and second helical member 620 are rotated into tendon segment 612 through an access incision 624, carrier 622 is rotated over first helical member 616. As further shown in FIG. 53C, as carrier 622 is counter-rotated or rotated in a reverse direction, second helical member 620 is left behind and resiliently contracts or compresses around first helical member 616 thereby trapping tendon fibers (not shown) between member 616 and member 620. It may be necessary for the surgeon to hold second helical member 620 stationary while counter-rotating carrier 622 as shown in FIG. 53C. Upon removal of carrier 622, elongate tensile member 614 will be effectively connected to tendon segment 612 and may be placed under tension while, for example, pulling tendon segment 612 to a repair position as previously described.

Figure 54:
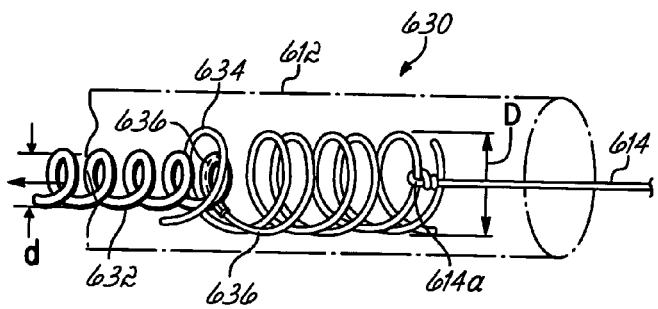
FIG. 54 is another alternative embodiment similar to the embodiment of FIGS. 53A-53C, but schematically illustrating an expandable helical member for trapping tendon fibers with another helical member.

FIG. 54 illustrates an alternative embodiment of an apparatus 630 essentially employing a reverse technique as compared to the embodiment of FIGS. 53A-53C. In this embodiment, a hollow, helical carrier 632 has a smaller outer diameter "d", than the respective diameters "D" associated with first and second helical members 634, 636. Elongate tensile member 614 may be suitably connected to first helical member 634, such as through the use of a suture knot 614*a*. In this embodiment, first helical member 634 is rotated into tendon segment 612 in one of the previously described manners and, similarly, carrier 632, which contains second helical member 636 in a resiliently compressed state is rotated into the center of first helical member 634. With second helical member 636 held stationary, helical carrier 632 is counter-rotated, as shown in FIG. 54, leaving second helical member 636 to resiliently expand to its normal diameter "D" thereby trapping tendon fibers (not shown) between first and second helical members 634, 636. With carrier 632 removed, and helical members 634, 636 securely affixed to the tendon fibers, elongate tensile member 614 may be placed under tension and used to pull tendon segment 612 to a repair position as previously described. It should be appreciated that the respective diameters of helical members 616, 620 and 634, 636 may vary within the same anchor system. That is, helical anchor 616 may be slightly smaller or larger than helical anchor 620 and helical anchor 634 may be slightly smaller or larger than helical anchor 636 while retaining the ability to trap tendon fibers therebetween. Again, each of these anchor structures employ at least one moveable anchor portion to trap fibers between itself and another anchor member.

Figure 55:
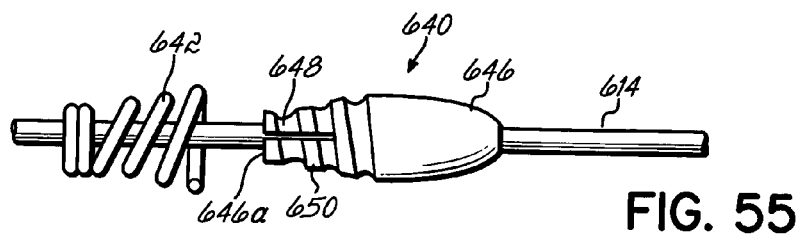
FIG. 55 is a fragmented plan view showing another tendon repair apparatus employing a collet structure in accordance with the invention.

FIG. 55 illustrates another alternative apparatus 640 comprised of a helical anchor 642 and elongate tensile member 644 and a retaining member 646. These three elements operate together similar to previous embodiments in that helical anchor 642 and retaining members 646 are each initially slidable along elongate tensile member 644. Elongate tensile member 644 may again be a flexible suture, semi-flexible or rigid tensile member. In this embodiment, retaining member 646 acts as a collet structure and includes one or more slots 648 extending from a leading end 646*a*. Also, retaining member 646 may include a discontinuous outer surface 650, such as a surface having a generally threaded configuration. It will be appreciated that, as retaining member 646 is rotated into helical anchor 642, tendon or ligament fibers (not shown) will be trapped between surface 650 of retaining member 646 and the inner surfaces of helical anchor 642. At the same time, the collet structure at the leading end of retaining member 646 will compress due to the slot or slots 648 and will clamp against elongate tensile member 644 to retain the assembly fixed on elongate tensile member 644. Retaining member 646 may be formed of a material that allows the leading end to plastically deform and clamp onto elongate tensile member 644.

Figure 56:
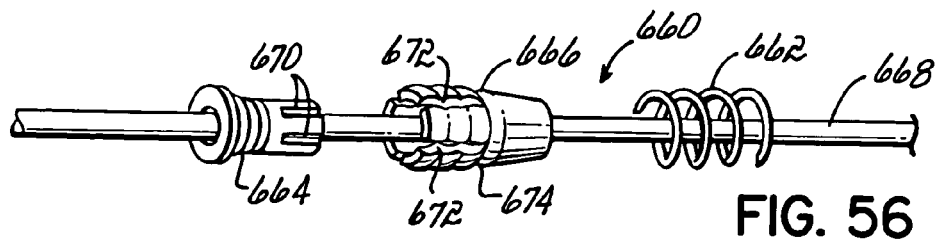
FIG. 56 is a perspective view of another collet-type anchor structure shown in exploded form.
Figure 57:
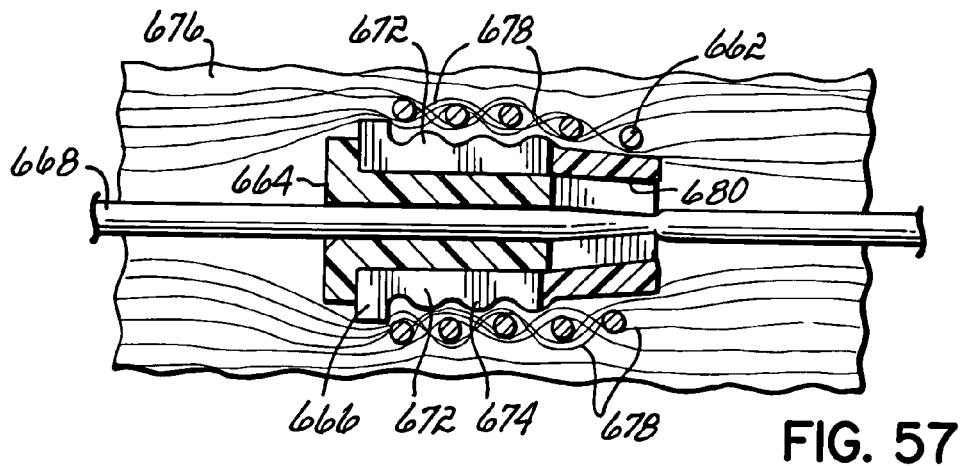
FIG. 57 is a partially sectioned view of the embodiment shown in FIG. 56, but illustrating the assembled condition of this embodiment within a tendon.

A related embodiment utilizing collet-like structure is shown in FIGS. 56 and 57. In this embodiment, an apparatus 660 generally includes a helical anchor 662 and a two-piece retaining member structure comprised of inner and outer retaining elements 664, 666. Anchor 662 and retaining elements 664, 666 are initially slidable along an elongate tensile member 668. One or more slots 670 are formed at a leading end of inner retaining element 664 and one or more slots 672 are formed at a trailing end of outer retaining element 666. Again, an outer surface 674 may be discontinuous to help trap tendon fiber between outer retaining element 666 and helical anchor 662 as described below. A review of FIG. 57 will indicate the function of various elements shown in FIG. 56. More particularly, after helical anchor 662 has been rotated into a tendon segment 676, the surgeon slides inner retaining element 664 into helical anchor 662 to trap tendon fiber 678 between outer surface 674 and helical anchor 662. To lock the assembly into place and to expand outer retaining element 664 to further lock the tendon fiber 678, the surgeon slides inner retaining element 664 or, alternatively, rotates inner retaining element 664 into outer retaining element 666. This simultaneously expands outer retaining element 666 through the action of slots 672 and contracts the leading end of inner retaining element 664 through the action of slots 670 and a tapered inner surface 680 of outer retaining element 666. Thus, in the position shown in FIG. 57, apparatus 660 is ready for use in accordance with the inventive concepts to repair the tendon by placing tendon segment 676 into tension using elongate tensile member 668.

Figure 58:
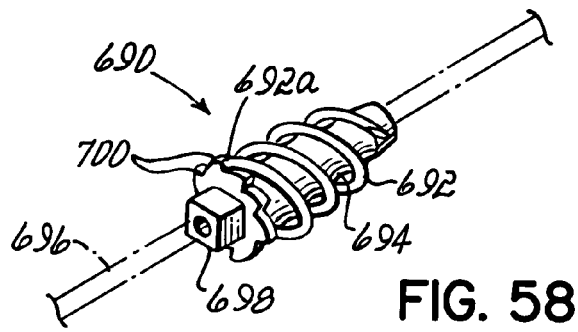
FIG. 58 is a perspective view of another alternative helical anchor and internal retaining member showing a ratchet structure for preventing counter-rotation of the retaining member.

FIG. 58 illustrates an alternative apparatus 690 again employing a helical anchor member 692 and a retaining member 694 each connected for sliding movement along an elongate tensile member 696. Retaining member 694 may again include a drive portion 698 for allowing retaining member 694 to be rotated into helical anchor 692. This embodiment illustrates a manner of preventing counter-rotation or backout of retaining member 694 after installation within a tendon. In this regard, a ratchet structure 700 is disposed at a trailing end portion of retaining member 694 for engaging a trailing end 692*a* of helical anchor 692. As retaining member 694 is rotated into helical anchor 692, ratchet structure 700 will engage trailing end 692*a* to prevent counter-rotation of retaining member 694.

Figure 59:
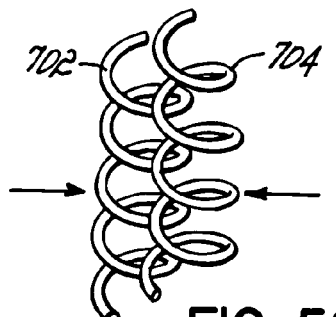
FIG. 59 is a perspective view of another embodiment employing two helical members with interlocking or intermeshing coils.

FIG. 59 illustrates two helical anchors 702, 704 in which the helical coils are interlocked or intertwined. This may be used in the various embodiments of this invention to better interlock the helical anchor structure with the tendon fibers. For example, while one helical anchor 702 may be initially rotated into the tendon and, subsequently, the second helical anchor 704 may be rotated in an interlocking fashion with the first helical anchor 702. The assembly is then used in accordance with the invention, and with one or more elongate tensile members or tensile member segments to place a tendon under tension during a repair as generally described herein. Alternatively, the coils of anchor 702, 704 may interlock in a lateral direction as shown in FIG. 59 without actually having the coils of one anchor rotate into the coils of the other anchor.

Figure 60:
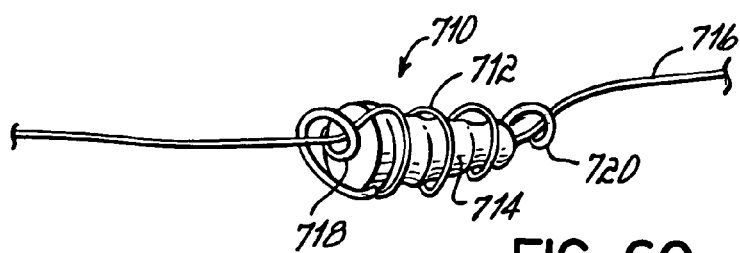
FIG. 60 is a perspective view of another alternative anchor structure employing a flexible helical anchor wrapped around a retaining member.

FIG. 60 illustrates an alternative apparatus 710 in which a flexible helical anchor 712 is wrapped around an internal retaining member 714. Helical anchor 712 may be formed from suture material, for example, that is one in the same with an elongate tensile member 716 used in accordance with the inventive concepts or which is separate from an elongate tensile member which may extend through a central longitudinal aperture (not shown) within retaining member 714.

Leading and trailing hook members 718, 720 may be provided for guiding helical anchor 712 at the ends of retaining member 714.

Figure 61:
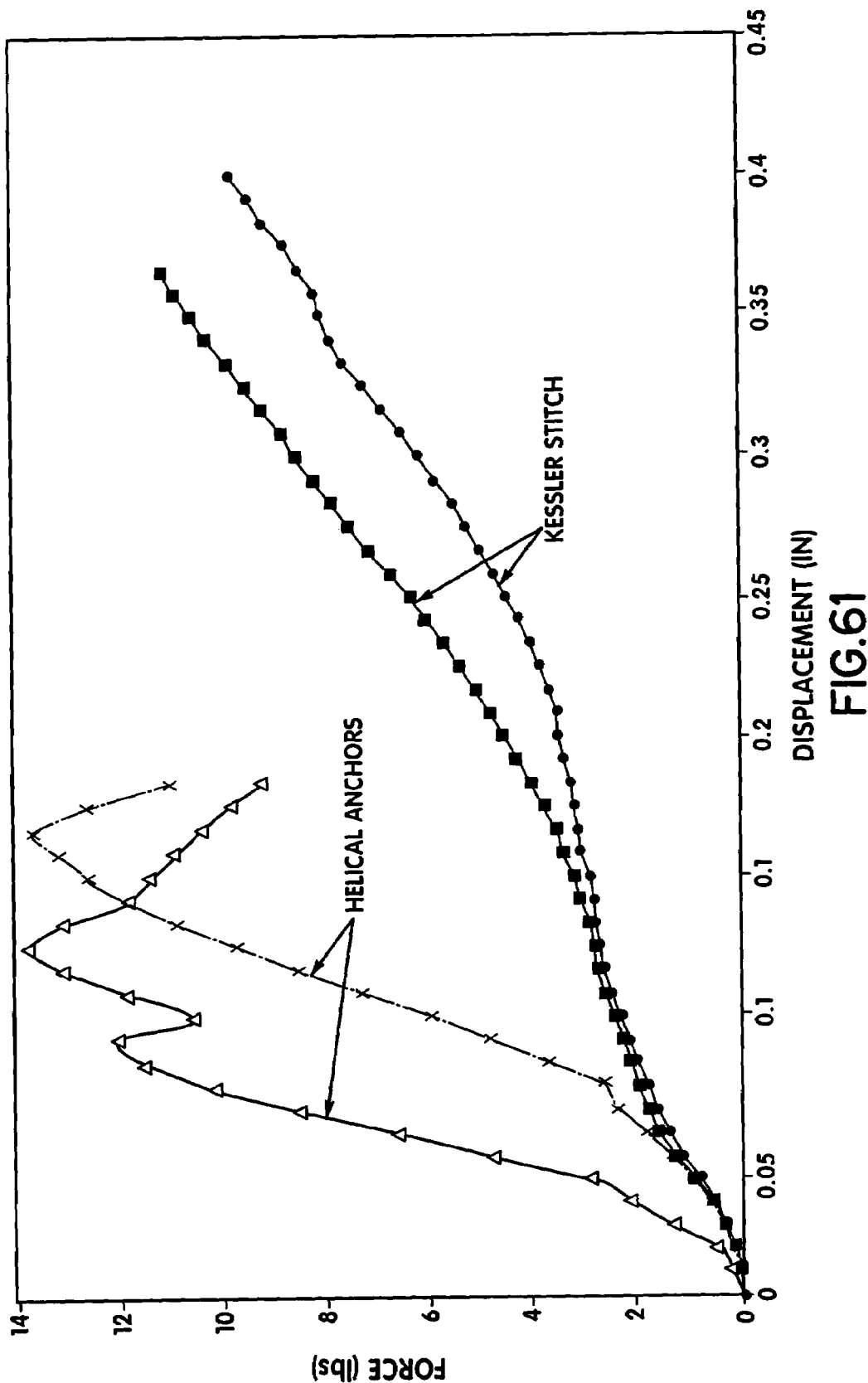
FIG. 61 is a graph illustrating a force/displacement curve comparing a helical anchor repair apparatus of the invention against a conventional Kessler repair technique.

FIG. 61 illustrates force vs. displacement curves for helical anchor apparatus of the present invention as compared to conventional Kessler repair techniques. The helical anchor repair apparatus represented in FIG. 61 corresponds with the embodiment of FIG. 37B. The Kessler stitch techniques were performed with 3-0 Vicryl sutures and each repair was placed in porcine tendon of approximately 5 mm diameter. The graph demonstrates that the Kessler stitches allow displacement or gapping between the tendon segments at low levels of tensile force as compared to the helical anchor structures and elongate tensile member of the present invention. In other words, the helical anchors of the present invention will sustain much higher levels of tensile force without significant amounts of gapping occurring between the tendon ends as compared to the Kessler stitch technique. For this reason, a patient who has undergone a repair using the present invention can undergo more immediately and vigorous physical therapy than a patient having a Kessler stitch repair. Ultimately, the patient will experience a quicker recovery time and more mobility proximate the repair site using the present invention.

Figure 62:
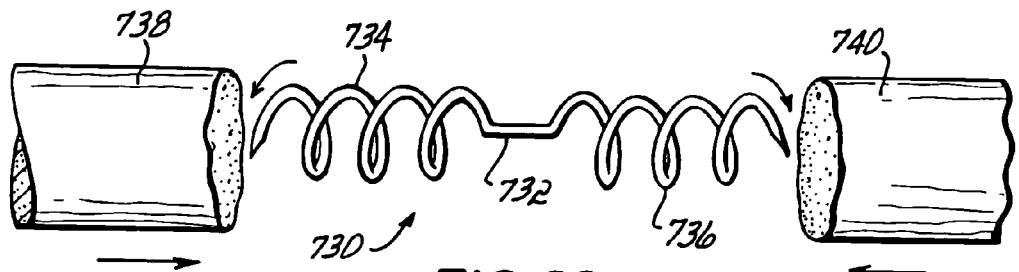
FIG. 62 is a perspective view of another alternative embodiment of the invention employing two helical anchors integrated with an elongate tensile member.

FIG. 62 illustrates an alternative embodiment of the invention wherein an integral apparatus 730 comprises a tensile member 732 and opposite helical anchors 734, 736. Anchors 734, 736 are coiled in opposite directions such that rotation of apparatus 730 in a single direction will cause helical portions 734, 736 to each rotate into respective opposed tendon segments 738, 740. Apparatus 730 may be formed with various degrees of rigidity or flexibility suitable for the repair site. Retaining members (not shown) in accordance with the invention may be used to hold anchors 734, 736 securely to the tendon tissue.

Figure 63:
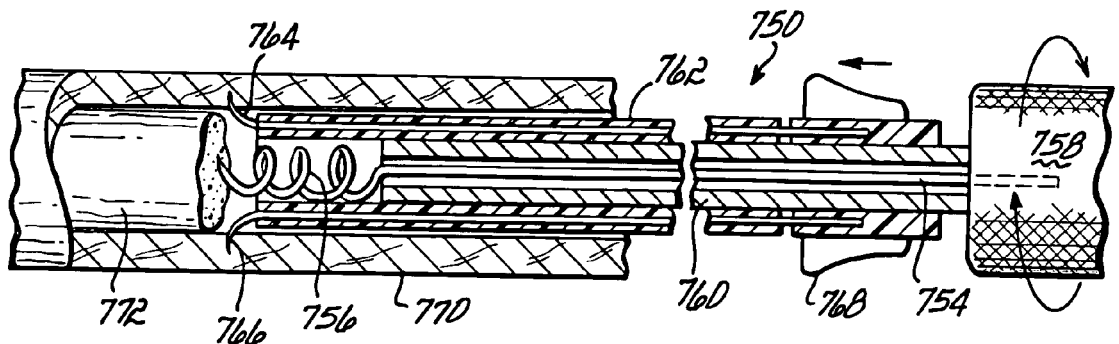
FIG. 63 is a partially sectioned view of a tendon retrieval device constructed in accordance with the invention.
Figure 64:
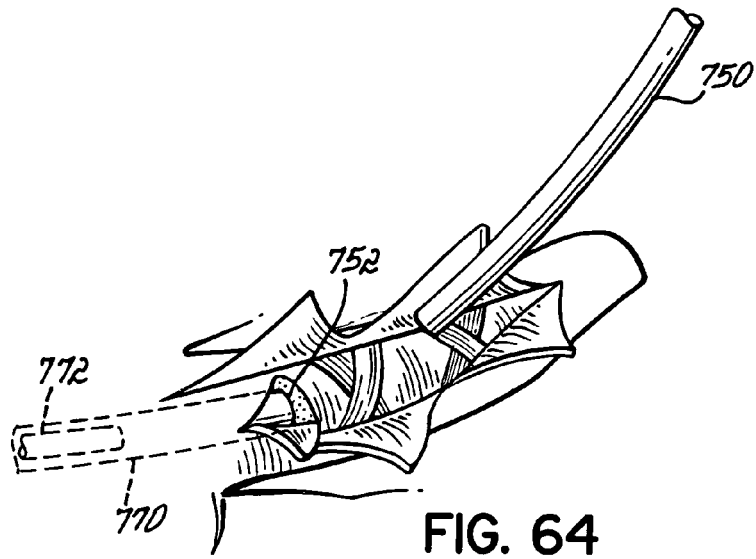
FIG. 64 is a perspective view showing use of the retrieval device of FIG. 63.

The concepts employed in the helical anchor based repair apparatus of the present invention may also be employed in a tendon retrieval device 750 as, for example, shown in FIGS. 63 and 64. Retrieval device 750 may be inserted into a tendon sheath through a window 752, which may be triangular-shaped as previously described. Retrieval device 750 more specifically comprises a rotatable shaft or rod 754 having a helical retrieving member 756 at one end and a rotatable knob 758 connected at an opposite end. Shaft or rod 754 is contained within a hollow inner core 760 which, in turn, is contained within an outer core 762. Anti-rotation members 764, 766 are preferably provided within hollow outer core 762 and may be actuated from non-operative positions to the operative positions shown in FIG. 63. This is accomplished by reciprocating a knob 768 back and forth. When knob 768 is moved to the left, as viewed in FIG. 63, this extends anti-rotation members 764, 766 into the tendon sheath 770 to prevent rotation thereof as rotatable knob 758 is subsequently rotated and moved inwardly to rotate helical member 756 into tendon end 772. Once helical member 756 is fully rotated into tendon end 772, knob 758 may be pulled to the right, as viewed in FIG. 63, to retrieve tendon end 772.

Figure 65:
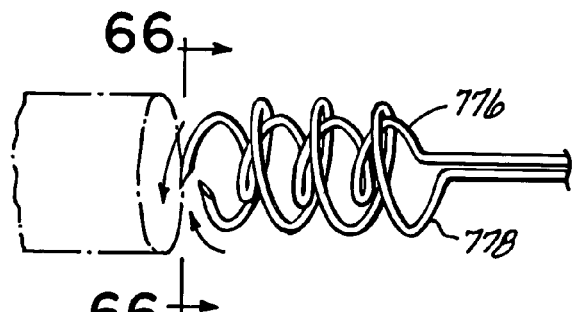
FIG. 65 is a perspective view illustrating an alternative double helix embodiment useful in the tendon retrieval device of this invention.
Figure 66:
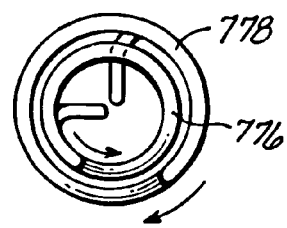
FIG. 66 is an end view taken along line 66-66 of FIG. 65.

It will be appreciated that retrieval device 750 may be modified in many different manners consistent with the concepts disclosed herein. As one example, device 750 may further include an internal retaining member which may be inserted into helical member 756 to retain tendon fibers therebetween as previously discussed above with respect to tendon-to-bone and tendon-to-tendon repair apparatus. Another potential alternative is shown in FIGS. 65 and 66 in which inner and outer helical retrieving members 776, 778 are employed to counter-rotate into tendon end 772. Suitable actuation structure (not shown) will be employed to counter-rotate helical members 776, 778, thereby eliminating tendon rotation while the retrieval device is attaching to the tendon end 772.

Figure 67:
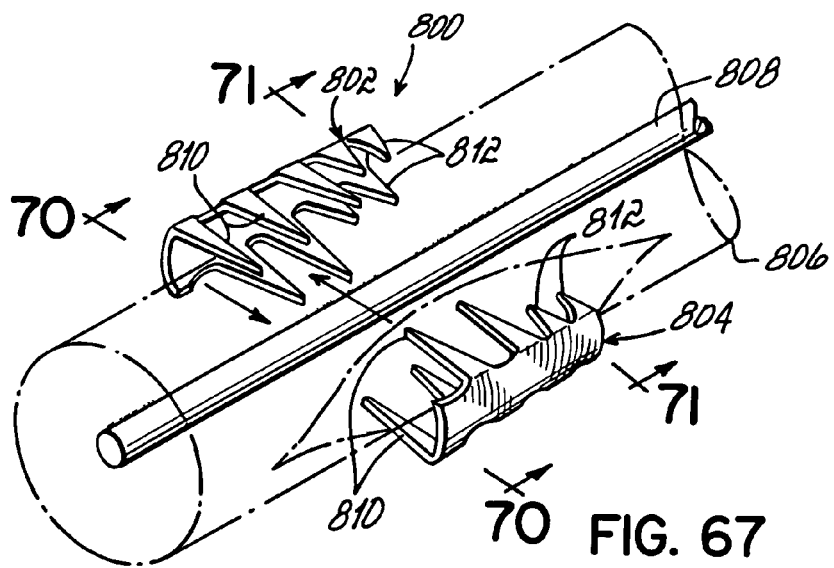
FIG. 67 is a perspective view illustrating another alternative anchor structure employing two crimpable anchor members, and an elongate tensile member.

FIGS. 67-71 illustrate another alternative embodiment of the present invention employing analogous concepts to previous embodiments wherein at least one portion of an anchor structure moves with respect to another to a position at which tendon fibers are trapped between the portions and the anchor structure is affixed to an elongate tensile member. In particular, an apparatus 800 is shown and comprises a pair of anchor members 802, 804 which may be crimped together and simultaneously crimped within a tendon 806 and securely against an elongate tensile member 808, such as a suture or other tensile member as described above. Each anchor member 802, 804 includes respective long legs 810 and respective short legs 812 that register together in alternating fashion when in opposed relation as shown in FIG. 67 and as shown being applied through opposite access incisions 814, 816 in FIG. 69.

Figure 68:
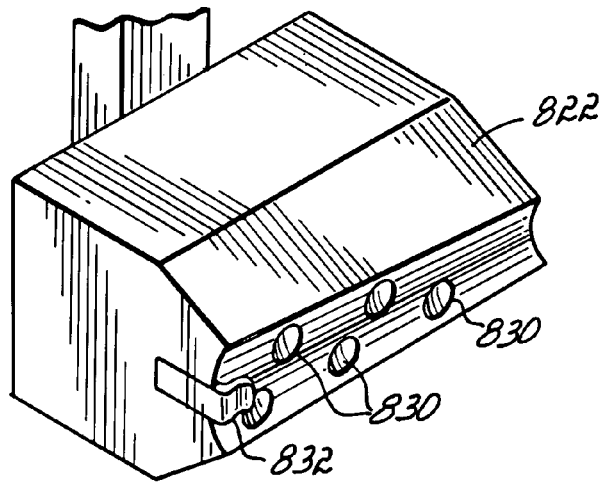
FIG. 68 is a perspective view of a portion of a tool used to apply the anchor structure shown in FIG. 67.
Figure 69:
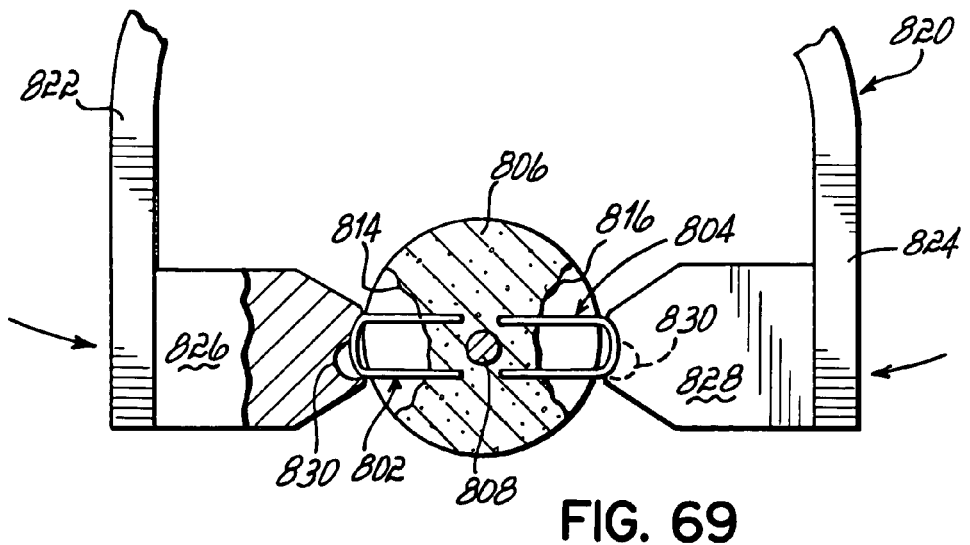
FIG. 69 is a partially sectioned view illustrating the use of the tool to crimp the anchor members onto a tendon and the elongate tensile member.
Figure 70:
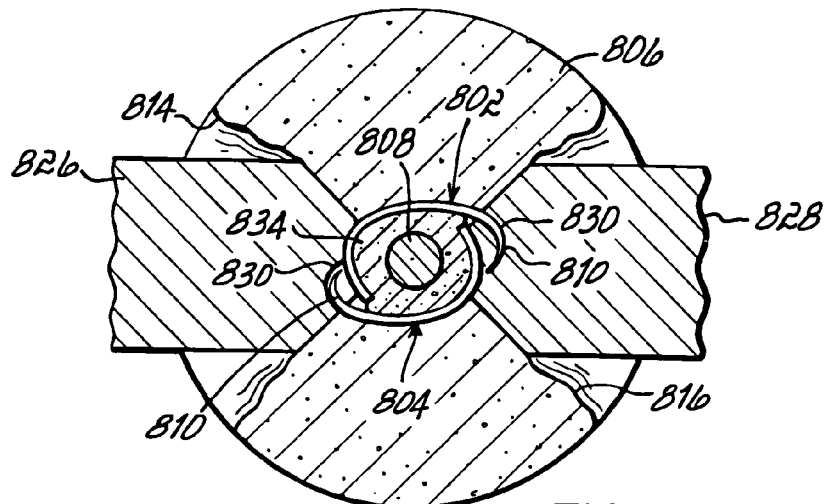
FIG. 70 is a sectional view taken generally along line 70-70 of FIG. 67, but illustrating the crimped or deformed condition of the crimp members on the tendon tissue.
Figure 71:
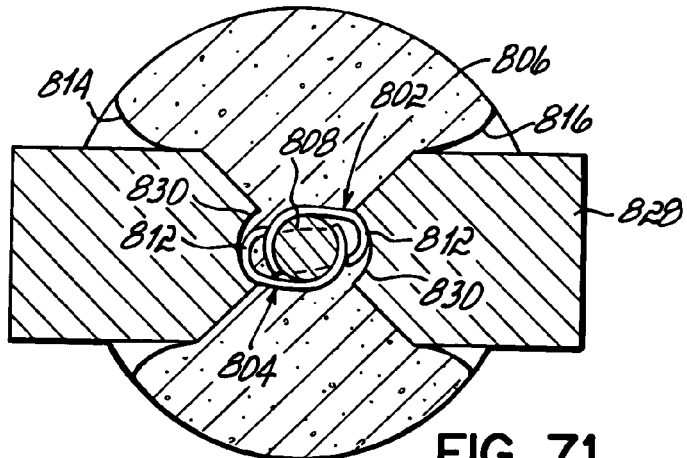
FIG. 71 is a sectional view taken generally along line 71-71 of FIG. 67, but illustrating the crimped or deformed condition of the crimp members locked onto the elongate tensile member.

FIGS. 68 and 69 illustrate a tool 820 having a pair of movable jaws 822, 824 used to apply anchor members 802, 804 to tendon 806. Jaws 822, 824 include respective grippers 826, 828 for holding anchor members 802, 804 in opposed relation as shown in FIG. 69. As further detailed in FIG. 68, each jaw 822, 824 includes pockets 830 that align with the ends of the legs 810, 812 of the opposed anchor member 802 or 804. A clip 832, or other structure, may be provided to retain anchor member 802 and 804 in place until the crimping operation is complete. As shown in FIGS. 70 and 71, as jaws 822, 824 and grippers 826, 828 are brought together from the position shown in FIG. 69 to the position shown in FIGS. 70 and 71, legs 810, 812 will be deformed or crimped permanently into the position shown by respective pockets 830. At the locations proximate longer legs 810, this will lock anchor members 802, 804 to the tendon tissue 834 and, more specifically, to the tendon fibers comprising tissue 834. At the area of proximate short legs 812, anchor members 802, 804 will be crimped more directly onto elongate tensile member 808. This action is brought about by the tapered angle of grippers 826, 828 as illustrated in FIG. 68 and by comparing FIGS. 70 and 71 which show the grippers in the same actuated position.

In this embodiment, tool 820 may be actuated to a first position sufficient to grip tendon fibers 834, but still allow sliding motion along elongate tensile member 808. Using tool 820, or another method, tendon 806 may then be pulled to a repair position by sliding anchor members 802, 804 along elongate tensile member 808. At the appropriate repair position, the crimp may be finished by further actuating tool 820 to the position shown in FIGS. 70 and 71. In a tendon-to-tendon repair, as with the previous embodiments, one pair of anchor members 802, 804 may be rigidly affixed to tendon 806 in the manner illustrated in FIGS. 70 and 71, on one side of a tear, and the sliding adjustment may be accomplished in the opposite side of the tear followed by a final crimping action on a second set of anchor members 802, 804 as described above.

Figure 72:
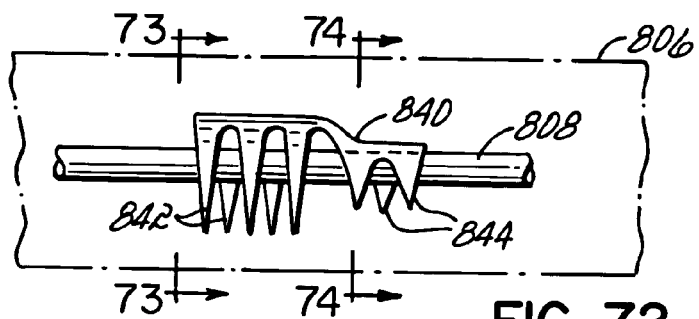
FIG. 72 is a plan view illustrating an alternative crimp-type anchor structure employing a single crimp member and elongate tensile member.
Figure 73:
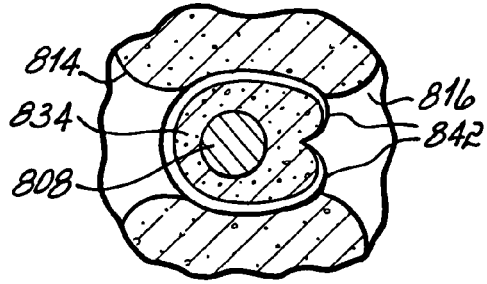
FIG. 73 is a sectional view taken generally along line 73-73 of FIG. 72, but illustrating the crimped or deformed condition of the crimp member onto the tendon tissue and around the elongate tensile member.
Figure 74:
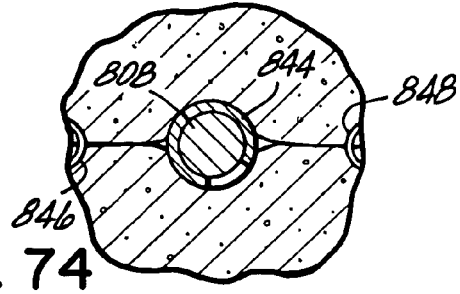
FIG. 74 is a sectional view taken generally along line 74-74 of FIG. 72, but illustrating the crimped or deformed condition of the crimp member onto the elongate tensile member.

FIGS. 72-74 illustrate another apparatus similar to FIGS. 67-71, but employing a single anchor member 840 having respective long and short legs 842, 844. The operation of this embodiment is similar to the previous embodiment, except that only one of the opposed jaws would require an anvil surface, such as one comprised of recesses or pockets, in order to bend legs 842 into a position suitable for tightly gripping tendon tissue 834 against elongate tensile member 808 and also tightly deforming legs 844 substantially directly against elongate tensile member 808 as shown in FIG. 74.

Again, this embodiment comprises an anchor structure having an anchor member 844 with at least one portion movable with respect to another for gripping and compressing tendon tissue therebetween. Furthermore, before the final crimping action takes place, anchor member 840 can initially grip tissue 834 and move along elongate tensile member 808 to a suitable repair position where upon the surgeon may finally crimp anchor member 840 securely against elongate tensile member 808 as shown in FIG. 74. As further shown in FIG. 74, each access incision 814, 816 is then closed using stitches 846, 848 or another suitable method.

Figure 75:
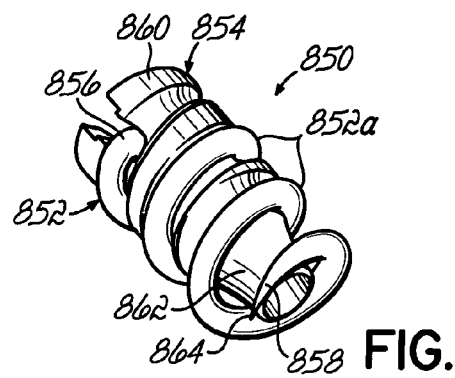
FIG. 75 is a perspective view of a unitary anchor assembly comprised of a helical anchor coupled for insertion with a core portion or tendon fiber retaining member.
Figure 76:
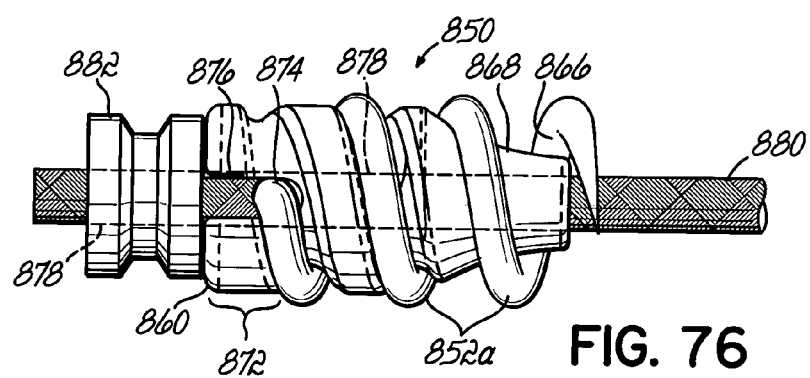
FIG. 76 is a plan view showing the unitary anchor assembly of FIG. 75 carried on an elongate tensile member and including a crimp member at a proximal end thereof.

Referring now to FIGS. 75 and 76, another embodiment of the invention is described in connection with tendon-to-tendon or ligament-to-ligament repair, however, it will be appreciated that this embodiment will also be useful for other procedures. In this embodiment, an anchor assembly 850 is comprised of a helical anchor 852 and a core portion or tendon fiber retaining member 854. Helical anchor 852 has proximal and distal ends 856, 858 and retaining member likewise has proximal and distal ends 860, 862. The distal end 858 of helical anchor 852 extends distally beyond the distal end 862 of retaining member 854 and is sharpened to a point 864 to aid in insertion. In addition, retaining member 854 is tapered at its distal end 862 creating a space 866 between coils 852a of the helical anchor 852 and the outside surface 868 of the retaining member 854 for receiving and retaining tendon or ligament fibers 870 therein at least at a location near distal ends 858, 862. The proximal end 856 of helical anchor 852 is fixed to a proximal end portion 872 of retaining member 854. This may be accomplished in various ways, however, in the preferred embodiment, the proximal end 856 is retained in a slot 874 and is welded such as through a laser or resistence welding operation. The proximal end 860 of retaining member 854 includes a slot 876 for receiving an insertion tool and, if necessary, a removal tool to be described below. Slots 874, 876 may communicate with each other as shown. Retaining member 854 includes a central longitudinal bore 878 for receiving an elongate, preferably flexible, tensile member 880. Finally, a crimp member 882 is provided and may be a separate member with a central bore 884 for receipt on elongate flexible tensile member 880 or, as previously described, it may be integral with retaining member 854 or a different type of locking member may be used instead.

Figure 77:
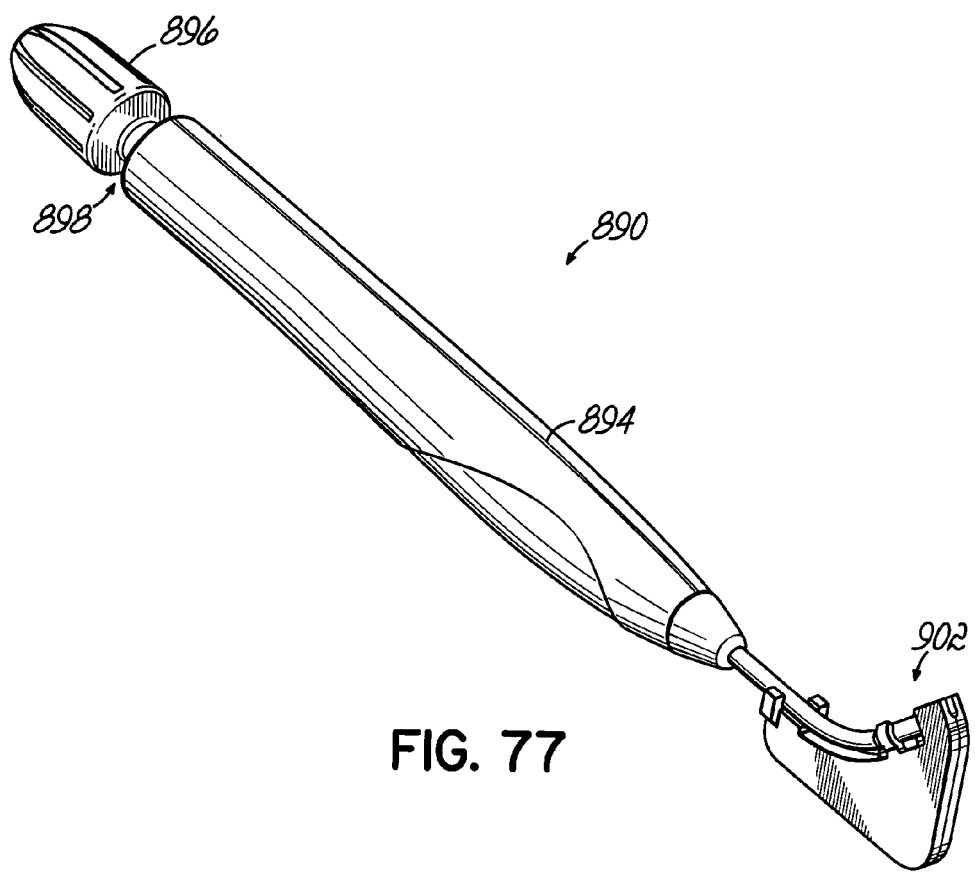
FIG. 77 is a perspective view showing an insertion tool for inserting the assembly of FIG. 75 into a tendon or ligament.
Figures 78, 78A:
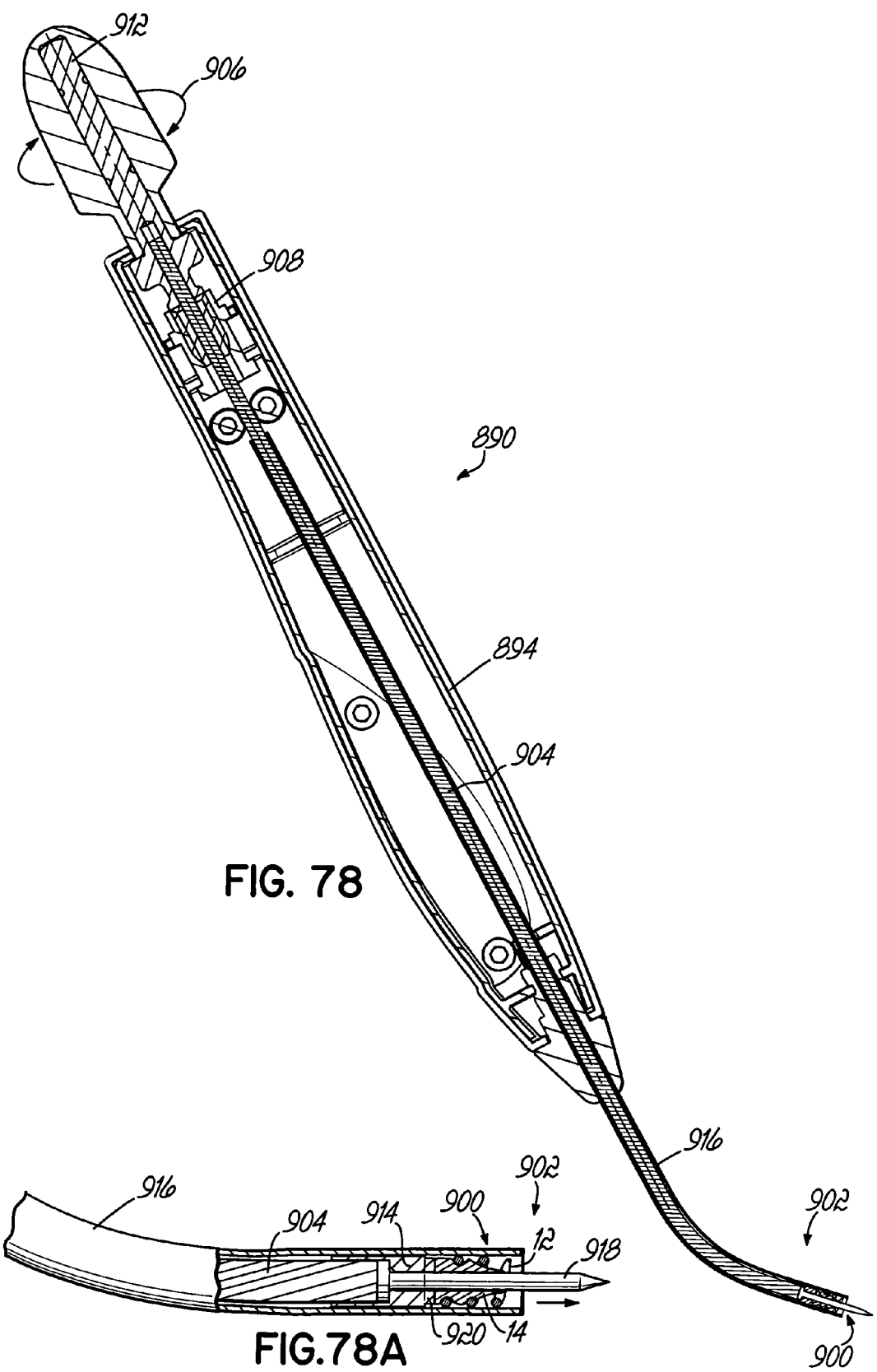
FIG. 78 is a cross sectional view generally taken along the longitudinal axis of the insertion tool shown in FIG. 77.
FIG. 78A is an enlarged view, partially cross sectioned, of the distal end of the tool shown in FIG. 78.

FIGS. 77, 78 and 78A illustrate an anchor assembly insertion tool 890 for inserting the anchor assembly 850 of FIG. 75 within a tendon or ligament 892. Insertion tool 890 comprises an elongate body portion 894 having a rotatable knob 896 at a proximal end 898 and having a needle-shaped drive portion 900 at a distal end 902. A flexible cable or shaft 904 is coupled between knob 896 and needle-shaped drive portion 900 and, in the preferred embodiment, this cable 904 is both rotated and translated as knob 896 is rotated in the direction of arrows 906. A threaded coupling 908 within the elongate body portion 894 allows the simultaneous rotation and translation around and along axis 912 as knob 896 is rotated. Needle-shaped drive portion 900 is rigidly affixed to flexible cable 904 as shown in FIG. 78A through the use of a coupling member 914 and, preferably, an anchor assembly 850 as shown in FIG. 75 is retained within a curved, tubular housing 916 which does not rotate but retains rotatable cable 904 therein. Needle-shaped drive portion 900 includes a needle 918 which extends through anchor assembly 850 and further includes a projecting portion 920 which is complimentary to the tool engaging slot portion 876 of anchor assembly 850 and fits therein to allows rotation and translation of assembly 850 as the needle 918 is both rotated and translated into the tendon or ligament in the direction of arrow shown in FIG. 78A. As more specifically shown in FIG. 79, anchor assembly 850 is rotated and translated, or moved axially, into a tendon or ligament 892 and fibers 870 are captured during this insertion process between the coils 852a of anchor 852 and the outside surface 868 of retaining member 854. During the insertion process, the coils 852a expand slightly outward away from the outer surface 868 of retaining member 854 due to their inherent spring action and, also due to their spring action, spring back to apply a force against the tendon or ligament fibers 870 and against the outer surface 868 of the retaining member 854. This forcefully traps fibers 870 and strengthens the connection between anchor assembly 850 and the tendon or ligament fibers 870.

FIGS. 80 and 80A illustrate a pistol grip device 940 for driving the shaft 904 of the tool 890 as generally shown in FIGS. 77 and 78. Device 940 replaces knob 896 to allow one-handed operation by a surgeon. In this embodiment, a firing lever 942 may be actuated toward a handle 944 with a single hand of the surgeon to rotate the firing lever 942 about a pivot 946 and thereby drive a rack gear 948 upwardly, via a connecting pin 948a, to rotate a pinion gear 950 coupled for rotation with flexible shaft 904. In this embodiment, shaft 904 includes an externally threaded portion 904a and an internally threaded nut 952 is rigidly affixed, so as not to rotate, within device 940. Threaded portion 904a engages the internal threads of nut 952 and as shaft 904 rotates through the interaction of rack and pinion 948, 950, shaft 904 also translates to the left, as viewed in FIG. 80, to move drive portion 900 and anchor assembly 850 (FIG. 78A) into tendon or ligament 892. Alternatively, if a translation mechanism were not provided, the surgeon could translate the anchor assembly 850 manually into the tendon or ligament 892 by simultaneously pushing the pistol grip handle assembly 940 while actuating the firing lever 942. Other forms of pistol grip or other one-handed actuators may be used and configured in any number of ways by those of ordinary skill to simultaneously rotate and, optionally, translate shaft 904.

Figure 81:
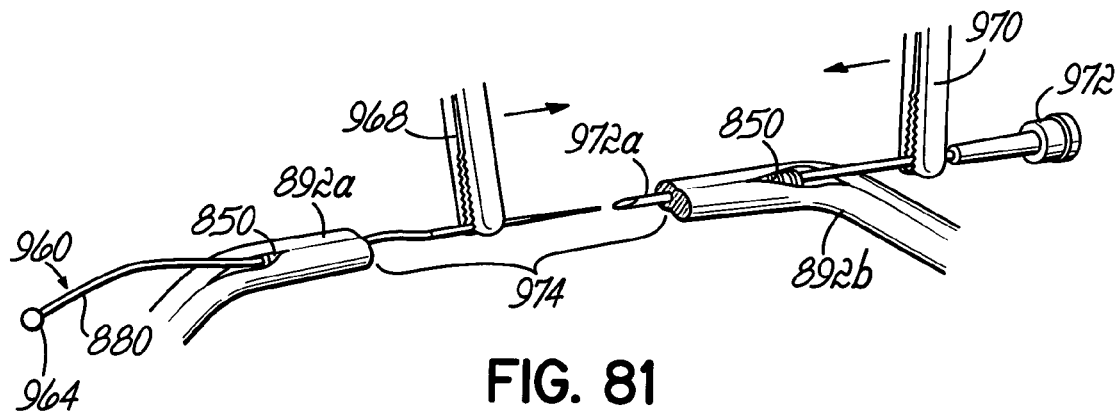
FIGS. 81-87 are perspective views illustrating a tendon or ligament repair method utilizing two unitary anchor assemblies and an elongate, flexible tensile member.
Figure 82:
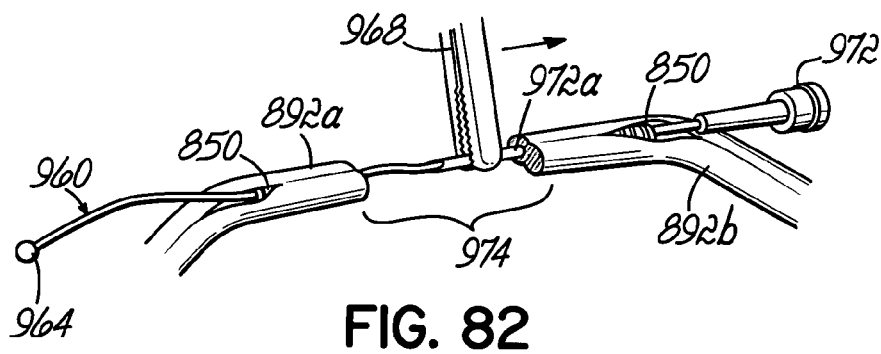
Figure 83:
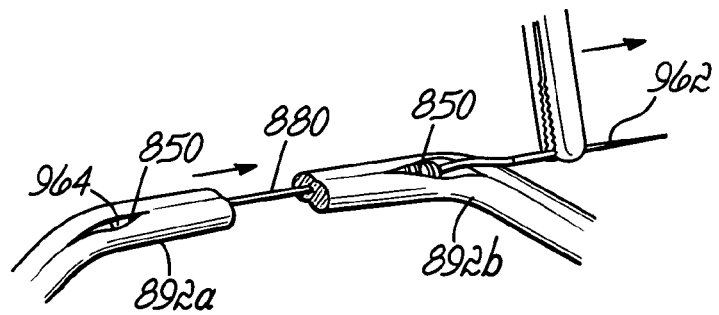

FIGS. 81-87 illustrate one preferred method out of many possible methods for utilizing anchor assembly 850 of FIG. 75. In this regard, two anchor assemblies 850 are respectively driven into tendon or ligament segments 892a, 892b as shown in FIG. 81 and in a manner such as described above. An assembly 960 comprised of a distal needle 962 coupled with a flexible elongate tensile member 880, such as a multifilament suture, and a preset crimp member 964 crimped onto a proximal end 966 of elongate tensile member 880 is threaded through a first one of the anchor assemblies 850 using a tool 968 until needle 962 is positioned between tendon or ligament segments 892a, 892b as shown in FIG. 81. From the opposite side, a second tool 970 is used to thread a capturing member, which may be a conventional syringe or vena-puncture needle 972, through the second anchor assembly 850 and into the space 974 between tendon or ligament segments 892a, 892b. The first needle 962 is then captured by inserting its end into the hollow interior of the syringe needle 972 and the connected assembly is then withdrawn through the second anchor assembly 850 as shown in FIGS. 82 and 83. Alternatively, elongate tensile member 880 may be pushed through the second anchor assembly 850 without first being captured in space 974.

Figure 84:
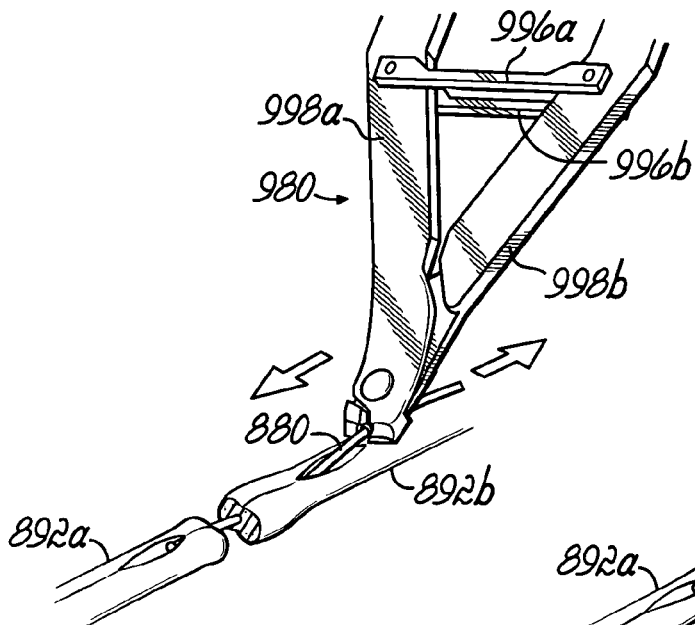
Figure 85:
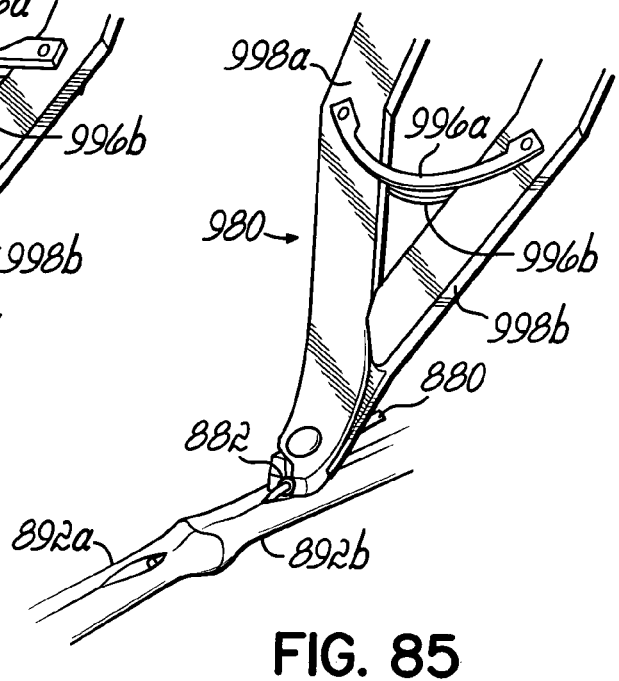
Figure 86:
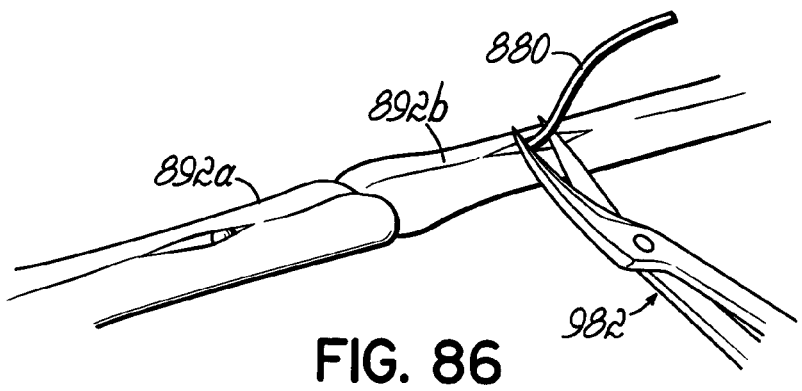
Figure 87:
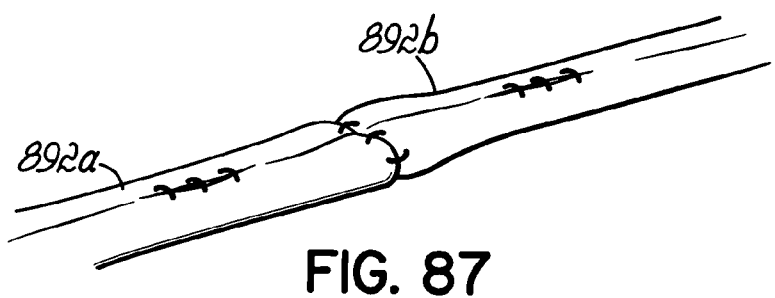

Tendon or ligament segments 892a, 892b are then drawn together using the well-secured anchor assemblies 850 as shown in FIGS. 84 and 85. Anchor assembly 850 in ligament segment 892a is pulled by preset crimp member 964 as anchor assembly 850 in ligament segment 892b is pushed using crimp member 882 and a crimp tool 980. Crimp tool 980 is used to collapse crimp member 882 onto the flexible elongate tensile member 880 to retain the second anchor assembly 850 in position within segment 892b. The first anchor assembly 850 is retained in position by the preset crimp member 964 as previously described. Thus, the tendon or ligament segments 892a, 892b are held at the desired positions relative to each other as determined by the surgeon. The excess length of the elongate tensile member 880 is then cut with a cutting tool 982 at a location adjacent the proximal end of the crimp member 882 as generally shown in FIG. 86 and, as shown in FIG. 87, the access incisions are closed, such as by suturing, and a running suture, or other means, may be used to secure the ends of the tendon or ligament segments 892a, 892b.

Figure 88:
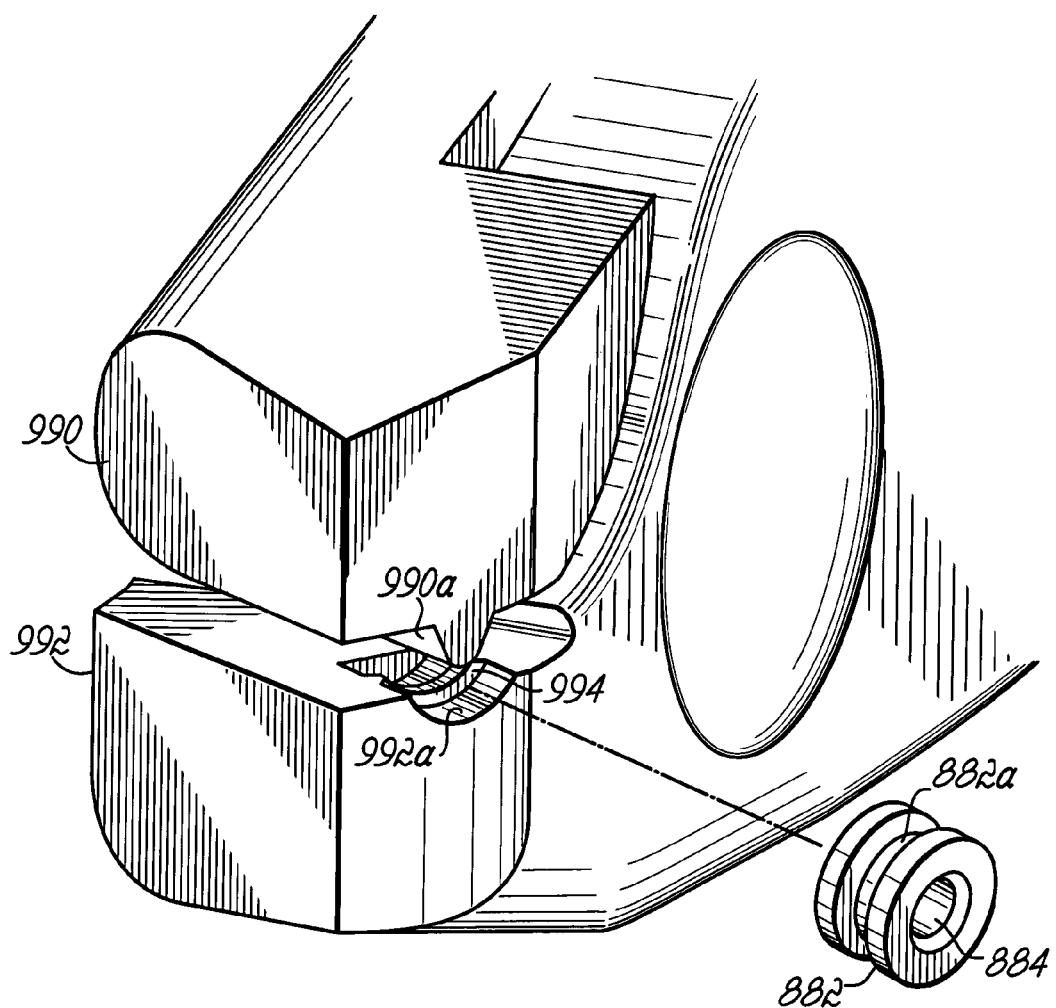
FIG. 88 is an enlarged perspective view showing the jaw portion of a crimp tool and a crimp member each constructed in accordance with additional aspects of the invention.

FIG. 88 shows the jaws 990, 992 of crimp tool 980 in more detail. One jaw 990 includes a projection 990a for collapsing crimp member 882 against a recess 992a formed in the jaw 992. The recess 992a in the opposite jaw includes a ridge 994 which helps retain crimp member 882 in place within the jaws 990, 992, such as during shipping and during use by the surgeon. As also shown in FIGS. 84 and 85, one or more flexible bars 996a, 996b are provided between opposing handles 998a, 998b of crimp tool 980. These bars 996a, 996b retain the jaws 990, 992 at predetermined positions which hold the crimp member 882 in place during packaging, shipping and storage, but prevent jaws 990, 992 from coming together during application of relatively light loads to prematurely collapse the crimp member 882. During use by the surgeon, however, the flexible bar or bars 996a, 996b do not prevent manual actuation of the handles 998a, 998b to bring the jaws 990, 992 together and collapse the crimp member 882 as shown in FIG. 85.

Figure 89:
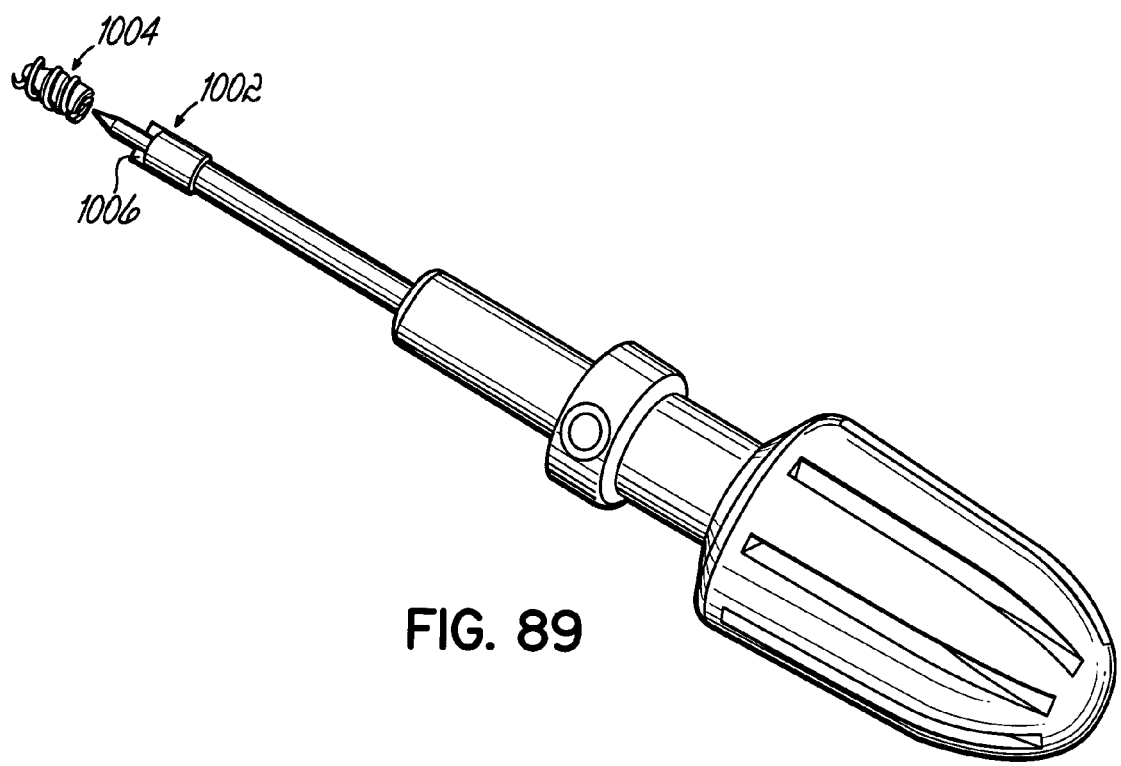
FIG. 89 is a perspective view of an anchor assembly removal tool in accordance with another aspect of the invention.
Figure 90:
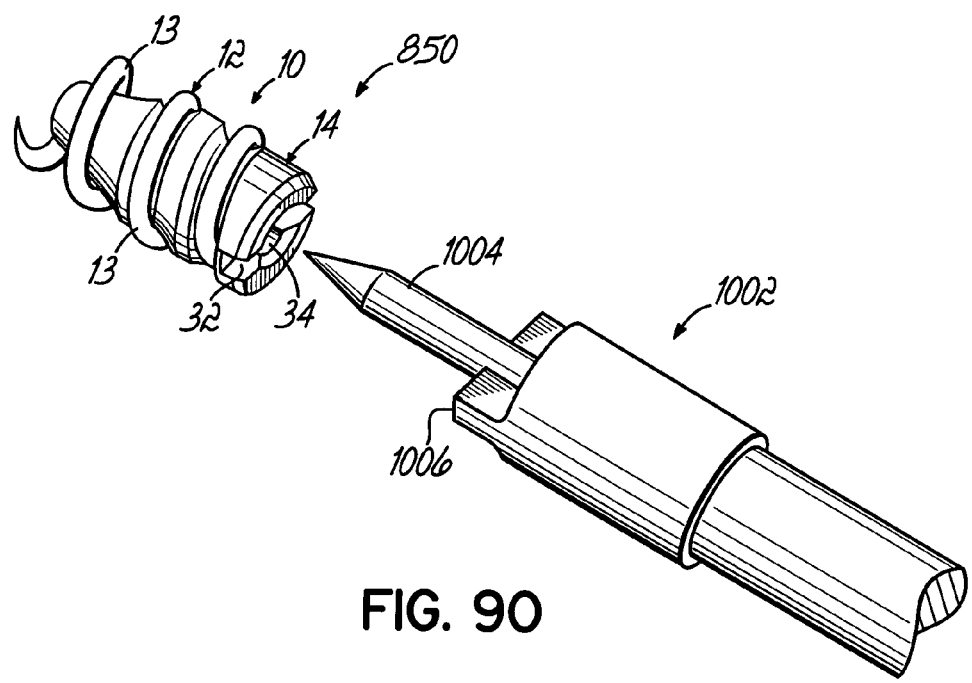
FIG. 90 is an enlarged perspective view of the distal end of the removal tool and the unitary anchor assembly of this invention.

FIGS. 89 and 90 illustrate a removal tool 1000 which, in certain cases, may be necessary to remove an anchor assembly 850. Specifically, removal tool 1000 is in the general form of a rotatable hand tool generally similar to a screwdriver. However, as shown in FIG. 90, tool 1000 includes a head portion 1002 having a needle 1004 extending from a drive portion 1006. Needle 1004 extends through the central bore 878 of anchor assembly 850 and drive portion 1006 engages slot 876 of anchor assembly in a manner similar to a screwdriver to allow rotation of anchor assembly 850. In the configuration shown, counterclockwise rotation of tool 1000 and anchor assembly 850 will back the anchor assembly 850 out of the tendon or ligament 892, for example, if the anchor assembly 850 is malpositioned.

While the present invention has been illustrated by a description of the preferred embodiments and while these embodiments have been described in some detail, it is not the intention of the Applicants to restrict or in any way limit the scope of the appended claims to such detail. The present disclosure has been illustrative of many features which may be modified, and configured in many different sizes depending on the intended use. The various embodiments and features of the invention may be used singularly or in various combinations not to be limited by the detail provided herein. Additional advantages and modifications will readily appear to those skilled in the art. This has been a description of the present invention, along with the preferred methods of practicing the present invention as currently known. Various aspects of this invention may be used alone or in different combinations. The scope of the invention itself should only be defined by the appended claims, wherein we claim:

1. Apparatus for affixing a tendon or ligament to a bone, the apparatus comprising:
   an elongate tensile member adapted to extend within the interior of said tendon or ligament;
   a helical anchor coupled with said elongate tensile member and configured to be placed within the tendon or ligament;
   a retaining member coupled to said elongate tensile member and disposed at least partially within said helical anchor to define an interior space for receiving fibrous tissue of the tendon or ligament; and
   a bone anchor coupled with said elongate tensile member for allowing attachment of said tendon or ligament to said bone.

2. The apparatus of claim 1, further comprising a slidable locking member coupled with said elongate tensile member and adapted to hold said retaining member at a desired location along said elongate tensile member.

3. The apparatus of claim 2, wherein said slidable locking member is formed integrally with said retaining member.

4. The apparatus of claim 1, wherein said helical anchor is compressible.

5. Apparatus for affixing a tendon or ligament to a bone, the apparatus comprising:
   an elongate tensile member adapted to extend within the interior of said tendon or ligament;
   a helical anchor coupled with said elongate tensile member and having an interior space for receiving fibrous tissue of the tendon or ligament;
   a bone anchor coupled with said elongate tensile member and positioned outside of said interior space for allowing attachment of said tendon or ligament to said bone;
   a retaining member adapted to be retained at a selected position along said elongate tensile member to hold said bone anchor, said elongate tensile member and said helical anchor together with said tendon or ligament against said bone, said retaining member sized and configured to be received at least partially within said helical anchor; and
   a slidable locking member coupled with said elongate tensile member and adapted to hold said retaining member at a desired location along said elongate tensile member, wherein said slidable locking member is separable from said retaining member.

6. Apparatus for affixing a tendon or ligament to a bone, the apparatus comprising:
   an elongate tensile member adapted to extend within the interior of said tendon or ligament;
   a helical anchor coupled with said elongate tensile member and having an interior space for receiving fibrous tissue of the tendon or ligament;
   a bone anchor coupled with said elongate tensile member and positioned outside of said interior space for allowing attachment of said tendon or ligament to said bone;
   a retaining member adapted to be retained at a selected position along said elongate tensile member to hold said bone anchor, said elongate tensile member and said helical anchor together with said tendon or ligament against said bone, said retaining member sized and configured to be received at least partially within said helical anchor; and
   a slidable locking member coupled with said elongate tensile member and adapted to hold said retaining member at a desired location along said elongate tensile member, wherein said slidable locking member is a crimp member.

7. A method of repairing a tendon or ligament having fibers extending in a lengthwise direction, comprising:
   inserting an elongate tensile member within the tendon or ligament;

inserting an anchor structure within a tendon or ligament;

attaching a bone anchor to a bone;

coupling the elongate tensile member to the anchor structure;

coupling the elongate tensile member to the bone anchor applying tension to the elongate tensile member to approximate the tendon or ligament and the bone; and securing a stop member to the elongate tensile member and against the anchor structure.

8. A method of repairing a tendon or ligament having fibers extending in a lengthwise direction, comprising:

inserting an elongate tensile member within the tendon or ligament;

inserting a helical anchor within a tendon or ligament;

attaching a bone anchor to a bone;

gripping fibers of the tendon or ligament between the helical anchor and a retaining member;

coupling the elongate tensile member to the helical anchor;

coupling the elongate tensile member to the bone anchor; and applying tension to the elongate tensile member to approximate the tendon or ligament and the bone.

\* \* \* \* \*